(12) United States Patent
Subramanian et al.

(10) Patent No.: US 11,568,998 B2
(45) Date of Patent: Jan. 31, 2023

(54) SYSTEMS AND METHODS FOR ENHANCED NETWORKING AND REMOTE COMMUNICATIONS

(71) Applicant: Omnicure Inc., Ladue, MO (US)

(72) Inventors: Sanjay Subramanian, Ladue, MO (US); Jan Kasal, St. Louis, MO (US); Paramesh Vaidyanathan, Bellevue, WA (US); Andrew Lueck, Seattle, WA (US); Oren Kodish, Chicago, IL (US)

(73) Assignee: Omnicure Inc., Ladue, MO (US)

( * ) Notice: Subject to any disclaimer, the term of this patent is extended or adjusted under 35 U.S.C. 154(b) by 0 days.

(21) Appl. No.: 17/551,128

(22) Filed: Dec. 14, 2021

(65) Prior Publication Data

US 2022/0199267 A1 Jun. 23, 2022

Related U.S. Application Data

(60) Provisional application No. 63/125,809, filed on Dec. 15, 2020.

(51) Int. Cl.
| | |
|---|---|
| *G16H 80/00* | (2018.01) |
| *G16H 50/20* | (2018.01) |
| *G16H 40/67* | (2018.01) |
| *G06V 20/20* | (2022.01) |
| *G06V 10/82* | (2022.01) |

(Continued)

(52) U.S. Cl.
CPC ........... *G16H 80/00* (2018.01); *G06F 3/0488* (2013.01); *G06T 7/10* (2017.01); *G06T 7/20* (2013.01); *G06T 19/006* (2013.01); *G06V 10/82* (2022.01); *G06V 20/20* (2022.01); *G16H 40/67* (2018.01); *G16H 50/20* (2018.01); *G06T 2207/20081* (2013.01); *G06T 2207/20084* (2013.01); *G06T 2207/30196* (2013.01)

(58) Field of Classification Search
None
See application file for complete search history.

(56) References Cited

U.S. PATENT DOCUMENTS

2010/0082370 A1* 4/2010 Frederick ............... G06Q 10/10
705/3
2014/0259056 A1* 9/2014 Grusd .................. H04N 21/812
725/34

(Continued)

*Primary Examiner* — Frank S Chen
(74) *Attorney, Agent, or Firm* — Wilson Sonsini Goodrich & Rosati

(57) ABSTRACT

A system and method for medical communications is disclosed. The system and method may operate to receive, from a user communication node, an electronic signal comprising a communication request including a request description; select, from the list of network entities corresponding to third parties, one or more network entities based at least in part on (i) a parameter profile associated with a third party, and (ii) criteria extracted from the communication request including the request description; transmit an electronic signal, to one or more network entities, the communication request including the request description; receive an action from one of the selected network entities corresponding to third parties in response to the communication request; and provide an interactive communication panel to the user communication node and the one of the selected network entities to facilitate the real-time communication session.

23 Claims, 36 Drawing Sheets

(51) Int. Cl.
    *G06T 7/10*         (2017.01)
    *G06T 19/00*      (2011.01)
    *G06F 3/0488*     (2022.01)
    *G06T 7/20*         (2017.01)

(56) References Cited

U.S. PATENT DOCUMENTS

| | | | |
|---|---|---|---|
| 2017/0116384 A1* | 4/2017 | Ghani | G16H 70/20 |
| 2021/0375452 A1* | 12/2021 | Lin | G16H 80/00 |
| 2021/0378754 A1* | 12/2021 | Olson | G16H 40/60 |
| 2022/0031965 A1* | 2/2022 | Durfee | A61B 5/444 |
| 2022/0108790 A1* | 4/2022 | Rice | G16H 10/60 |
| 2022/0165391 A1* | 5/2022 | Cameron | G16H 20/70 |

\* cited by examiner

Registered Hospitals

| id | Name | AHA | Type | Address | Region | Sub Region |
|---|---|---|---|---|---|---|
| 4923136719736832 | Lake County Mem... | 65464356 | Hospital | Painesville, Ohio | Great Lakes | Ohio |
| 5074659767938528 | EAST OHIO REGIO... | 1234567891 | Hospital | 90 NORTH 4TH ST... | Great Lakes | Ohio |
| 5677675785407328 | Boston Medical Ce... | 8938493884 | Hospital | One Boston Medic... | New England | Massachusetts |
| 5091574486205373 | Lakeview Hospital | | Hospital | Chicago | Great Lakes | Illinois |
| 5826093811632598 | MD PnP Lab | 6789878878998 | Site | 65 Landsdowne St... | New England | Massachusetts |
| 5635378944388894 | Rush Medical Center | | Hospital | Chicago | Great Lakes | Illinois |
| 5827476211226872 | Virtual Hospital | | Site | Miami | Southeast | Florida |

| # | Hospital | Bedside Clinician | Remote Provider | Consult Req time | Consult Completion time | Reconsult |
|---|---|---|---|---|---|---|
| 1 | Community Hospital | Lisa Johnston | John Erickson | Sep 17 2021, 02:42 PM | Sep 17 2021, 03:49 PM | |
| 2 | Community Hospital | Angelika Brown | Donna Lisenkov | Sep 18 2021, 01:39 PM | Sep 18 2021, 02:01 PM | Yes |
| 3 | Community Hospital | Angelika Brown | John Erickson | Sep 18 2021, 06:07 pm | Sep 18 2021, 06:31 PM | |
| 4 | Community Hospital | Lisa Johnston | John Erickson | Sep 21 2021, 10:04 am | Sep 21 2021, 12:03 AM | Yes |
| 5 | Community Hospital | Lisa Johnston | Joseph Meskin | Sep 22 2021, 12:27 pm | Sep 22 2021, 01:40 PM | Yes |
| 6 | Community Hospital | Eric Reinke | Tim Whaley | Sep 24 2021, 10:46 pm | Sep 24 2021, 11:34 PM | |
| 7 | Community Hospital | Eric Reinke | Dennis Petrosyan | Sep 26 2021, 09:46 am | Sep 26 2021, 02:08 PM | Yes |
| 8 | Community Hospital | Eric Reinke | Dennis Petrosyan | Sep 26 2021, 01:11 pm | Sep 26 2021, 01:57 PM | |
| 9 | Community Hospital | Angelika Brown | Tim Whaley | Sep 27 2021, 12:58 pm | Sep 27 2021, 01:56 PM | Yes |
| 10 | Community Hospital | Angelika Brown | Chris Sommers | Sep 29 2021, 02:44 pm | Sep 30 2021, 01:32 pm | |
| 11 | Community Hospital | Tessa Reynolds | Donna Lisenkov | Oct 04 2021, 10:08 pm | Oct 04 2021, 10:57 pm | |

SYSTEMS AND METHODS FOR ENHANCED NETWORKING AND REMOTE COMMUNICATIONS

CROSS-REFERENCE

This application claims the benefit of U.S. Provisional Application No. 63/125,809, filed Dec. 15, 2020, the entire contents of which is hereby incorporated by reference in its entirety.

BACKGROUND

Current telemedicine systems seek to facilitate communications between clinicians and patients in need of medical assistance. However, such systems have various technical deficiencies that make it difficult to provide efficient and high quality care. For example, requests for medical assistance may be broadcast to nodes in a computer network in a manner that can result in inefficient traffic and/or routing over the network for recipient users. These systems also lack integration of patient medical information with healthcare provider communications.

SUMMARY

Disclosed herein is a platform, system, method, and software which enable healthcare providers (e.g., clinicians) to effectively and efficiently communicate with one another in non-emergency and emergency situations. For example, the telemedicine systems disclosed herein help leverage limited specialist resources to efficiently assist large populations. The telemedicine systems and methods should be flexible, scalable, and rapidly-deployable. This may be achieved by a distributed care provider network supported by a vendor agnostic healthcare technology system of systems. In order to mitigate challenges during a healthcare crisis, it would be desirable to provide a system with the ability to rapidly put together a team of critical care physicians to support events from their current physical location.

The present disclosure is directed to an integrated system that allows a distributed network of healthcare providers to effectively and efficiently communicate securely in order to provide Tele Critical Care support. This system allows several forms of digital or electronic communications including messaging, notes, orders, and audio and video communication, in real-time and non-real time, using mobile devices such as smartphones, tablets, or other computing devices to provide acute care to hospitalized patients, and to address clinical emergencies, in real-time across multiple hospitals. This system can provide an efficiently-organized matching mechanism to match the desired or appropriate health care provider(s) to a pending request for medical assistance, and therefore create communication channel between these client nodes. The system can provide an intuitive device-agnostic mobile-friendly software platform usable on smartphones, tablets, and audio-visual enabled web-based computers for on-demand bedside to remote intensivist consultation and critical care decision support.

In some embodiments, the system may allow remote intensivists to perform video assessment of patients, view bedside devices, interfaced vital signs, laboratory data, and/or exchange clinical information through secure messaging and audio-video communications to allow efficient critical care support whenever and wherever it is needed.

In some embodiments, the system may be used to complete tele-consults, with the optional integration of medical devices and sensors, may provide a comprehensive remote patient monitoring solution. Each additional device that is incorporated may broaden the reach of the "device ecosystem" and may include wearables, wellness monitors, smart watches, etc. to increase the chances that a population affected by a disaster would either 1) already be wearing a "physiology monitor" or 2) would have a compatible device included in a local healthcare system response. The system may be able to gather data from environmental sensors and other nonmedical sensors in order to provide additional context to the scenario. In some embodiments, the system extracts raw data from one or more of the disparate devices and sensors and maps the data to a uniform template (see, e.g., FIG. 32 showing aggregation of data extracted from disparate devices and FIG. 29D showing the data mapped to a uniform template shown to a remote healthcare provider via a mobile app dashboard). This can provide standardized data to facilitate a healthcare provider's evaluation of the patient status. The collected and aggregated standardized data can be readily available for real time analysis and dashboards aiding in emergency management during the crisis, and may provide information for retrospective analysis, quality assurance, and training to improve care during future events. This data may enable the development of force multiplying technologies such as remote control of devices and autonomous care systems.

Disclosed herein, in one aspect, is a computer-implemented method for providing real-time healthcare communication, comprising: receiving, by one or more computer processors, from a client node, a request of consult describing a medical condition for a patient; selecting, by the one or more computer processors, from a list of healthcare providers, one or more healthcare providers based at least in part on (i) a profile associated with healthcare provider, and (ii) criteria extracted from the request of consult; presenting, by the one or more computer processors, to the selected healthcare providers, the request of consult; receiving, by the one or more computer processors, an action from one of the selected healthcare providers in response to the request of consult; and providing, by the one or more computer processors, an interactive communication panel to the client node for the patient and the healthcare provider to facilitate the real-time healthcare communication. In some embodiments, (a)-(e) are performed by the one or more computer processors in real-time. The method of claim 1, further comprising, prior to (a), maintaining, by the one or more computer processors, the list of healthcare providers and the profile associated with the list of healthcare providers. In some embodiments, (c) further comprises: broadcasting a notification of the request of consult to the list of healthcare providers; and allow a healthcare provider from the selected healthcare providers to take over control when two or more healthcare providers respond to the request of consult during a same time window. In some embodiments, the request of consult comprises an acuity level. In some embodiments, further comprising, prior to (a), retrieving, by the one or more computer processors, a health record associated with the patient. In some embodiments, the criteria extracted from the request of consult comprises criteria extracted from the health record associated with the patient. In some embodiments, further comprising, prior to (a), authenticating, by the one or more computer processors, credentials of the healthcare providers and their affiliated hospitals. In some embodiments, an access to the health record is restricted to the authenticated healthcare providers. In some embodiments, the real-time healthcare communication comprises messages, audio calls, video calls, orders, and notes.

In some embodiments, (b) comprises applying a matching algorithm to the list of healthcare providers to identify the one or more healthcare providers as suitable for responding to the request for consult. In some embodiments, the interactive communication panel for the client node and/or the healthcare provider comprises a virtual dashboard displaying medical information for the patient. In some embodiments, further comprising consolidating medical information for the patient from a plurality of sources and providing the medical information to the client node and/or the healthcare provider. In some embodiments, further comprising creating a team of healthcare providers suitable for responding to the request for consult. In some embodiments, the team of healthcare providers comprises a plurality of medical roles. In some embodiments, the healthcare provider is at a remote location not in proximity to the patient. In some embodiments, selecting the one or more healthcare providers comprises providing load balancing of workload for healthcare providers to optimize the ratio of requests for consult to available resources. In some embodiments, further comprising expanding selection of the one or more healthcare providers by modifying a matching algorithm when the request for consult is not responded to within a time duration. In some embodiments, the time duration is preset or dynamically set based on parameters comprising total number of requests for consult, availability of healthcare providers, average duration of a consult, complexity of consult, individual provider efficiency, or any combination thereof. In some embodiments, further comprising providing data analytics to the client node and/or healthcare provider, optionally wherein the data analytics is displayed through a virtual command center provided to the client node and/or healthcare provider. In some embodiments, further comprising providing an augmented reality or virtual reality display to the client node and/or healthcare provider.

In another aspect, disclosed herein is a non-transitory computer-readable medium comprising machine-executable code that, upon execution by one or more computer processors, implements a method for providing real-time graphically distinct items in a user experience, comprising: receiving, from a client node, a request of consult describing a medical condition for a patient; selecting, from a list of healthcare providers, one or more healthcare providers based at least in part on (i) a profile associated with healthcare provider, and (ii) criteria extracted from the request of consult; presenting to the selected healthcare providers the request of consult; receiving, an action from one of the selected healthcare providers in response to the request of consult; and providing, an interactive communication panel to the client node for the patient and the healthcare provider to facilitate the real-time healthcare communication. In some embodiments, (a)-(e) are performed by the one or more computer processors in real-time. In some embodiments, further comprising, prior to (a), maintaining, by the one or more computer processors, the list of healthcare providers and the profile associated with the list of healthcare providers. In some embodiments, (c) further comprises: broadcasting a notification of the request of consult to the list of healthcare providers; and allow a healthcare provider from the selected healthcare providers to take over control when two or more healthcare providers respond to the request of consult during a same time window. In some embodiments, the request of consult comprises an acuity level. In some embodiments, further comprising, prior to (a), retrieving, by the one or more computer processors, a health record associated with the patient. In some embodiments, the criteria extracted from the request of consult comprises criteria extracted from the health record associated with the patient. In some embodiments, further comprising, prior to (a), authenticating, by the one or more computer processors, credentials of the healthcare providers and their affiliated hospitals. In some embodiments, an access to the health record is restricted to the authenticated healthcare providers. In some embodiments, the real-time healthcare communication comprises messages, audio calls, video calls, orders, and notes. In some embodiments, (b) comprises applying a matching algorithm to the list of healthcare providers to identify the one or more healthcare providers as suitable for responding to the request for consult. In some embodiments, the interactive communication panel for the client node and/or the healthcare provider comprises a virtual dashboard displaying medical information for the patient. In some embodiments, further comprising consolidating medical information for the patient from a plurality of sources and providing the medical information to the client node and/or the healthcare provider. In some embodiments, further comprising creating a team of healthcare providers suitable for responding to the request for consult. In some embodiments, the team of healthcare providers comprises a plurality of medical roles. In some embodiments, the healthcare provider is at a remote location not in proximity to the patient. In some embodiments, selecting the one or more healthcare providers comprises providing load balancing of workload for healthcare providers to optimize the ratio of requests for consult to available resources. In some embodiments, further comprising expanding selection of the one or more healthcare providers by modifying a matching algorithm when the request for consult is not responded to within a time duration. In some embodiments, the time duration is preset or dynamically set based on parameters comprising total number of requests for consult, availability of healthcare providers, average duration of a consult, complexity of consult, individual provider efficiency, or any combination thereof. In some embodiments, further comprising providing data analytics to the client node and/or healthcare provider, optionally wherein the data analytics is displayed through a virtual command center provided to the client node and/or healthcare provider. In some embodiments, further comprising providing an augmented reality or virtual reality display to the client node and/or healthcare provider.

Disclosed herein, in another aspect, is a system comprising a network communication element, one or more computer processors, and non-transitory computer readable storage medium comprising machine-executable instructions that, upon execution by the one or more computer processors, causes the one or more computer processors to: (a) receive, from a client node, a request of consult describing a medical condition for a patient; (b) select, from a list of healthcare providers, one or more healthcare providers based at least in part on (i) a profile associated with healthcare provider, and (ii) criteria extracted from the request of consult; (c) present to the selected healthcare providers the request of consult; (d) receive, an action from one of the selected healthcare providers in response to the request of consult; and (e) provide, an interactive communication panel to the client node for the patient and the healthcare provider to facilitate the real-time healthcare communication. In some embodiments, (a)-(e) are performed by the one or more computer processors in real-time. In some embodiments, prior to (a), maintain, by the one or more computer processors, the list of healthcare providers and the profile associated with the list of healthcare providers. In some embodiments, (c) further comprises: broadcast a notification of the request of consult to the list of healthcare providers; and allow a healthcare provider from the selected healthcare providers to take over control when two or more healthcare providers respond to the request of consult during a same time window. In some embodiments, the request of consult comprises an acuity level. In some embodiments, further comprising, prior to (a), retrieve, by the one or more computer processors, a health record associated with the patient. In some embodiments, the criteria extracted from the request of consult comprises criteria extracted from the health record associated with the patient. In some embodiments, further comprising, prior to (a), authenticate, by the one or more computer processors, credentials of the healthcare providers and their affiliated hospitals. In some embodiments, an access to the health record is restricted to the authenticated healthcare providers. In some embodiments, the real-time healthcare communication comprises messages, audio calls, video calls, orders, and notes. In some embodiments, (b) comprises applying a matching algorithm to the list of healthcare providers to identify the one or more healthcare providers as suitable for responding to the request for consult. In some embodiments, the interactive communication panel for the client node and/or the healthcare provider comprises a virtual dashboard displaying medical information for the patient. In some embodiments, further comprising consolidating medical information for the patient from a plurality of sources and providing the medical information to the client node and/or the healthcare provider. In some embodiments, further comprising creating a team of healthcare providers suitable for responding to the request for consult. In some embodiments, the team of healthcare providers comprises a plurality of medical roles. In some embodiments, the healthcare provider is at a remote location not in proximity to the patient. In some embodiments, selecting the one or more healthcare providers comprises providing load balancing of workload for healthcare providers to optimize the ratio of requests for consult to available resources. In some embodiments, further comprising expanding selection of the one or more healthcare providers by modifying a matching algorithm when the request for consult is not responded to within a time duration. In some embodiments, the time duration is preset or dynamically set based on parameters comprising total number of requests for consult, availability of healthcare providers, average duration of a consult, complexity of consult, individual provider efficiency, or any combination thereof. In some embodiments, further comprising providing data analytics to the client node and/or healthcare provider, optionally wherein the data analytics is displayed through a virtual command center provided to the client node and/or healthcare provider. In some embodiments, further comprising providing an augmented reality or virtual reality display to the client node and/or healthcare provider.

In another aspect, disclosed herein is a computer-implemented method for providing a real-time network communication session, comprising: (a) receiving, by one or more computer processors, from a user communication node, an electronic signal comprising a communication request including a request description; (b) selecting, by the one or more computer processors, from a list of network entities corresponding to third parties, one or more network entities based at least in part on (i) a parameter profile associated with a third party, and (ii) criteria extracted from the communication request including the request description; (c) transmitting an electronic signal, by the one or more computer processors, to one or more network entities, the communication request including the request description; (d) receiving, by the one or more computer processors, an action from one of the selected network entities corresponding to third parties in response to the communication request; and (e) providing, by the one or more computer processors, an interactive communication panel to the user communication node and the one of the selected network entities to facilitate the real-time communication session. In some embodiments, further comprising aggregating data related to the criteria from a plurality of data sources and processing the data according to a standard format. In some embodiments, further comprising performing data analytics on the data to generate a suggestion for one or more actions. In some embodiments, performing data analytics comprises processing the data using a machine learning algorithm. In some embodiments, the interactive communication panel provides a graphical user interface shown on an interactive touchscreen display. In some embodiments, the interactive communication panel provides an augmented reality video feed between the user communication node and the one of the selected network entities. In some embodiments, further comprising providing tracking of an object shown in the augmented reality video feed. In some embodiments, the object is tracked using a computer vision algorithm trained to detect and track the object. In some embodiments, the computer vision algorithm comprises an image segmentation algorithm or a machine learning algorithm. In some embodiments, the machine learning algorithm is a deep convolutional neural network. In some embodiments, the user communication node is a client node. In some embodiments, the communication request comprising a request description is a request of consult describing a medical condition of a patient. In some embodiments, a network entity of a third party is a communication device of a remote healthcare provider.

Disclosed herein, in another aspect, is a system comprising a network communication element, one or more computer processors, and non-transitory computer readable storage medium comprising machine-executable instructions that, upon execution by the one or more computer processors, causes the one or more computer processors to: (a) receive, by one or more computer processors, from a user communication node, an electronic signal comprising a communication request including a request description; (b) select, by the one or more computer processors, from a list of network entities corresponding to third parties, one or more network entities based at least in part on (i) a parameter profile associated with a third party, and (ii) criteria extracted from the communication request including the request description; (c) transmit an electronic signal, by the one or more computer processors, to one or more network entities, the communication request including the request description; (d) receive, by the one or more computer processors, an action from one of the selected network entities corresponding to third parties in response to the communication request; and (e) provide, by the one or more computer processors, an interactive communication panel to the user communication node and the one of the selected network entities to facilitate the real-time communication session. In some embodiments, further comprising aggregating data related to the criteria from a plurality of data sources and processing the data according to a standard format. In some embodiments, further comprising performing data analytics on the data to generate a suggestion for one or more actions. In some embodiments, performing data analytics comprises processing the data using a machine learning algorithm. In some embodiments, the interactive communication panel provides a graphical user interface shown on an interactive touchscreen display. In some embodiments, the interactive communication panel provides an augmented reality video feed between the user communication node and the one of the selected network entities. In some embodiments, further comprising providing tracking of an object shown in the augmented reality video feed. In some embodiments, the object is tracked using a computer vision algorithm trained to detect and track the object. In some embodiments, the computer vision algorithm comprises an image segmentation algorithm or a machine learning algorithm. In some embodiments, the machine learning algorithm is a deep convolutional neural network. In some embodiments, the user communication node is a client node. In some embodiments, the communication request comprising a request description is a request of consult describing a medical condition of a patient. In some embodiments, a network entity of a third party is a communication device of a remote healthcare provider.

Disclosed herein, in another aspect, is a system comprising a network communication element, one or more computer processors, and non-transitory computer readable storage medium comprising machine-executable instructions that, upon execution by the one or more computer processors, causes the one or more computer processors to: (a) receive from a user communication node, an electronic signal comprising a communication request including a request description; (b) select from a list of network entities corresponding to third parties, one or more network entities based at least in part on (i) a parameter profile associated with a third party, and (ii) criteria extracted from the communication request including the request description; (c) transmit an electronic signal to one or more network entities, the communication request including the request description; (d) receive an action from one of the selected network entities corresponding to third parties in response to the communication request; and (e) provide an interactive communication panel to the user communication node and the one of the selected network entities to facilitate the real-time communication session. In some embodiments, further comprising aggregating data related to the criteria from a plurality of data sources and processing the data according to a standard format. In some embodiments, further comprising performing data analytics on the data to generate a suggestion for one or more actions. In some embodiments, performing data analytics comprises processing the data using a machine learning algorithm. In some embodiments, the interactive communication panel provides a graphical user interface shown on an interactive touchscreen display. In some embodiments, the interactive communication panel provides an augmented reality video feed between the user communication node and the one of the selected network entities. In some embodiments, further comprising providing tracking of an object shown in the augmented reality video feed. In some embodiments, the object is tracked using a computer vision algorithm trained to detect and track the object. In some embodiments, the computer vision algorithm comprises an image segmentation algorithm or a machine learning algorithm. In some embodiments, the machine learning algorithm is a deep convolutional neural network. In some embodiments, the user communication node is a client node. In some embodiments, the communication request comprising a request description is a request of consult describing a medical condition of a patient. In some embodiments, a network entity of a third party is a communication device of a remote healthcare provider.

In some embodiments, the system includes a platform and application with one or more of the following in any combination:

An integrated communication interface (audio, video, text, etc.) between healthcare providers across multiple locations and hospitals for the provision of patient care in real time related to acute care and emergencies.

Provide synchronous (audio/video) and asynchronous (text/messaging/email) communications.

Comprehensive system that organizes healthcare providers into configurable remote teams based on real time demand and workflow optimization with integrated workflow management and workload distribution.

A process for presenting a customized user interface to each provider, e.g., depending on their role or customization settings.

A system to initiate, manage, and document communications across healthcare providers.

A system to recruit, assign, and bring online clinical staff within minutes.

Provide real-time clinical data (e.g., vital signs, laboratory results, device monitoring, etc.) for medical decision making.

A combination of real-time clinical data, patients and patient care teams, and team communication.

Secure access to patient data.

Provide real-time data collection for real-time and retrospective analysis.

Provide triage point for self-enrolling patients.

Provide clinical decision support tools and training tools to providers.

Provide resources such as cognitive aids, clinical and technical references, care plans and best practices which can be downloaded to a smart phone long before an emergency occurs and automatically updated on a regular basis.

A system to collect and aggregate standardized data which may be readily available for real-time analysis and dashboards aiding in emergency management during the crisis, and which may provide information for retrospective analysis, quality assurance, and training to improve care during future events.

A system to aggregate historical data for retrospective analysis, and a mechanism to utilize retrospective analysis to build a model which may i) provide better matching between healthcare provider and patient in need of medical assistance; ii) provide recommended or suggested medication or tests or clinical reassessment/follow up in a certain situation (e.g., based on vital signs, laboratory results, or device monitoring data, etc.); iii) provide actionable insights for developer to build additional tools for the telemedicine platform, etc.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

A better understanding of the features and advantages of the present disclosure can be obtained by reference to the following detailed description that sets forth illustrative embodiments, in which the principles of the disclosure are utilized, and the accompanying drawings of which:

FIG. 22 shows a view of a user interface for an administrator portal hospital management tool, according to one or more embodiments herein.

FIG. 29A shows a list of consults for a remote healthcare provider as shown on a smartphone display. FIG. 29B shows patient information including the associated hospital and the unit of the hospital (in this case, ICU). FIG. 29C shows the capability and interface to connect to a device associated with the patient. FIG. 29D shows a dashboard with medical data for the patient mapped from disparate sources, including in this illustrative example, demographics (age, gender), location, disease or condition, details, and real-time or near real-time vitals (heart rate, blood pressure, RR, SPO2, temperature, AVPU, supplemental oxygen status, and FiO2.

FIG. 33 shows a command center dashboard displaying medical data for a list of patients, according to one or more embodiments herein.

FIG. 35 shows an illustrative example of a list of consult data exportable in CSV format, according to one or more embodiments herein.

DETAILED DESCRIPTION

Figure 1:
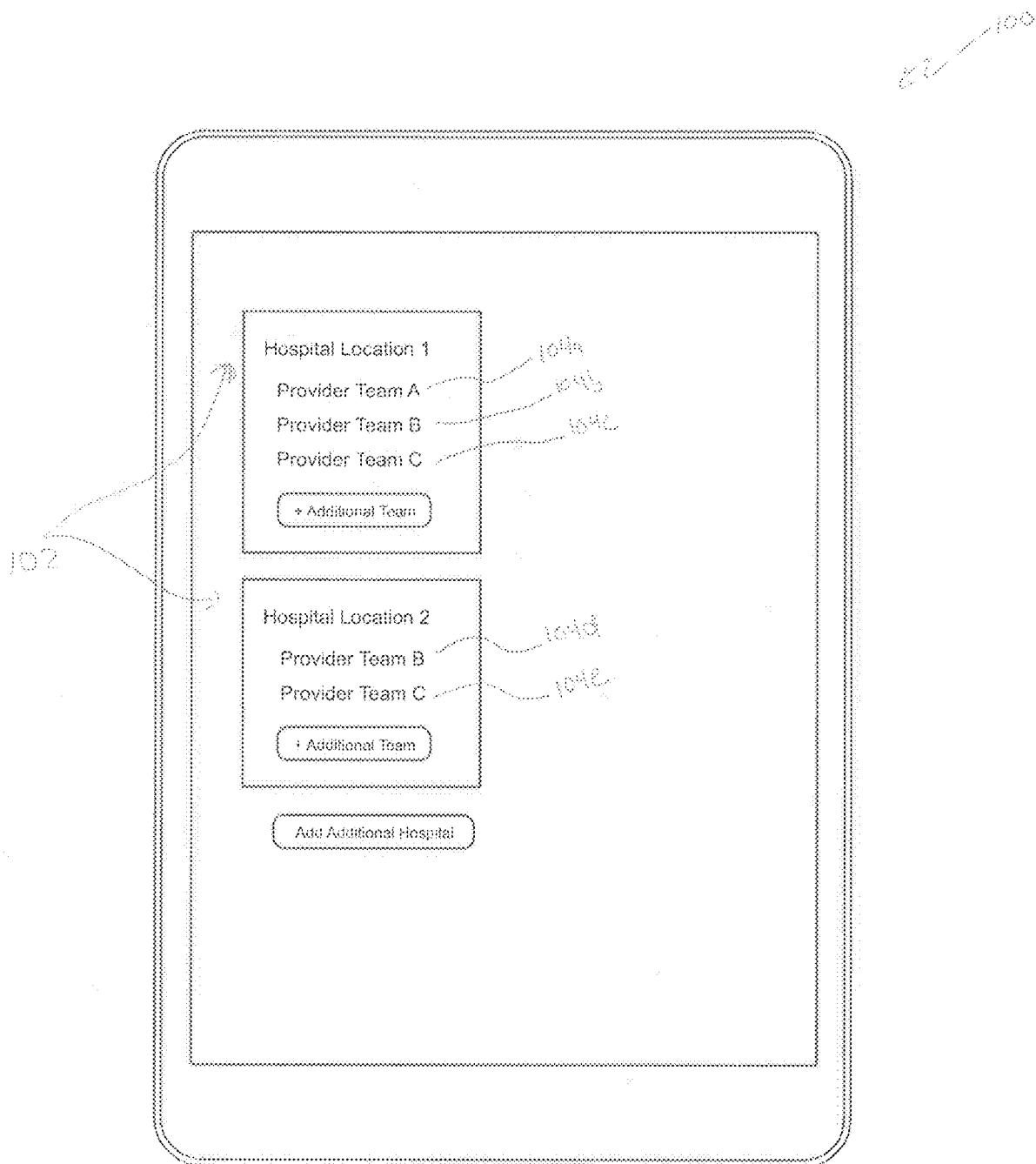
FIG. 1 is a view of a device displaying teams of providers spanning multiple hospitals across disparate physical locations, according to one or more embodiments herein.

Disclosed herein are platforms, systems, methods, and software for providing an integrated telemedicine system and network that facilitates communications between healthcare providers and patients who are located remotely from one another. There exists a lack of such an integrated, comprehensive telemedicine system that may bridge healthcare provider and patients in need of medical assistance. During public health emergencies medical services need to rapidly mobilize. During this mobilization, information is constantly changing, new information needs to be gathered as it evolves, and disseminated to local and remote care providers and other agencies. Often these emergencies occur without warning.

The platforms, systems, methods, and software disclosed herein provide various advantages that address deficiencies in the current state of telemedicine and medical communications. Clinicians use telemedicine to evaluate, diagnose, treat, and monitor patients with audio and video technologies. A computer network for telemedicine may facilitate the exchange and/or delivery of data packets, or communications, between multiple client nodes associated with healthcare providers and patient in need of medical assistance. Often, a data packet containing a request for medical assistance may be broadcast to all nodes in the computer network. However, this may create unnecessary traffic over the network and an overload of information for the recipient users. Additionally, in the field of healthcare, the healthcare providers' specialties and availabilities may need to be taken into consideration when matching a request for medical assistance with a healthcare provider. Accordingly, in some embodiments, disclosed herein is a platform, system, method, and software that provides a market-based environment in which requests or consults are transmitted by patients to pre-filtered or screened network of nodes for healthcare providers who are remotely located from the patient and who can accept or claim the requests or consults at their discretion. The request or consult may be configured with one or more parameters for screening for the appropriate healthcare provider (e.g., specifying an area of specialization). Alternatively or in combination, the healthcare provider may also configure their profile or consult configurations to screen the requests or consults (e.g., removing consult requests involving certain medical conditions that are better evaluated by a different type of specialist).

Existing telemedicine systems for providing care to hospitalized patients use dedicated fixed hardware with disparate systems for the evaluation and treatment of patients by both local and remote healthcare providers. Such disparate systems lack the integration of patient medical information with healthcare provider communications. Further, healthcare providers using such hardware and disparate systems do so in physical medical workspaces and communication centers which can cause delays in communicating healthcare information and solutions and can also inhibit the recordation and communication of accurate and timely patient status and solutions to immediate and near-term patient health concerns. Healthcare providers lack a mobile and expansive mechanism for secure access to medical data integrated with remote communication across multiple hospitals to provide. Accordingly, in some embodiments, disclosed herein is a platform, system, method, and software that provides integration of medical information with remote communications across various healthcare settings such as hospitals and clinics to enable efficient bridging of healthcare providers with patients in order to give providers access to relevant medical information and facilitate real-time communications of healthcare solutions.

Additionally, there currently exists a lack of infrastructure to quickly respond to natural disasters, mass casualty events, and other medical emergencies. During public health emergencies medical services may need to be rapidly mobilized. During this mobilization, information is constantly changing, new information needs to be gathered as it evolves, and disseminated to local and remote care providers and other agencies. Often these emergencies occur without warning. The national response to COVID-19 has highlighted the fragility of healthcare systems. The initial response has demonstrated the need for skilled care providers and resources to support them, in both urban and rural areas, when local resources are overwhelmed or unavailable. Healthcare providers may be confronted by unfamiliar situations, disease processes, and unfamiliar equipment or equipment shortages. These challenges are compounded as most critical care physicians are in high population urban areas, leaving rural and smaller hospitals lacking the experience and technology to manage large volumes of patients. The resources available to healthcare providers and critical care response teams are currently less than ideal.

Accordingly, the platforms, systems, methods, and software described herein may be part of an emergency preparedness system able to provide resources such as cognitive aids, clinical and technical references, care plans and/or best practices which can be downloaded to a smart phone long before an emergency occurs and automatically updated on a regular basis. These resources will be invaluable at the time of an emergency when cellular networks may be saturated or there is no connection to the outside world. It may also include clear instructions to local care providers on the assigned tasks with full awareness of how these tasks fit in the overall telemedicine workflow.

In cases where patients require monitoring, telemonitoring can be provided by using the patient's own personal health device, if they are wearing one, or with wireless body sensors that can be rapidly brought to the location of the event. An integrated clinical environment platform may be used to integrate multiple sensors, actuators, and medical devices from different vendors and to ensure the documentation of frequent spot checks or continuous stream of physiological data. This data can be directly used by the local care team to augment local decision making, and/or by remote care experts, who can remotely monitor and/or silence alarms, change device settings, and/or directly care for patients while the local care team assists other patients. The data may be beneficial both to the local care team by reducing their workload and most importantly to the patient. There is also a need for local support and sharing of information. Frequently large-scale emergencies are providing critical care in environments with limited communication infrastructure or where a hospital's traditional infrastructure is too slow or unavailable.

The platforms, systems, methods, and software disclosed herein can provide one or more of the following features:
  Secure on-demand audio and video calls
  Patient-centric synchronous messaging
  Photo and file sharing
  Provider directory and patient census displays
  Multi-user conference calling
  Structured electronic patient handoff
  Prioritization features (e.g., urgency flagging, SOS feature)

In addition, enhanced documentation can be provided through pre-populated basic templates, completion/summary notes, the ability to store and export messages and/or notes into EMR, or any combination thereof.

Clinical data can also be provided during the consultation process. For example, a dashboard can be provided at the client node and/or with the remote healthcare provider (e.g., via a mobile app) that shows one or more of:
  Real-time vitals display
  Graphic display of trends in vitals and labs
  Patient acuity status
  Option for manual data entry
  Option for integration (EMR integration, Medical Device Data Aggregation)

Additional capabilities include administrative portal features (e.g., portal or dashboard accessible by an admin) such as:
  ADT patient list integration
  Upload of patient list
  Manual addition of patients
  Provider verification and approval
  Hospital onboarding
  Send system alerts to users In some embodiments, the dashboard provides analytics features such as one or more of:
  Track patient and consultation volume by location
  Visualize patient acuity on a local and regional level
  Metrics on average response time, provider capacity
  BI Report generation capabilities
  Additional clinical metrics as requested by client on an individual basis FIG. 1 shows a view of a mobile computer 100, such as a tablet, smart phone, or laptop displaying an initial view for a remote physician or healthcare provider when they are logged in to the system. This person may be at a remote location relative to various patients who may be at disparate hospitals and clinics or even at a non-medical location, for example, a long-term care facility such as a nursing home or simply at home. On the left side the tablet 100 may include a list 102 of various hospitals who are subscribed and connected to a network and, under each hospital, each team 104a, 104b, 104c, 104d, 104e assigned to each hospital of the list 102.

Figure 2:
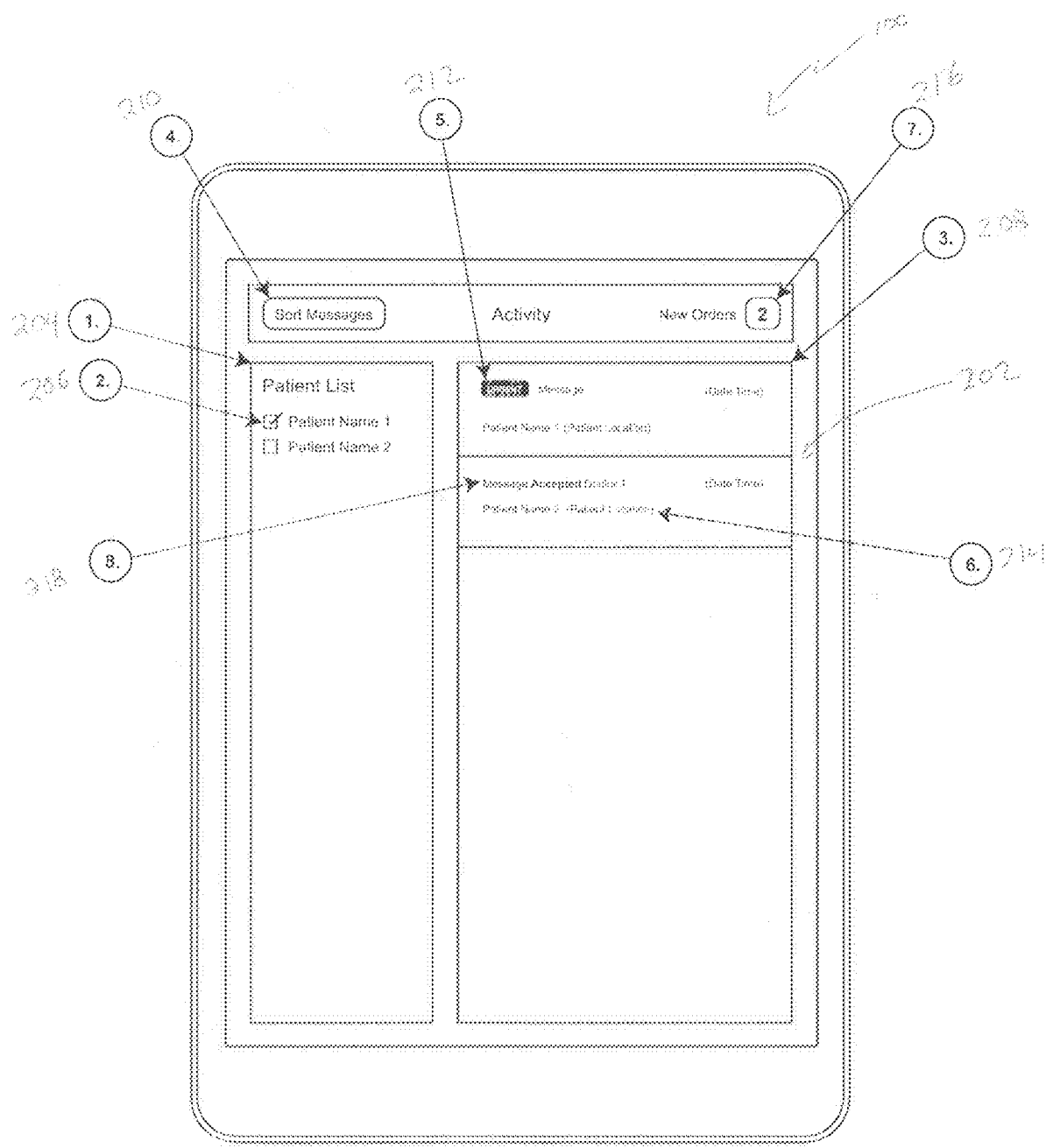
FIG. 2 is a view of the device of FIG. 1 providing a user interface for displaying and receiving information for local medical providers or clinicians, according to one or more embodiments herein.

Referring now to FIG. 2, there is shown the device 100 displaying an interface 202 for a local medical provider, such as a Nurse. The device 100 may display such an interface 202 to facilitate logging into the system through the device 100. The device 100 may include an interface having a list of patients 204 and interface elements 206, such as a check box, beside each patient name in the list of patients 204. The system may receive information from a medical practitioner, such as a nurse, through the interface elements 206, which, for example, allow the nurse to select out the patients they will be caring for during a shift. In some cases, there is a parallel process for selecting the patients the bedside clinician needs consults for. The right pane 208 of the interface 202 may show communication exchanges between the nurse and other healthcare providers, including physicians, other nurses, and physicians' assistants. The device 100 may also include an interface element 210, such as a tab, that allows users to sort messages by date, time, or name and may also include a message flag 212 that can indicate whether a particular message is urgent or not. In some cases, the message or request for consult comprises an urgency level such as, for example, routine, urgent, or emergency (e.g., SOS). The response time or time duration for the request for consult may be adjusted based on the urgency level. For example, routine consult requests may have a 1 hour maximum response time, while urgent has 30 minutes response time, and emergency requires immediate attention. Thus, a bedside provider such as a nurse may prioritize the consult request by setting the level of urgency, which helps the remote provider to prioritize their own worklist if multiple consults are received in a short time frame, for example, by filtering according to urgency status. In the case of an emergency, the consult request or message with the emergency status may cause the application (e.g., mobile app used by remote clinicians) to alert all online/active remote healthcare providers that a bedside clinician needs assistance. The device 100 may also include a message field 214 that contains patient information, such as the patient's location, bed number, and other identifying and localizing information. The device 100 may also include a notification field 216 for new incoming orders for the nurse. The device may also include an indication 218 of a change in message status visible to nurse. The indication 218 may indicate, for example, when a message is accepted by a doctor.

Communications between nurses and other providers, namely other nurses, physician's assistants and doctors, may be in the form of messages (e.g., in-app messaging or via external text messaging systems), audio-video calls (e.g., in-app calls or to an external phone number), orders, notes, and the like. Messages may be a broadcast entity that may be initiated by nurses, physicians, or other providers in the system (e.g., administrators, etc.). These messages can be exchanged as part of a consult, for example, before, during, or after a consult has been accepted or claimed by a remote healthcare provider (e.g., clinician). Audio-video calls are targeted entities and may be initiated by one person to another individual or a group of providers. Orders may be written by doctors or Physician's Assistants and can be processed by nurses. Notes include documenting comments that a doctor or a physician's assistant may wish to add about the patient, etc. All communication happens in the context of a patient. Further, all communication can be tagged with time-stamps. In some embodiments, communications may typically be arranged chronologically. In some embodiments, communications may be sorted by patient name or urgency status. A message highlighted in color may indicate an urgent message broadcast by nurses to other healthcare providers. Each message filed 214 can include unique patient identifying information in the context of their location within a healthcare system. This may help with auditing the care provided to the patient and avoid errors.

In more detail, still referring to FIG. 2, the device 100 may include a notification mechanism for incoming messages, orders or notes from physicians that show up as alerts in the upper right-hand corner in the notification field 216. The remote healthcare provider may receive notifications of a request of consult through various mechanisms, for example, by push notification if on a mobile device, an out-of-app SMS alert, a direct phone call (video or audio), a browser pop up that flashes across the screen on a web-based platform (optionally remains visible as a notification).

Figure 13:
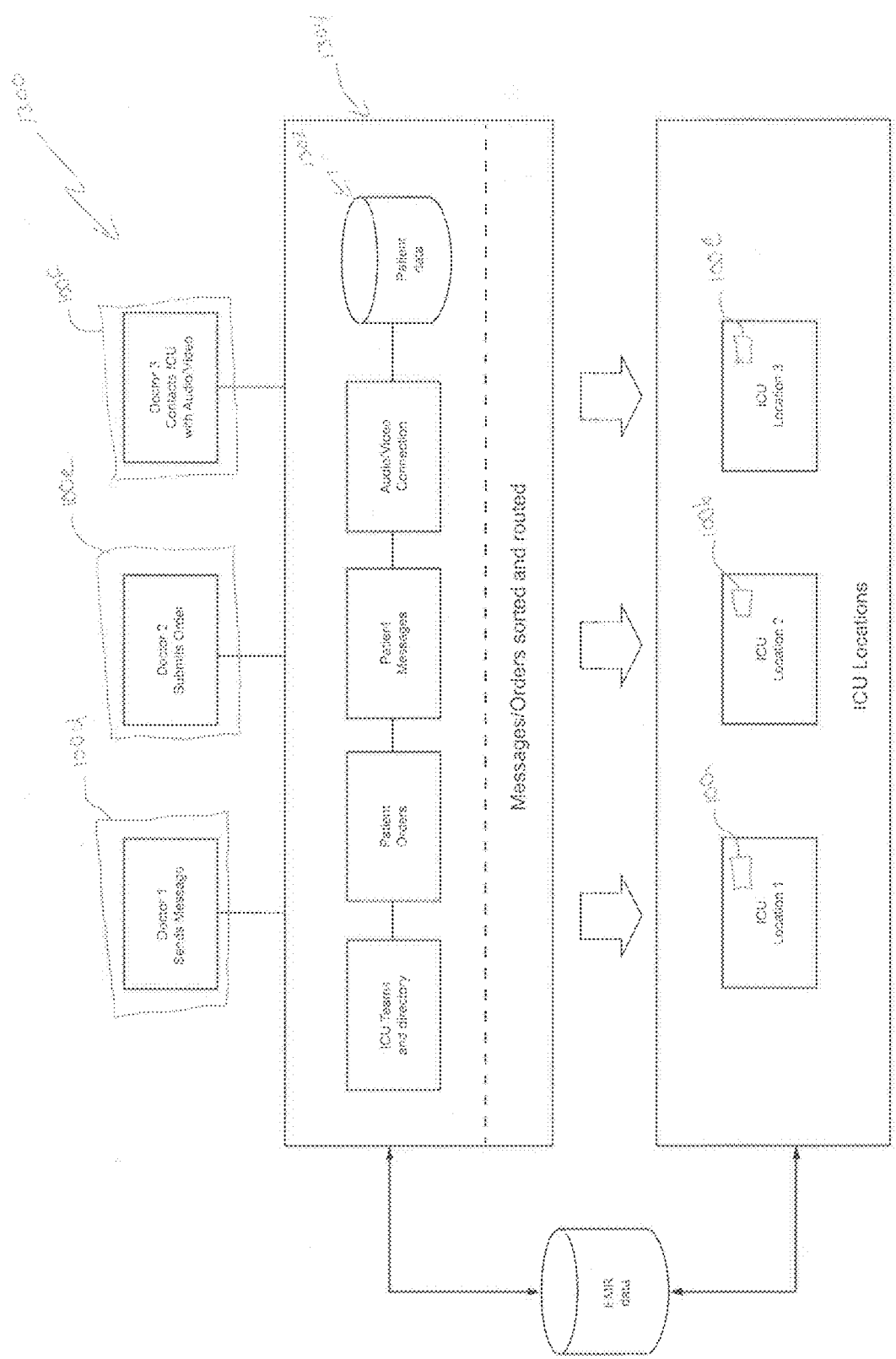
FIG. 13 is a schematic drawing of a system for telemedicine, according to one or more embodiments herein.

In some embodiments, the user interface of the device described above may represent the first screen that is presented to a local medical practitioner, such as a nurse, when they log into the system. The nurse may be presented with a list of patients in their specific hospital unit in a specific hospital. This information may be extracted or received from the hospital's electronic medical record (EMR) and/or admission-discharge-transfer (ADT) database, as shown in and described below, particularly with reference to FIG. 13. Hospital databases contain specific information about a patient including physical location within the hospital, name, gender, and medical record number. This information may be made available through an Electronic Medical Record interface engine. An interface engine may connect systems through industry-specific protocols (e.g., HL7). The role of the interface engine may be to extract, exchange, and/or share electronic health record information between hospital systems. The interface engine may find patients in hospital units electronically by querying a hospital database and, after extracting the desired patient information, may transfer such data to a data repository 1302 (see FIG. 13), such as a database located within the system (see, e.g., FIG. 13) as described herein. The system may then take this information and display it in the format described in FIG. 3 for the user, such as a nurse.

The nurse may have the ability to select patients for self-assignment based on the hospital's practices. More than one bedside provider (e.g., nurse) can assign themselves the care of a patient to enable nurses to take breaks, change shifts, or to balance workload. In some embodiments, once a bedside healthcare provider has selected their patients, the system may display those patients on the left pane list of patient 204 for this bedside healthcare provide, e.g., a nurse. These patients may be only those patients that a bedside healthcare provider has to tend. In some embodiments, a drop-down menu may allow the bedside provider to view all the patients in the hospital unit if required.

In more detail, still referring to FIG. 2, the right pane 208 shows the communications that have occurred in the context of all patients in the hospital unit to which a bedside provider is assigned. When a bedside healthcare provider communicates with a remote provider (e.g., intensivist) in the context of a specific patient, they can select the patient name with either a touch action or a click action, and then compose a broadcast message via the patient specific screen shown in FIG. 3.

Figure 3:
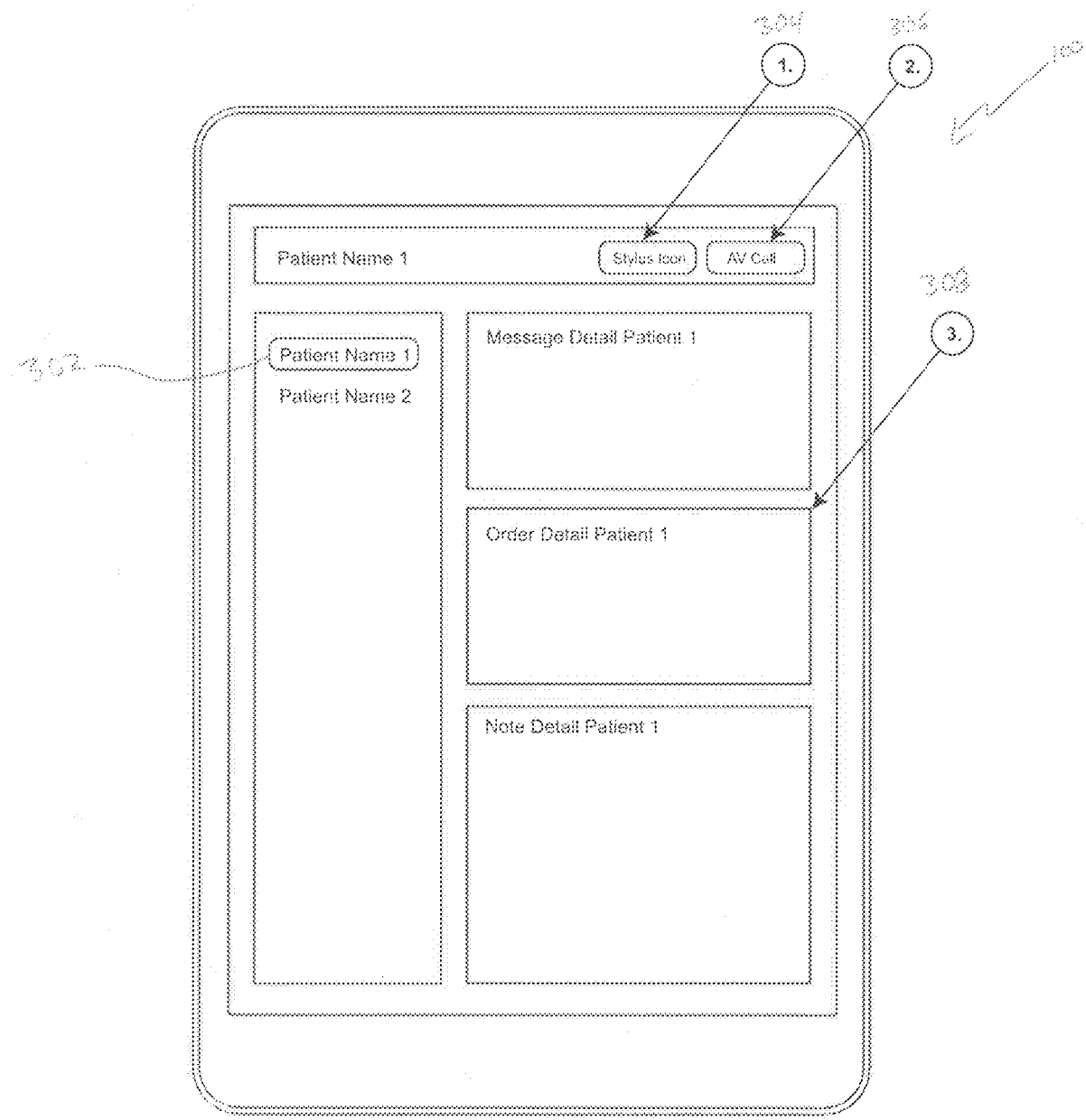
FIG. 3 is a view of the device of FIG. 1 providing a user interface for displaying and receiving information for local medical providers or clinicians, according to one or more embodiments herein.

Referring now to FIG. 3, the device 100 is shown in a message composition configuration. The configuration may include an indication 302 of the patient's name and an interface for communicating status of and information related to the status of the patient. For example, the device may include a stylus input 304 for receiving an input for activating a text or written message composition interface and an AV Call input 306 for receiving an input for activating an audio or video message composition interface for recorded or real-time audio or video messaging. In addition, the device may include an order detail display 308 for a patient which contains detailed instructions for the bedside provider from the remote provider with regards to the patient situation.

Referring now to FIG. 3, when a nurse or other health care practitioner wants to compose a message, the user can interact with the stylus input 304 or the AV Call input 306, for example, by clicking or tapping on one of the inputs 304, 306. The device may receive this input and then activate the appropriate message interface. For example, the composing of the message may be achieved by selecting on the stylus icon 304 on the upper right-hand corner shown in FIG. 3. Composing while inside a patient specific screen may allow communications to occur in the context of a particular patient. In some cases, the messages are sent and/or received in real-time. The messaging system can also provide multimedia messaging that allows digital files to be transmitted, such as photographs or pictures, audio, and video.

Figure 4:
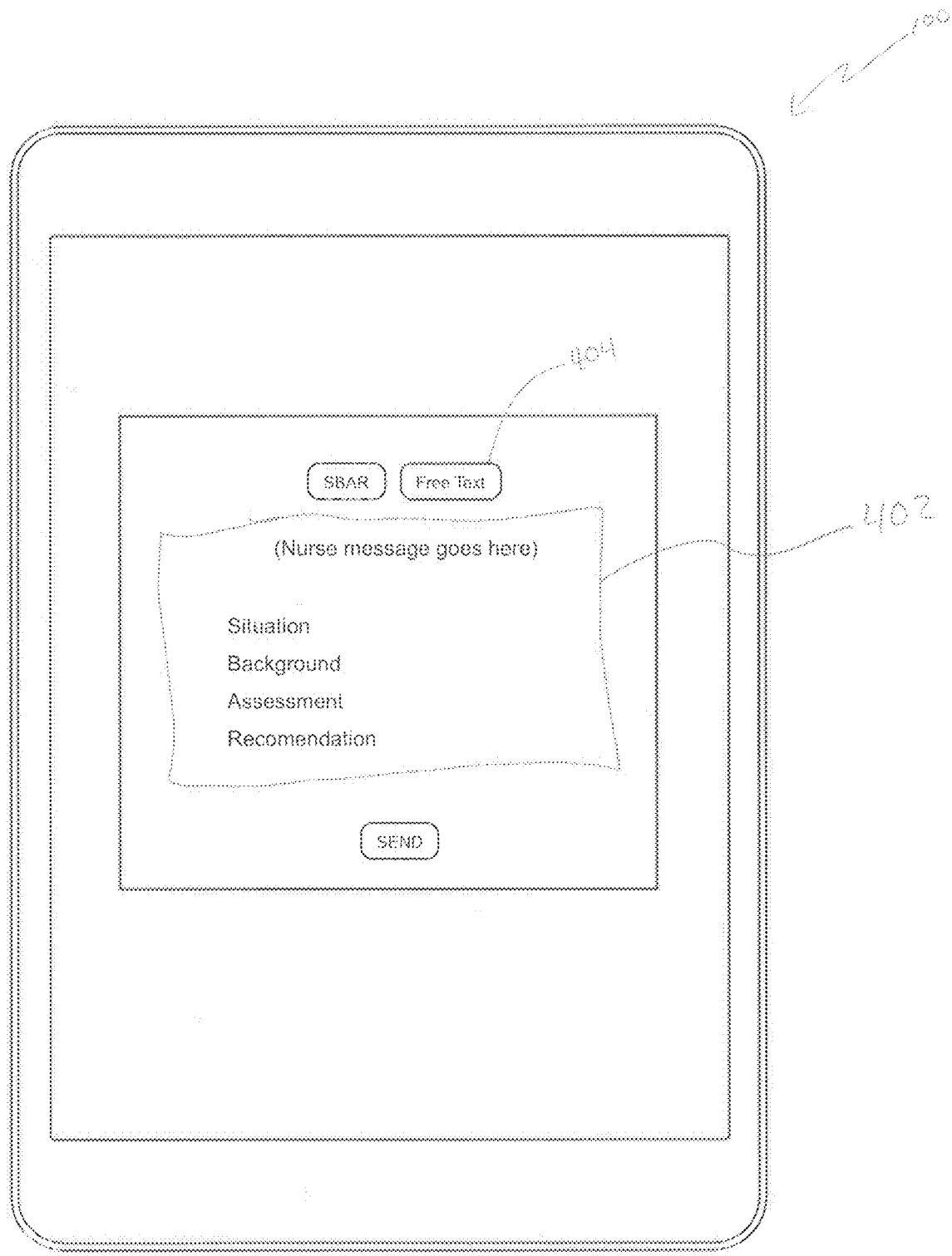
FIG. 4 is a view of the device of FIG. 1 providing a local medical provider's (in this example, a nurse) patient care message to a remote medical provider or clinician, according to one or more embodiments herein.

Referring now to FIG. 4, the device 100 is shown in the message entry state as viewed by local/bedside medical provider such as a nurse. Here the device displays a message 402 composed by a bedside provider in a standardized format with headers permitting the doctor to easily identify the nature of the patient care issue. In some embodiments, a nurse can compose a free-form message for broadcast though a free text input interface accessed through the free text element 404. In some embodiments, the standard format, may be a default or the only interface.

Figure 5:
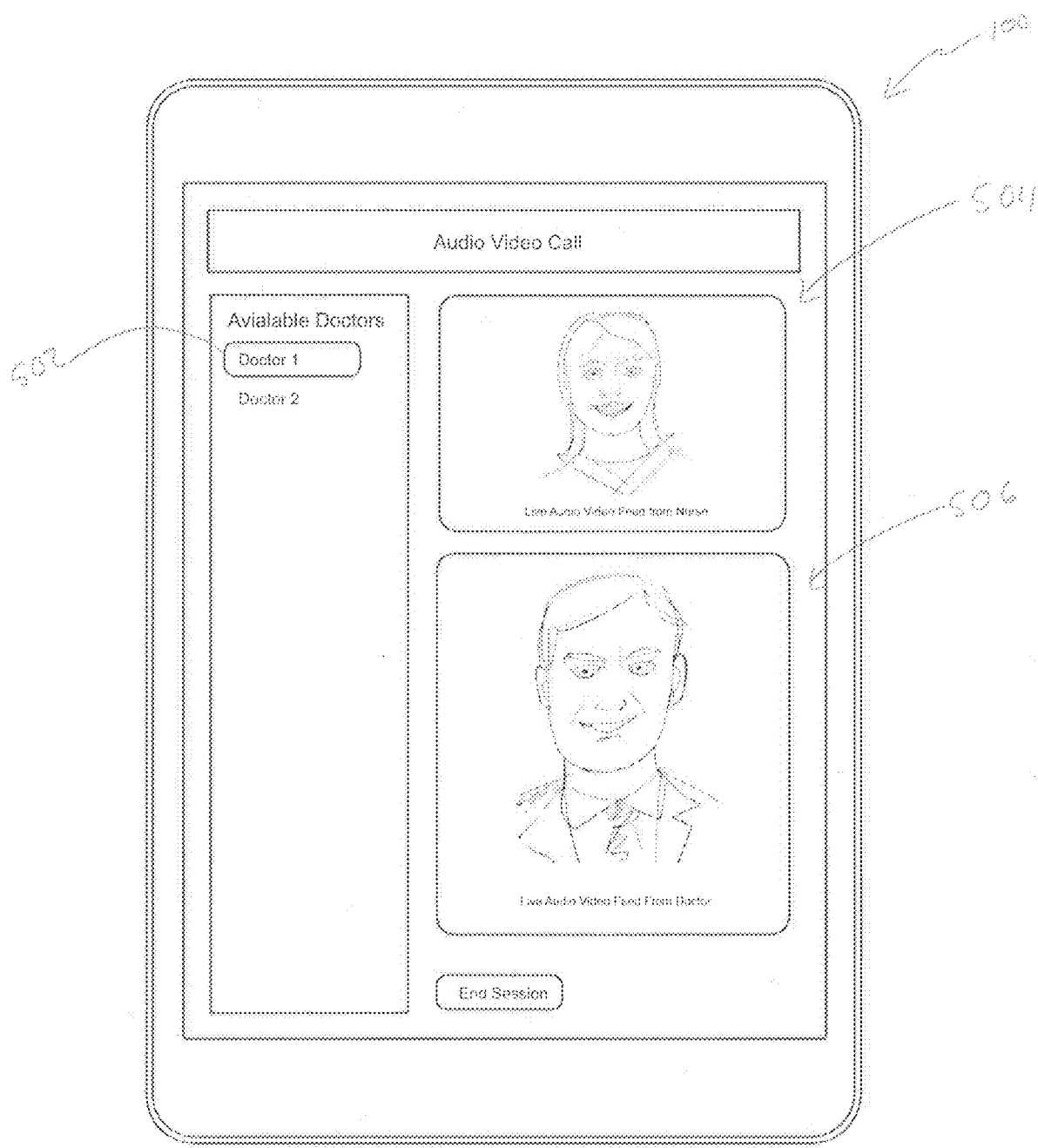
FIG. 5 is a view of the device of FIG. 1 providing real-time communication between remote and local medical providers or clinicians, according to one or more embodiments herein.

Referring now to FIG. 5, the device is shown in the audio-video communication state. On the left side is a list of remote medical providers 502 who might be available for the local medical provider (e.g., bedside healthcare provider) to communicate with using either audio or video calls. On the right side are, for example, the local image (i.e., local to the patient such as a live audio or video feed from a nurse) 504 and remote image (i.e., remote to the patient such as a live audio or video feed from a doctor) 506 that are seen in real time by the parties participating in a video call.

Figure 6:
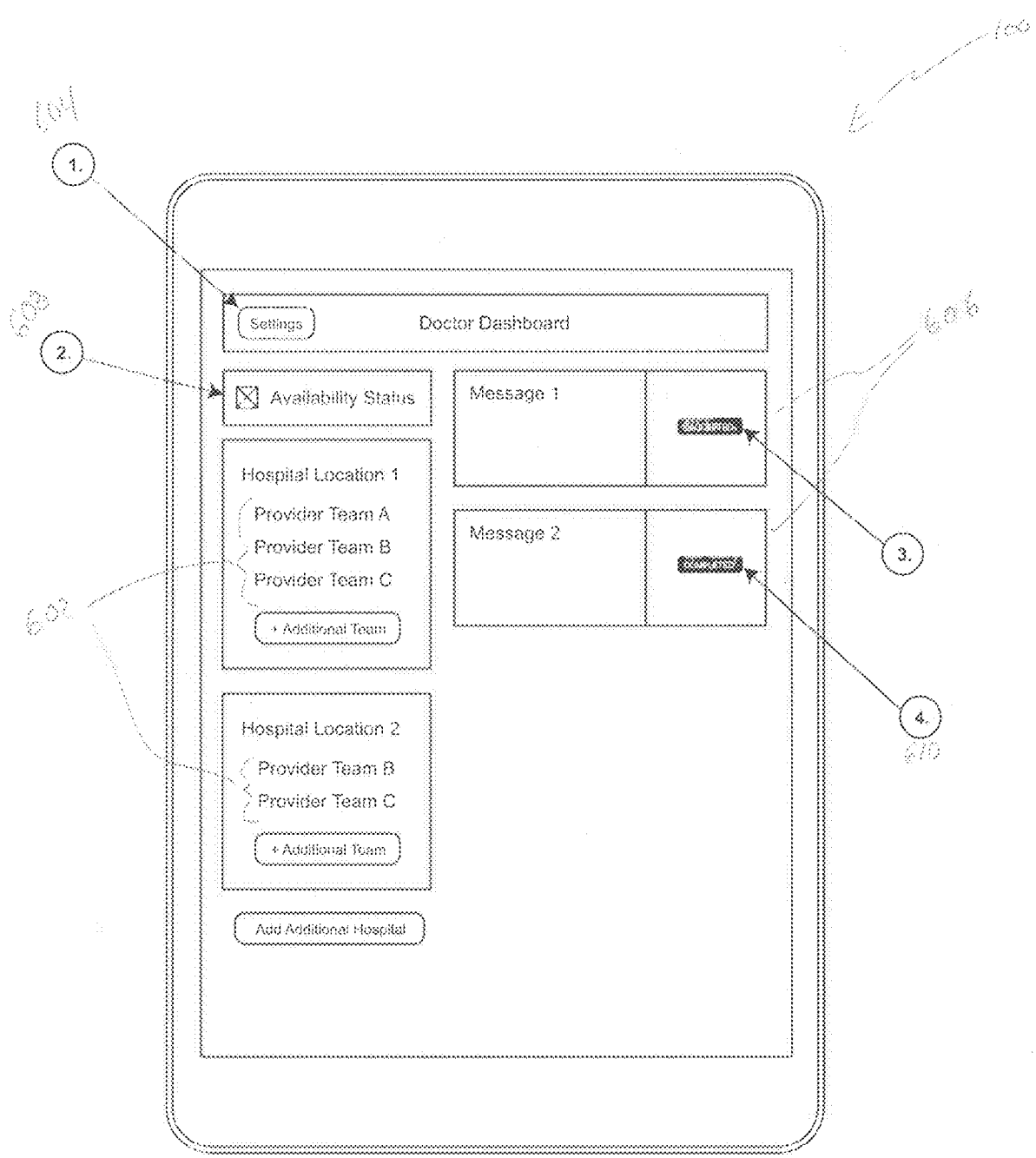
FIG. 6 is a view of the device of FIG. 1 providing a user interface for displaying and receiving information for remote medical providers or clinicians, according to one or more embodiments herein.

Referring now to FIGS. 6 through 9, which show the user interfaces of system 1300 for a remote doctor or physician's assistant, referred to here as the provider. FIG. 6 shows the interface displayed on the device 100 as seen by the provider when they log into the system 1300. A provider may be assigned, either by themselves or by one or more hospitals, to one or more teams 602. Each team 602 may be responsible for a hospital and the unit within that hospital. Therefore, this left side pane may display a list of all the hospital locations and teams that a provider is associated with. For example, Hospital in Location 1, shown in FIG. 6 may have 3 provider teams assigned to it (labelled Team A, Team B and Team C). This will allow the provider to see which hospitals they are interacting with and also other providers (peers) who are concomitantly responding to needs of those hospitals within a team. Since a provider may be associated with multiple hospitals, messages sent from those hospitals can all be displayed for that provider. As shown in FIG. 6, message 1 can be a message from Hospital Location 1 and message 2 can be a message from Hospital Location 2. The right pane may display all of the messages that have been sent by the local medical provider such as a nurse in the context of different patients from different hospitals.

In some embodiments, before connecting to the local or bedside provider such as a clinician or nurse, the remote healthcare provider is able to open the software (mobile app, website, etc.) and view the consultation request. They can then click on the patient's name and see demographic information, chief complaint, and available clinical data. Based on the patient data, the software can automatically calculate a National Early Warning Score (NEWS) and display a corresponding acuity level of low, medium, or high—thus giving the remote provider immediate, high-level context on the patient status. In some cases, to accept the consult, the remote provider can click "Accept" and the local provider is immediately notified that a remote healthcare provider has accepted the consult request. The remote healthcare provider can then click the "Messages" button to enter the app's messaging interface, where communication with the bedside clinician (local provider) can be performed via written messages, audio/visual calls, and/or shared files and images.

Figure 7:
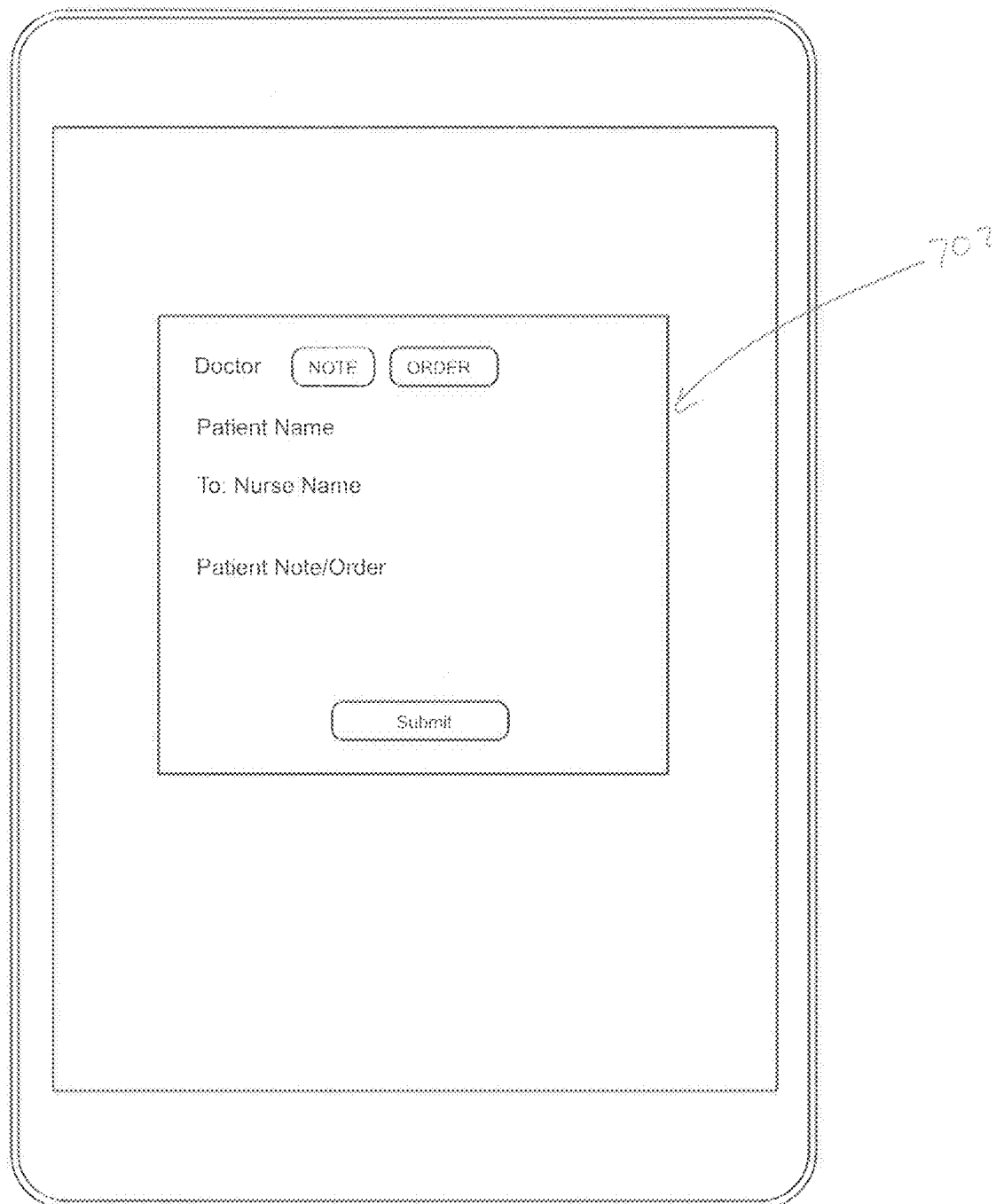
FIG. 7 is a view of the device of FIG. 1 providing a remote medical provider's order or note for a local provider (in this example, a nurse), according to one or more embodiments herein.

FIG. 7 is further detail showing the Order or Note entry state for the interface with the system. This is the interface through which a provider may enter their notes and orders 702 for a patient in response to a message for that patient.

Figure 8:
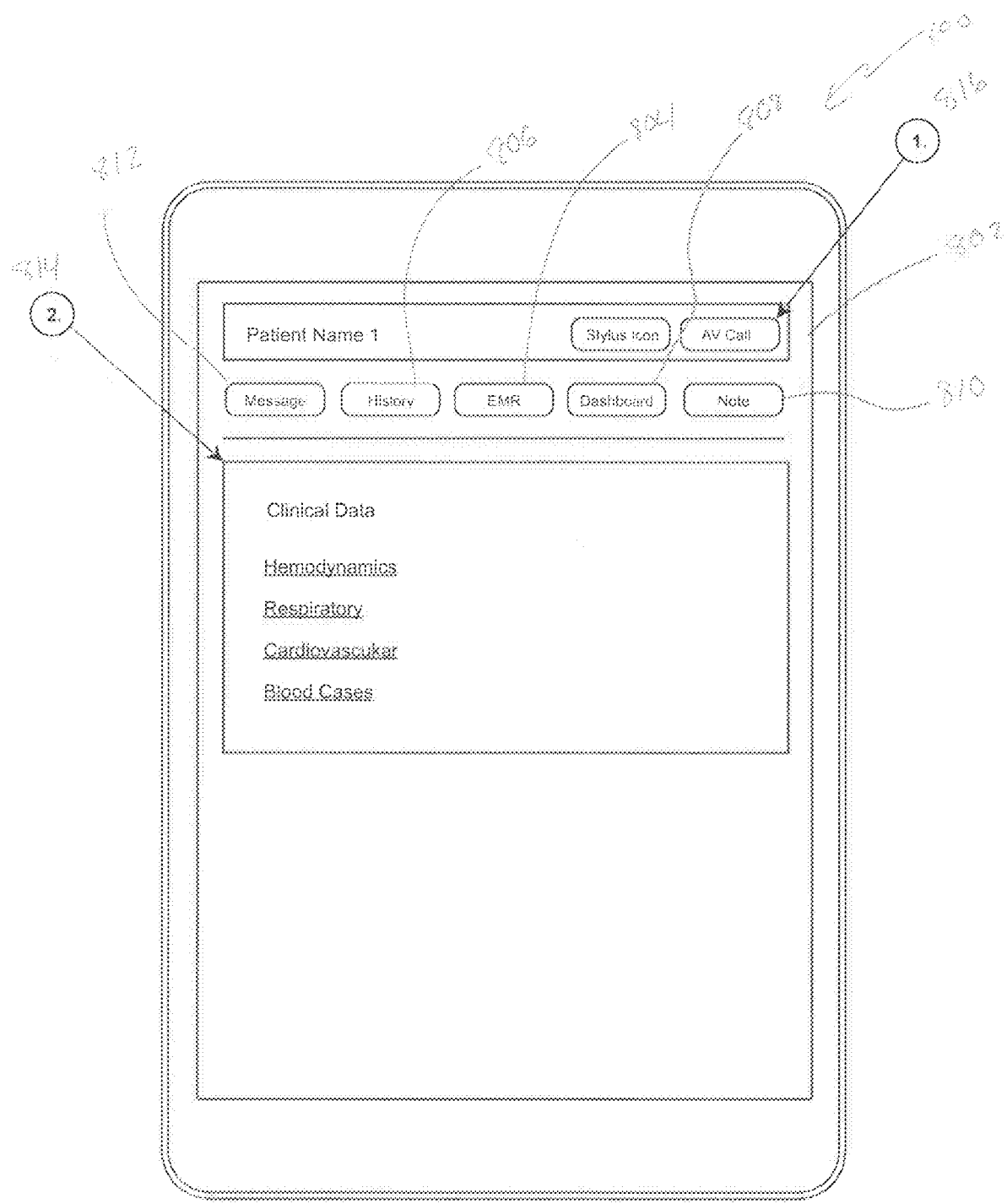
FIG. 8 is a view of the device of FIG. 1 for receiving a patient's medical information, according to one or more embodiments herein.

FIG. 8 shows an individual patient level detail screen 802 showing patient data 804 on the device 100. The clinical data 814 can be organized by systems, such as respiratory, hemodynamics, Cardiovascular and blood cases, as shown. The tab 804 labelled EMR may allow the provider to access medical records, the History tab 806 may show all messages in the context of that particular patient, the Dashboard tab 808 may show further clinical data for a patient, the Notes tab 810 may display notes written by a provider for a patient, and the Message tab 812 may display the messages received in the context of that patient. Additionally, the AV Call input 816 may facilitate an audio or video call between a bedside healthcare provider (or the patient) and a doctor.

Figure 9:
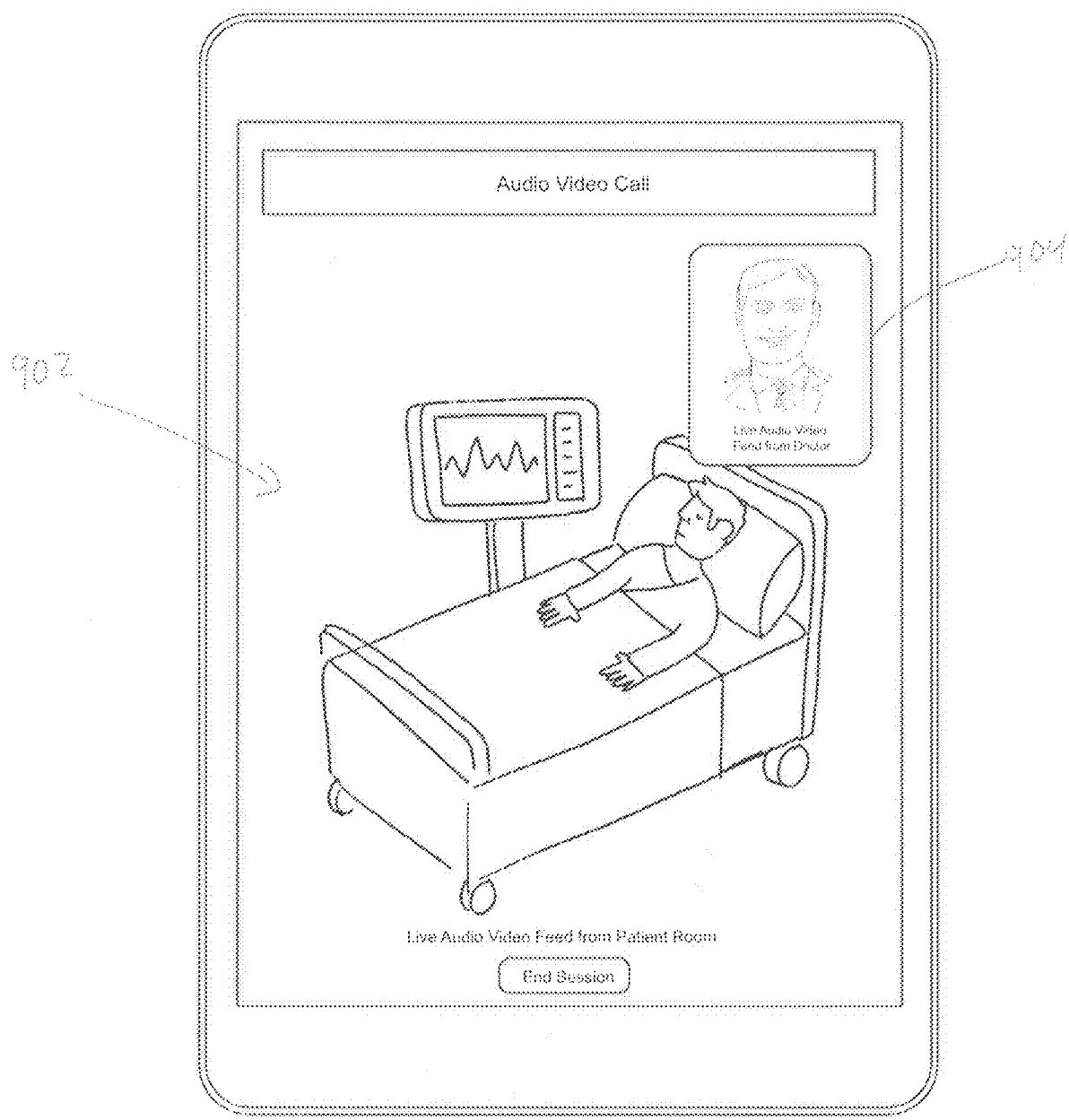
FIG. 9 is a view of the device of FIG. 1 for remote viewing and interaction between a patient and a remote medical provider or clinician, according to one or more embodiments herein.

FIG. 9 shows the device 100 with an interface that includes a live, delayed, or recorded video or image 902 of a patient in their room as visible to the remote provider. The interface can also include a live, delayed, or recorded video or image 904 of a provider. This interface may be accomplished via the interface, or, alternative or additionally, by Virtual Reality (VR) devices.

Figure 11:
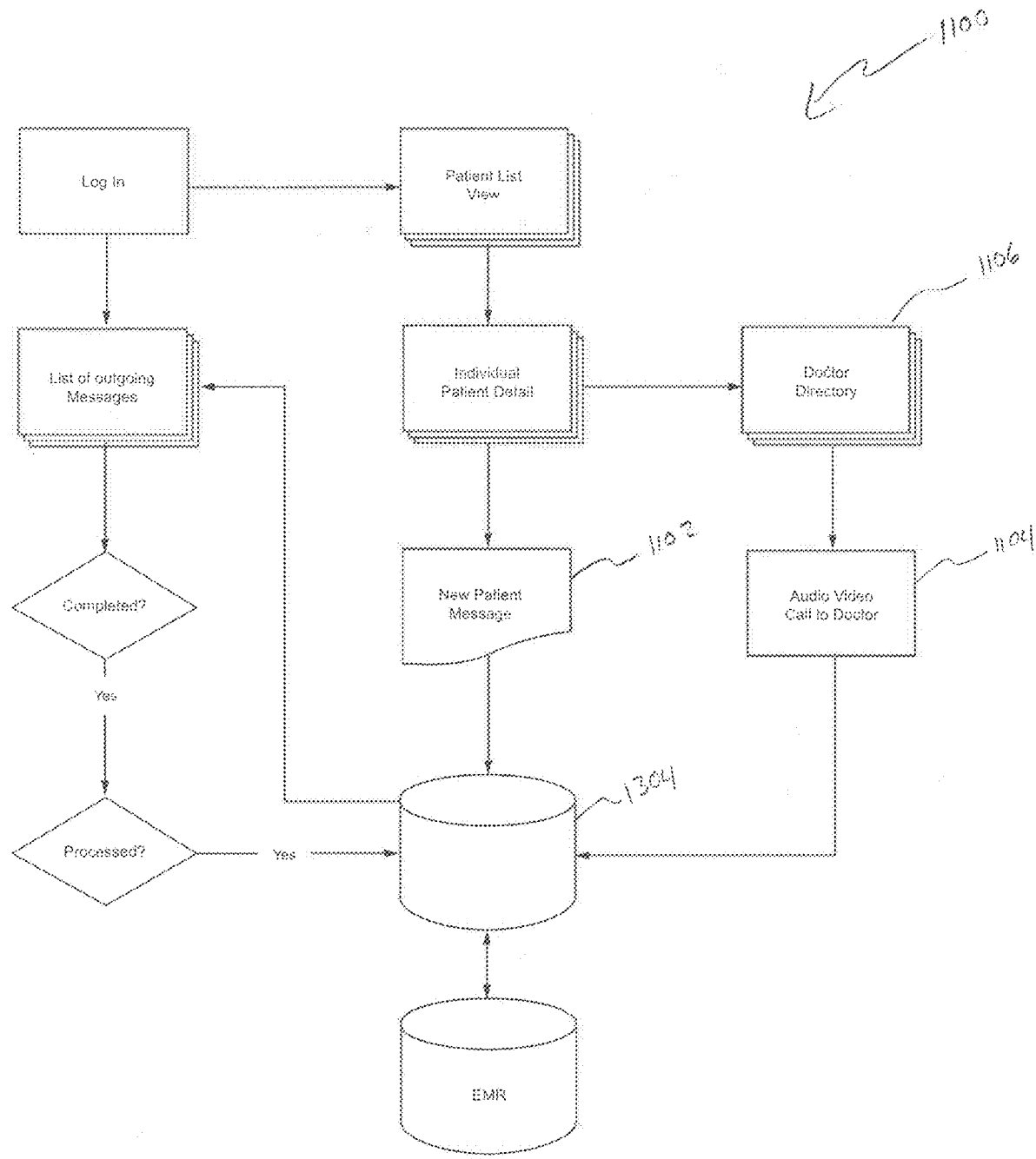
FIG. 11 is a schematic drawing of a process for local telemedicine, according to one or more embodiments herein. As used in this context, messages that are sent and accepted by a healthcare provider refer to consults or requests for consults.

FIG. 11, shows an embodiment of a process 1100 with which a local/bedside medical provider, such as a nurse, may undertake when they wish to communicate with a remote doctor or a physician's assistant. First, the local provider may broadcast a message 1102 in the context of an individual patient through the system which can be viewed on the screen (FIG. 3). The local provider can also see if a message that they have broadcast on behalf of a patient has been "Accepted" for action by a remote doctor or a physician's assistant as shown by indication 218 in FIG. 2. If a message has not been "Accepted" for action by a remote doctor after a particular duration, the bedside provider can choose to broadcast the message again or initiate an audio-video call 1104 with the remote doctor as shown in FIG. 11. Further, the local medical provider can view the list 502 (see FIG. 5) of remote medical providers 1106 associated with a hospital unit and are available. In order to initiate a call, the bedside provider may tap on the remote provider name 502 on the left side and a call (audio or video) may be made between the two parties. The call itself may initiate a screen that shows the information of both parties and may optionally use the front-side cameras of the devices being used for the communication.

Referring to FIG. 2, when a doctor responds to a message or an audio-video call in the context of a nurse, they can write an Order or Note on behalf of that patient through the interface shown in FIG. 7. Once the Order or Note is submitted, the nurse may be notified via an alert about the new Order or Note as seen in FIG. 2 (e.g., via notification field 216), details of which will display as shown in FIG. 3 (e.g., via order detail display 308). The nurse can then act on the Order. If there are further issues to be dealt with regarding the same patient, the nurse may either broadcast a new message or initiate a new audio-video call. All outbound messages, notes and orders pertaining to a particular patient, may be displayed chronologically in the right pane of that patient's screen on the nurse's dashboard as seen in FIG. 3.

Figure 10:
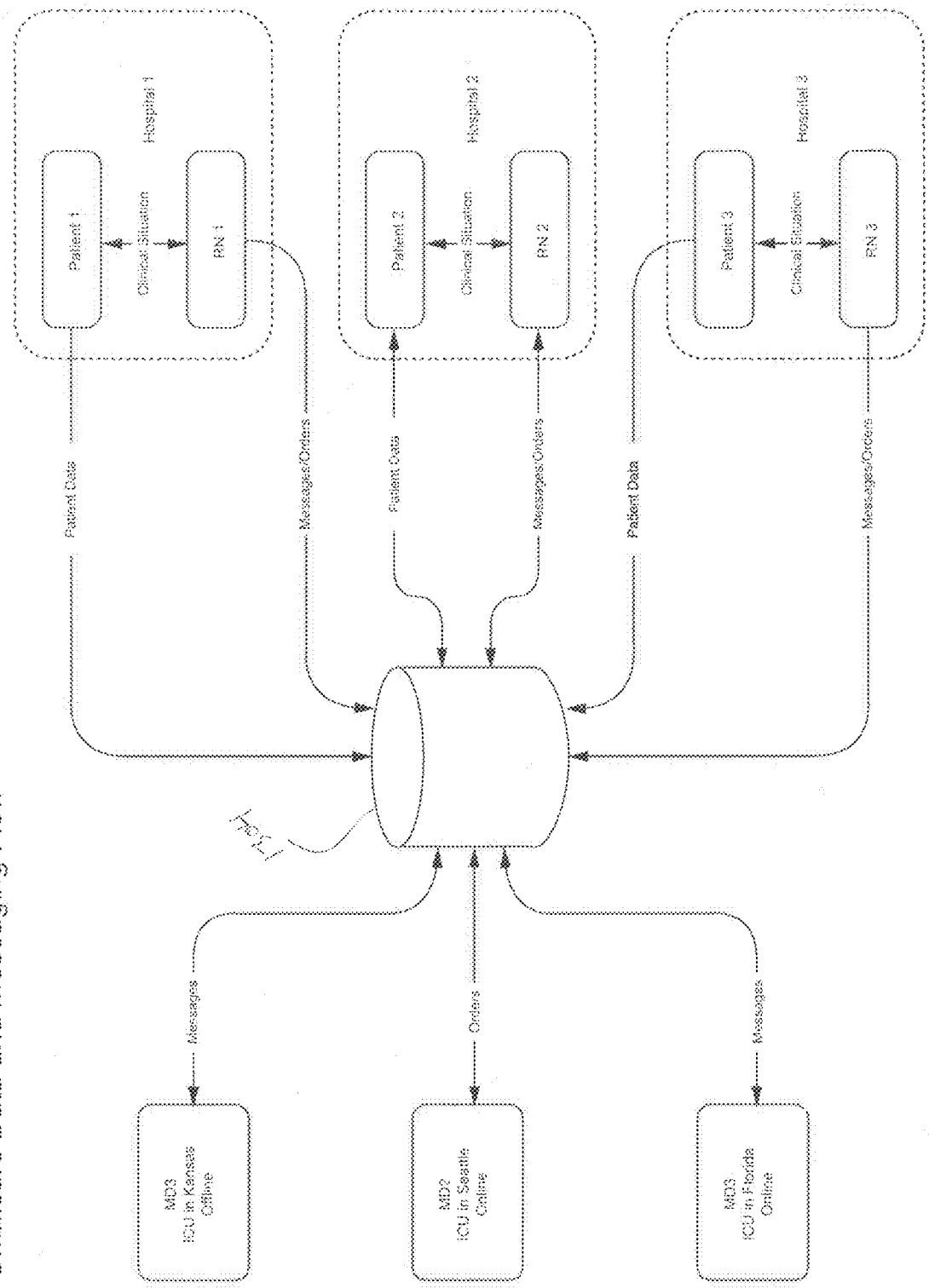
FIG. 10 is a schema of the flow of information between local medical providers and remote medical providers or clinicians, according to one or more embodiments herein.

FIG. 10 describes the flow of information between multiple patient locations and the telemedicine providers. Shown in the figure are 3 hospitals 1, 2 and 3 with a hospitalized patient in each location. RN 1, 2, and 3 refer to the local medical care providers for each patient. As shown in FIG. 10, messages may be sent in response to a clinical situation and are broadcast to multiple available medical providers in different geographic locations (represented by MD 3 in Kanas, MD 2 in Seattle, and MD 3 in Florida). Any of these remote providers who are online may respond to the situation and create an actionable order which is routed back to the originating patient. The remote providers may have access to patient data, which is transmitted via the system 1304, which may be a server. In some embodiments, the transmission may be in real time.

Figure 12:
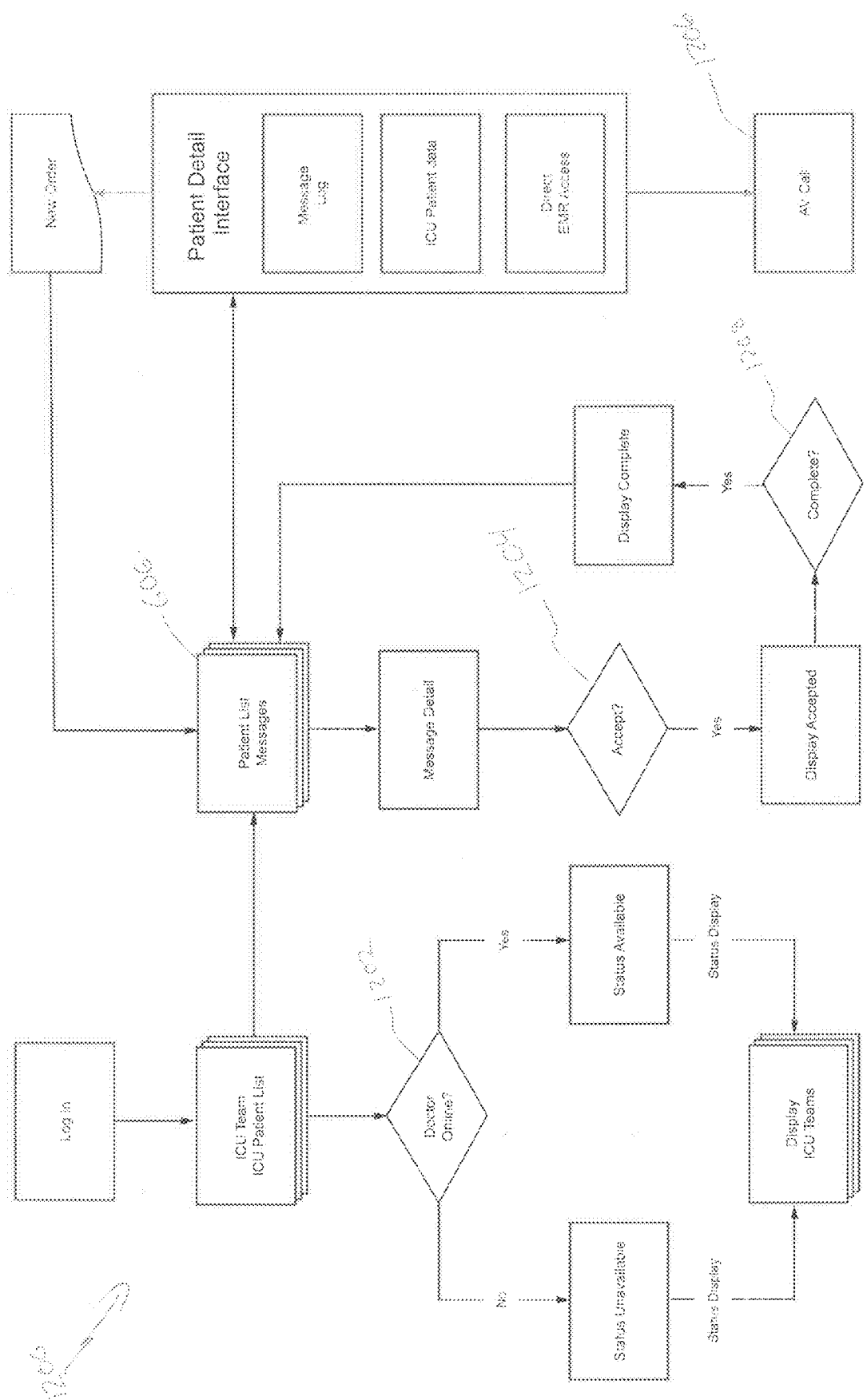
FIG. 12 is a schematic drawing of workflow process for remote telemedicine, according to one or more embodiments herein. As used in this context, messages that are sent and accepted by a healthcare provider refer to consults or requests for consults.

Referring now to FIG. 12, a process 1200 undertaken by the remote medical provider after the log in is shown. Each box in the figure represents a subsequent step in the workflow for a provider. FIG. 12 represents the workflow schema, while the FIGS. 6 and 8 show the state of the system during the workflow. These steps are described in detail in association with relevant figures below.

In some embodiments, an association between a remote provider and a hospital is created on the back end by matching providers to hospitals based on licensing and credentialing at sites. Alternatively, in some cases, remote providers can self-select hospitals by creating associations with one or more hospitals. As an example, after login, a provider can add themselves via the Settings element 604 in FIG. 6 to teams and hospitals that they are affiliated with. The authentication with the hospital to validate the provider as an authorized caregiver may happen in the background via a 2-step process. The provider may receive an email link from the hospital using their standard practice. The provider can then add himself to the hospital that is part of the network of hospitals deploying the system. At that time, another authentication process may be initiated after which a provider may be permitted to use the system via a login process on the device 100. Upon successful login, the provider may be presented with a dashboard as shown in FIG. 6 that shows a complete list of patient related messages 606, broadcast by nurses, as described earlier, regarding the patients that are admitted to a hospital unit that the provider is affiliated with. In some embodiments, the provider may fill in a questionnaire to generate a doctor profile, and the questionnaire may include questions such as specifies, length of practice, etc. In some embodiments, once a provider is successfully added to the respondent list, the system may automatically populate a doctor profile using information from internal database. The provider can set their status 1202 as Available or Offline via the tab 608, shown in FIG. 6. Providers who have set their available status to Available can receive audio-video calls.

Further, a provider can scan through all the messages 606 (messages in this context refer to consults or requests for consult) and choose the one they want to act on by accepting the message in operation 1204 of process 1200, as shown in FIG. 12. Once a message or request for consult has been self-marked as "Accepted" it is the responsibility of that provider to act on that message or consult. The provider can then click on the patient's name in the message detail which will direct him to the patient specific dashboard, as shown in FIG. 8.

Further actions can include an audio-video call 1206 to another provider or bedside nurse by clicking on the video icon 816, as shown in FIG. 8. Once a video call is initiated, the doctor may view the patient using a camera on a client node (e.g., a mobile device), see FIG. 9. Additionally, the provider can view clinical data 814 shown in the right pane in FIG. 8.

Figure 30:
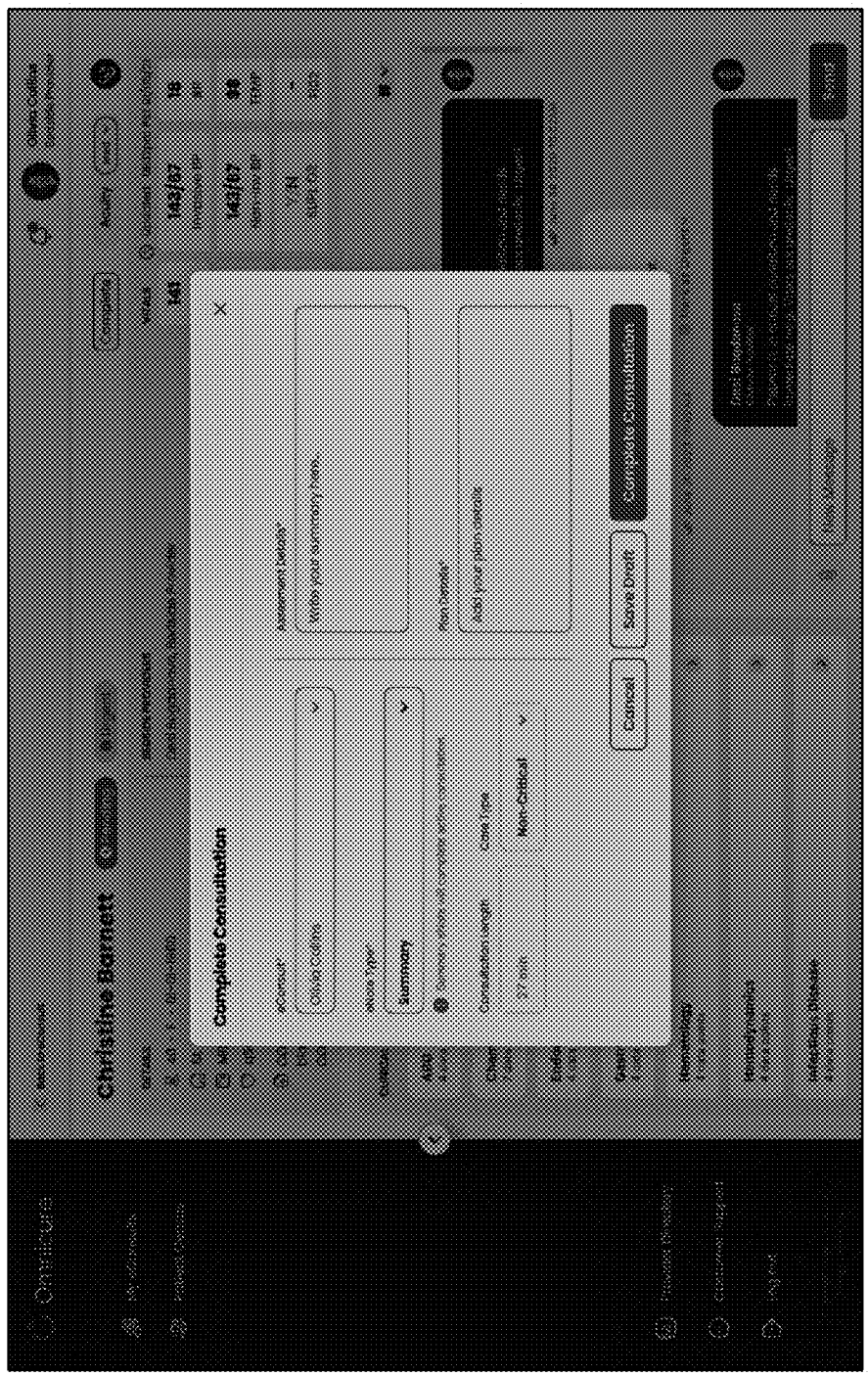
FIG. 30 shows a command center dashboard with a window for completion of a consult by a remote healthcare provider, including notes such as assessment details and plan details for the patient, according to one or more embodiments herein.
Figure 31:
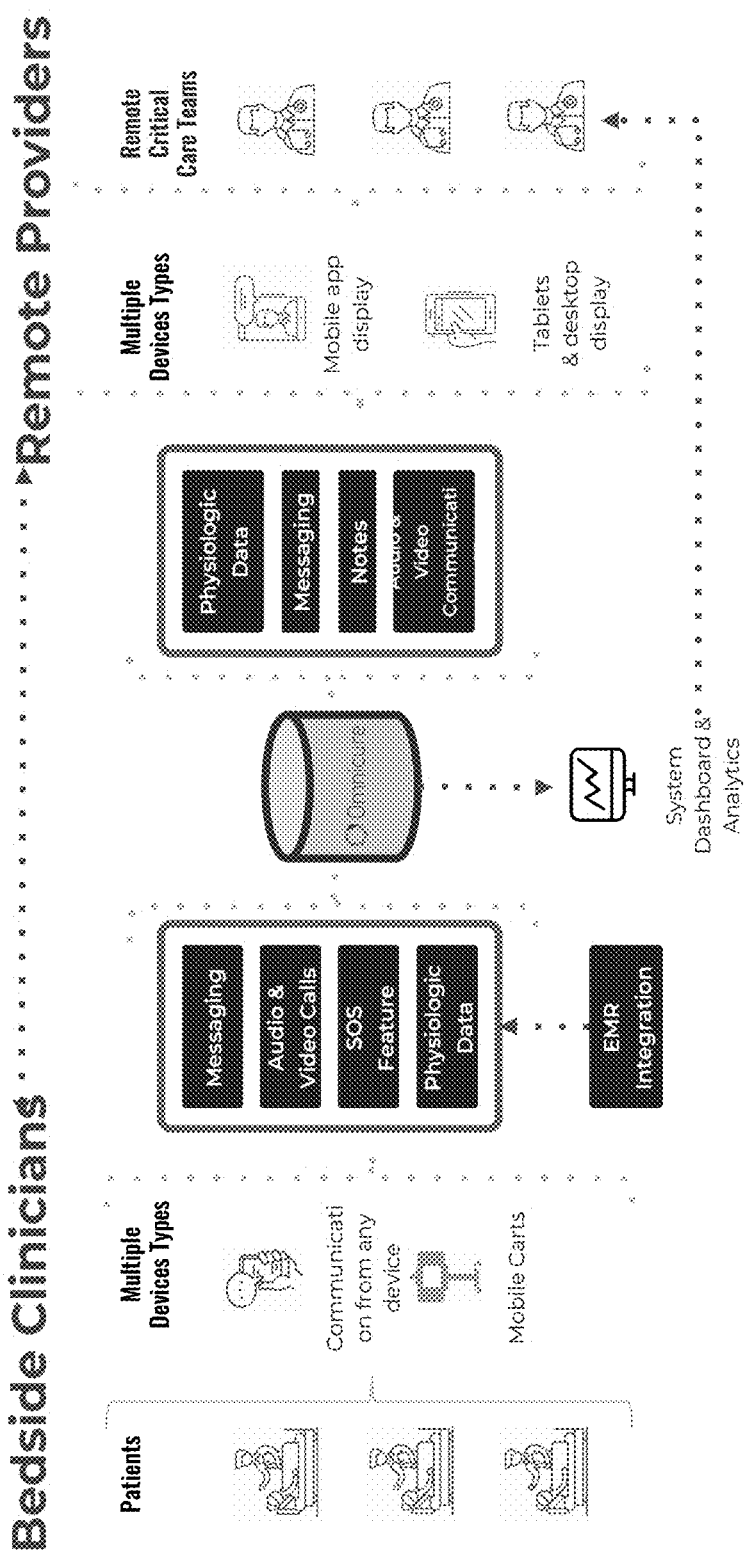
FIG. 31 shows a schematic drawing of a telemedicine system illustrating the relationships between the bedside clinicians and remote healthcare providers and the functionality provided by the telemedicine system to facilitate communications, according to one or more embodiments herein.
Figure 32:
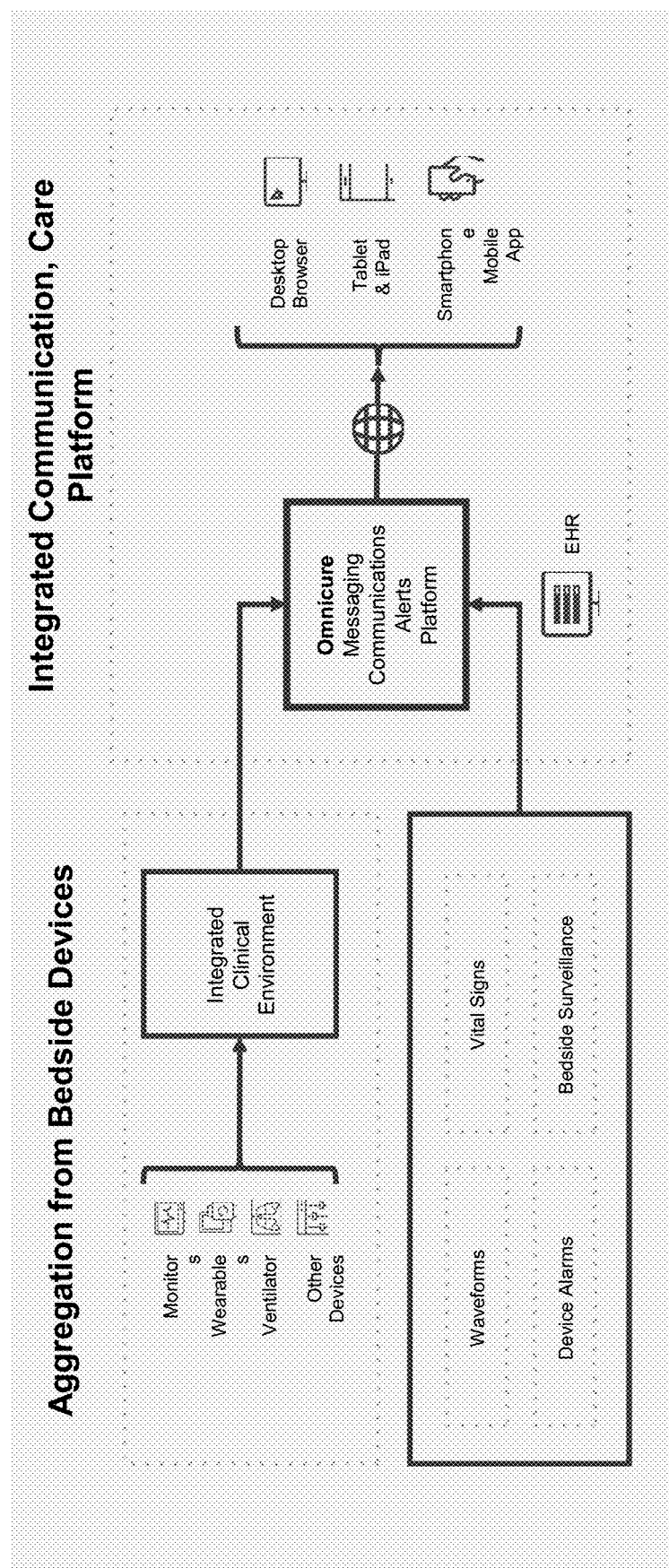
FIG. 32 shows a schematic drawing of an integrated communications platform that aggregates health data from disparate devices to provide enhanced communications for telemedicine, according to one or more embodiments herein.
Figure 34A:
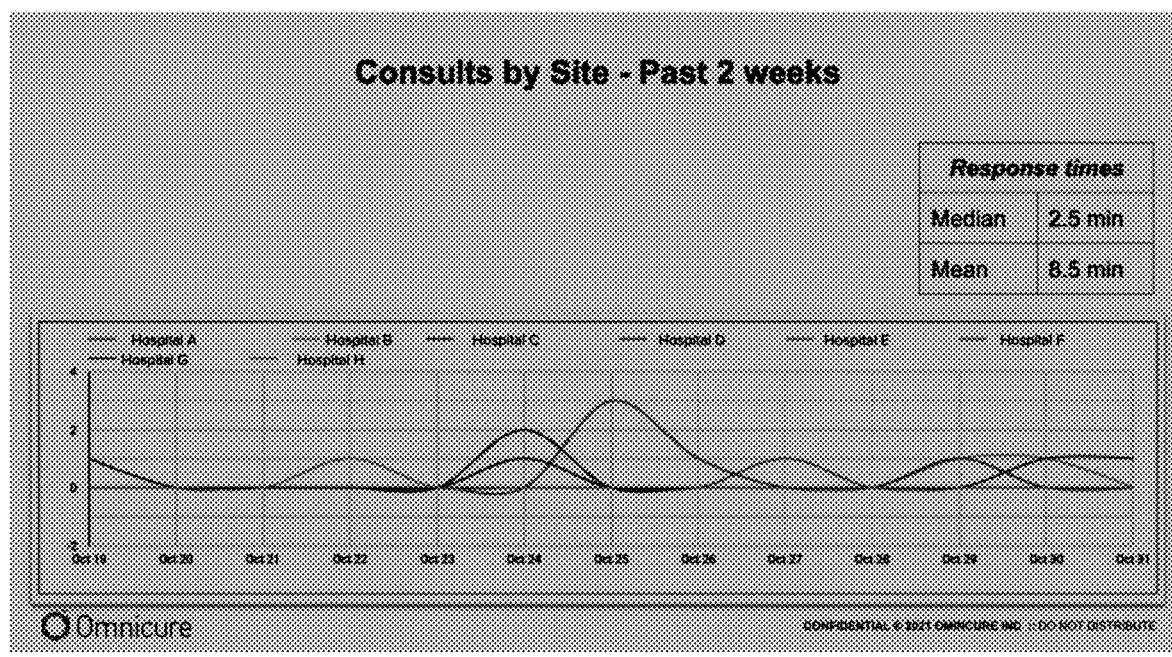
FIG. 34A shows a data analytics chart depicting a timeline of consult response times for different hospitals, according to one or more embodiments herein.
Figure 34B:
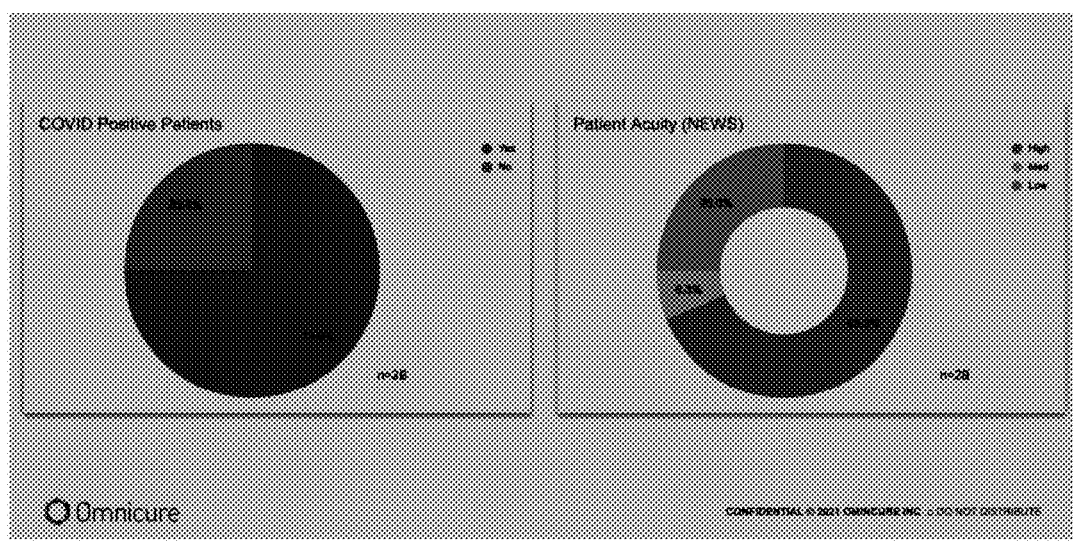
FIG. 34B shows data analytics as part of a customizable patient report including a chart depicting COVID positive patients and a chart depicting patient acuity level, according to one or more embodiments herein.

Once the provider has completed their assessment of the patient, they can write an Order (e.g., medications, lab tests) for that patient (FIG. 7) or a Note (FIG. 7) that documents the provider's recommendations or observations. Orders and notes may be transmitted through secure back-end system 1304 to the patient's permanent health records. In some cases, after the remote healthcare provider supports and advises the bedside user or clinician as needed, and both parties are satisfied that patient issues have been resolved, the remote healthcare provider may complete a summary note with an assessment and plan for the consultation (FIG. 30). The consult will then be marked as complete and automatically removed from the remote healthcare provider's "active" queue to the "complete" queue. The summary note and all exchanged information from the completed consult can be accessed later as needed and is also exported, for example as a PDF, for the hospital to upload into their EMR.

In some embodiments, the platforms, systems, methods, and software disclosed herein comprise a family communications feature allowing real-time communication with one or more third parties such as family or friends. As an example, one or more family members can be added to a virtual team (e.g., team of remote providers providing consult for a patient) to allow them to participate in real-time in the care plan discussions. This is especially relevant in the COVID-19 era in which the patient may be quarantined and outside contact prohibited due to risk of infection. In some embodiments, the local or bedside clinician (i.e., at the client node) can facilitate such communications by sending a text message or email to the family member with a link to join the conversation with the remote provider team.

In operation 1208 of the process 1200, the provider may complete a message as having been acted on via the completed element 610, see FIG. 6. Once a message is completed, it may be removed from the interface such that it is no longer be visible on the user interface for the remote or local provider. However, such messages may be archived and retrieved.

This method of authentication, logging into a system, assigning self to teams or patients, interacting with team members on behalf of patients via messages, orders, notes, and audio-video calls, can be extended to any hospital system or groups of healthcare providers in any part of the world.

The advantages of the present disclosure may include, for example, the ubiquitous ability for healthcare providers to communicate with each other using mobile devices in order to care for any number of hospitalized patients across any number of hospitals in any part of the world. The rich and intuitive user interface allows for streamlined communications that enable efficient and effective patient care in hospital units with the least possibility of errors and clearly audited actions. The use of an integrated software platform that allows communication through messaging, audio-video calls, Orders and Notes, access to patient data securely, from anywhere, anytime on any mobile device, represents a significant advantage and advancement in this field.

In one embodiment, the present disclosure is an effective and economical way to match the limited supply of healthcare providers to the inordinate and growing needs of hospitalized patients all over the world. The use of mobile technology along with unique, intuitive and detailed design and organizational features allows the system to be used across multiple settings in healthcare.

Details of Communication

Communications between local (e.g., nurses) and other remote providers, namely other nurses, physician's assistants, and doctors, may be in the form of messages, audio-video calls, orders, and notes. Messages are a broadcast entity that are initiated by local providers and generated in response to a patient need. They may be composed in real-time using the system and flagged by urgency level which allows remote providers to prioritize their responses. The system may transmit these messages in real-time so they can be viewed by any provider who is simultaneously logged into the application. In some embodiments, messages may be transmitted inside the application/platform. Alternatively, or in combination, messages may be transmitted outside the application/platform environment (e.g., using native text messaging software of the user device). Messages may be formatted to include attachments (e.g., photos, pdfs, etc.). Audio-video calls may be targeted entities and may be initiated by one person to another individual or a group of providers. Often, nurses or other local providers may initiate an audio-video call to communicate directly with a provider to provide further clarity on a situation. The system may use an integrated audio-video system that allows such communications simultaneously. Alternatively, or in combination, the system may facilitate calls using the native calling features of the user device and/or enable calls from the system to a telephone number, or other external system. Orders may be written by remote providers, such as doctors or Physician's Assistants, and can be processed by local providers such as nurses. Orders typically consist of specific instructions to nurses in response to the patient condition as described by the nurse in the message described above. Orders may be processed by the nurses and sent into the hospital medical record to officially record and document the same. Notes may document comments that a doctor or a physician's assistant may wish to add about the patient. Beneficially, these notes may be sent electronically to the hospital medical record to have a clear record of all patient related activity. The messages, orders, and notes may be created with a patient name, location, and identification code by the system. Further, all communication may be tagged with time-stamps to enable any user to have a clear chronology of all activity.

In some embodiments, communications between providers and/or patients may be exportable (e.g., from the app or from an archive thereof). In some embodiments, communications, such as chat communications including photos, text, etc., may be exportable as a PDF. Exporting communications from the app may facilitate record retention and documentation during consultative care, and may make such communications easily incorporable into the patient's EMR.

The systems and methods described herein may provide a more efficient and intuitive Tele Critical Care experience. The system may be configured for synchronous provider to provider (and patient to provider) communication via secure messaging and integrated multi-party audio and video conferencing to enable seamless collaboration and coordination of care on one platform. The system may also facilitate efficient triage based on message levels of urgency and visual cues of acuity, and an SOS feature for emergent situations that require an immediate response. Remote professionals may view messages across multiple sites simultaneously and respond in real-time based on urgency and acuity.

The systems and methods described herein may be agnostic to the device of the user. In some embodiments, the system may be accessible to users on Android devices, iOS devices, or other mobile operating systems. Alternatively, or in combination, the system may be accessible to desktop system running operating systems such as Microsoft Windows, macOS, Linux, or the like.

Figure 14:
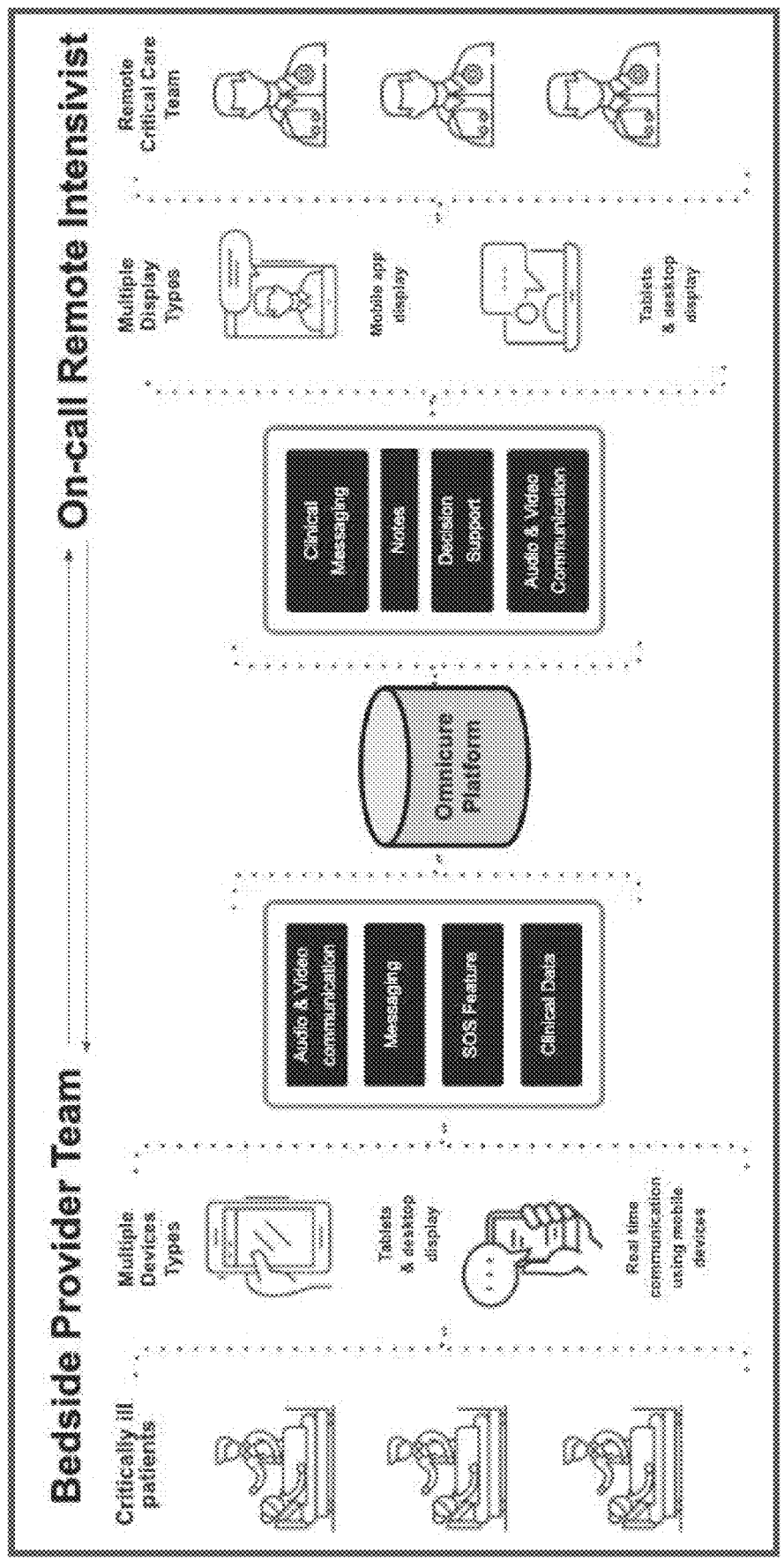
FIG. 14 shows a high-level overview of a telemedicine system, according to one or more embodiments herein.

FIG. 14 shows a high-level overview of a telemedicine system. The system may comprise a cloud-based distributed platform. The system may be configured to connect self-registering patients, bedside providers, and critical care team remote experts and/or provide administrative, triage, and/or data collection oversight functions. The telemedicine app may provide synchronous (voice/video) and asynchronous (text, photo, PDF) communication between mobile devices (e.g., Android and iOS phone and tablet). The app may be downloaded from the respective device's digital store and may provide self-registration for a patient, a local provider caring for the patients, a remote provider caring for a patient, and/or a remote critical care team expert.

In an exemplary scenario, a local viral outbreak (such as COVID-19) cluster may occur in a senior living facility. Bedside providers may access the telemedicine system and register the location as described herein in order to recruit remote providers for help. Remote providers may be called on to help triage the patients as described herein (e.g., via tele-consuls). Some patients may be transferred to the local hospital for treatment while other patients may remain in the senior living facility for care. Bedside providers at the senior living facility may access the telemedicine system to facilitate patient care. In the event that the bedside provider is unfamiliar with the virus, treatment protocols, and/or necessary equipment, training resources may be accessed in the telemedicine app to aid in bringing them up to speed. Teams of bedside and remote providers may be assigned by the telemedicine system as described herein. Patients may be handed off between providers as described herein. Patient vitals, sensor data, etc. may be monitored by the telemedicine system as described herein. The system may be configured to facilitate care even when external communication systems (e.g., internet, telephone, etc.) are down. The telemedicine system may be configured to enable real-time communications between team members in a patient-centric manner. Data may be collected for immediate use (e.g., patient care, remote monitoring by the telemedicine system and/or regional and national authorities) and for later use (e.g., analytics, etc.) as described herein.

Distributed Architecture

Figure 15:
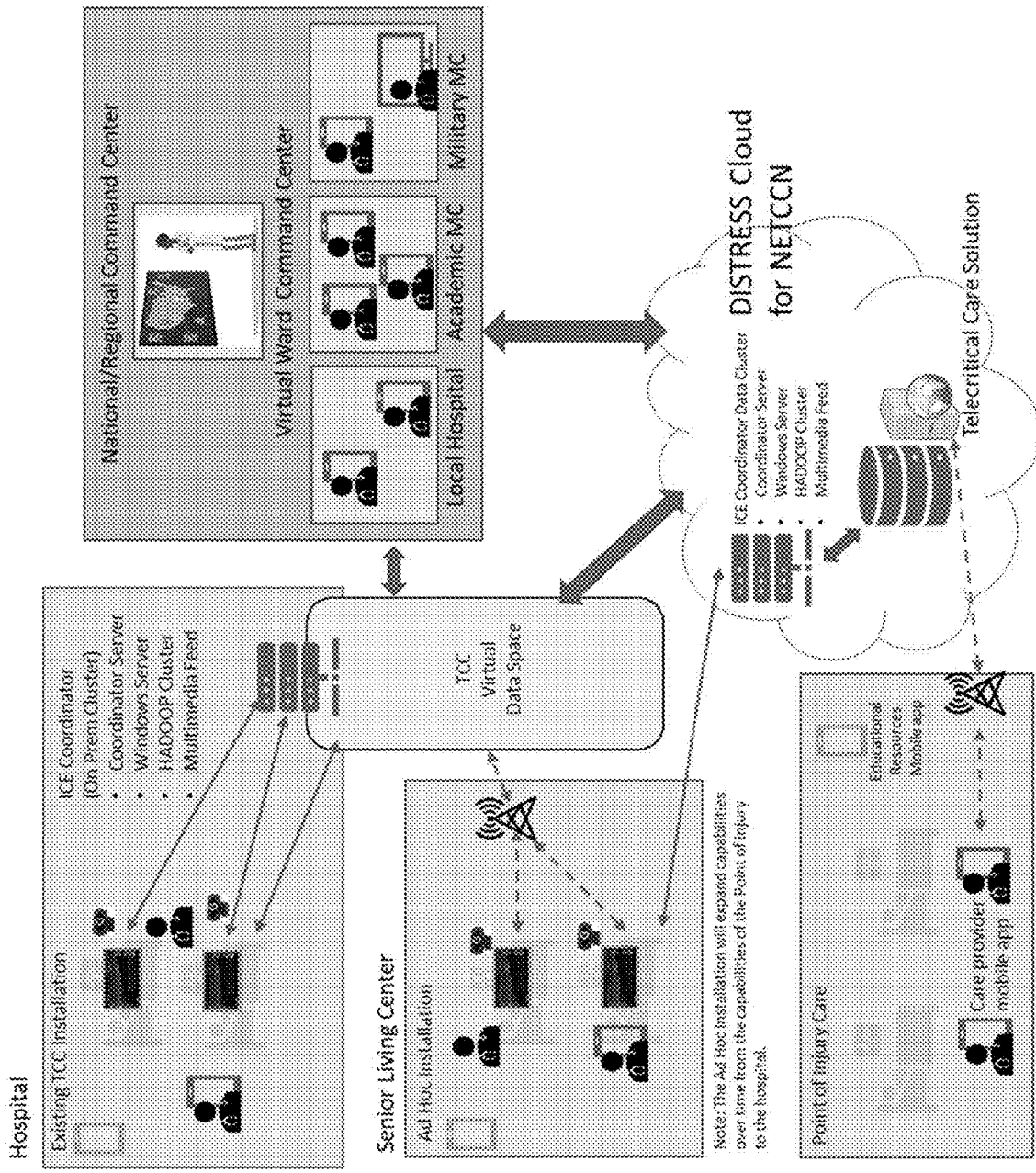
FIG. 15 shows a schematic drawing of a system for telemedicine including a distributed architecture, according to one or more embodiments herein.

FIG. 15 shows a schematic drawing of a system for telemedicine including a distributed architecture. A distributed architecture may be beneficial in that it does not require a large infrastructure and, when needed (e.g., during an emergency), can be created in an ad hoc manner, optionally utilizing highly configurable Internet of Things (IoT) technologies (e.g., for interfacing with medical devices to enable telemonitoring, etc.). The system (e.g., platform and application) may provide a virtual command center role that ensures validation, control, and/or supervision of the response to healthcare support and/or distress calls. Bedside providers and/or first responders may download the app onto smartphone. Bedside providers, first responders, and/or patient proxy (family member for example) can create accounts instantaneously and securely through authentication. The system may provide access to a virtual network of critical care experts using a real-time, dynamic recruiting process. All consults may be visible to the network of specialists and any available specialist may address the request. Alternatively or additionally, only a portion of the remote healthcare providers may be notified with a consult based on the nature of the consult and the specifies associated with the providers (e.g., when there are plenty of healthcare providers are available at a moment). The S.O.S. Feature can notify all available experts simultaneously in an emergency. As medical demand surges, the system may geo-strategically, and incrementally, notify critical care professionals in real-time to provide on-demand care. The system may simultaneously match patients in real-time, using an algorithm based on estimated medical demand, and facilitate dynamic staffing ratios based using artificial intelligence (AI)-based recommended guidelines. Patients who cannot receive timely care by a physician may be transferred to a different provider in the network. Some or all communications within system interface can be uploaded to a hospitals system's EHR through a fast healthcare interoperability resources (FHIR) interface and thus function as a mobile EHR (electronic health record). Care transitions (shift management and handoffs) and patient transports may be managed through the platform as described herein.

The system may be modular and allow for parts of the system functionality to be added and removed as needed. Therefore, the initial capabilities of this system may be rapidly deployable applications, but the system may also have the capabilities to integrate medical device data both directly through the app for some simple sensors or through the medical internet of things (mIoT) platform for more robust data feeds.

Figure 16:
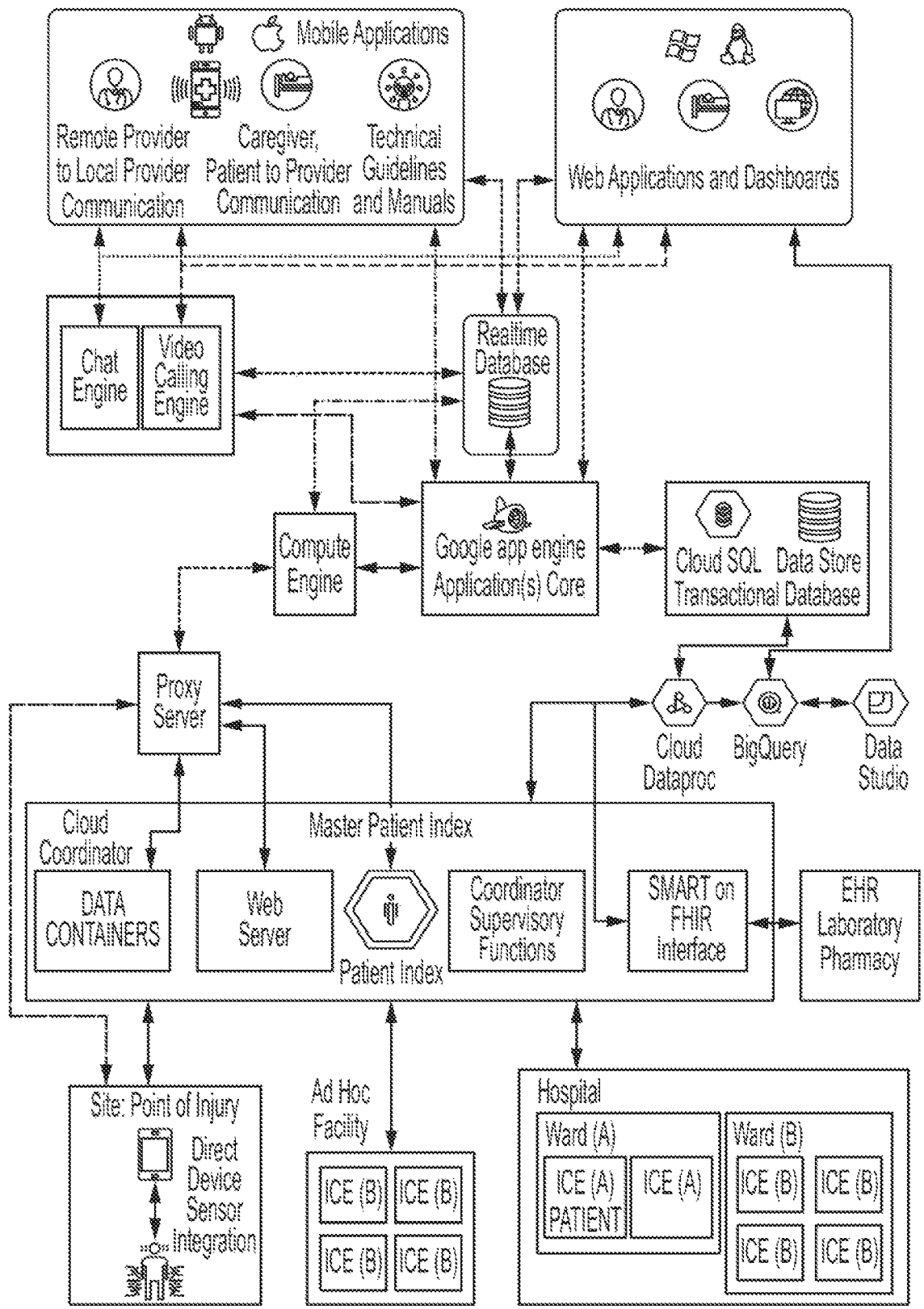
FIG. 16 shows a schematic drawing of the cloud and near patient components of a telemedicine system, according to one or more embodiments herein.

FIG. 16 shows a schematic drawing of the cloud and near patient components of a telemedicine system. This diagram shows the integration that may enable data from the remote and near patient providers to all be aggregated in a common data repository, while feeding the local, national, and regional dashboards. The telemedicine platform may be hosted via cloud-based services (e.g., Google-cloud) which may enable quick approval from federal regulators and/or leverage various big data and AI tools.

Figure 17:
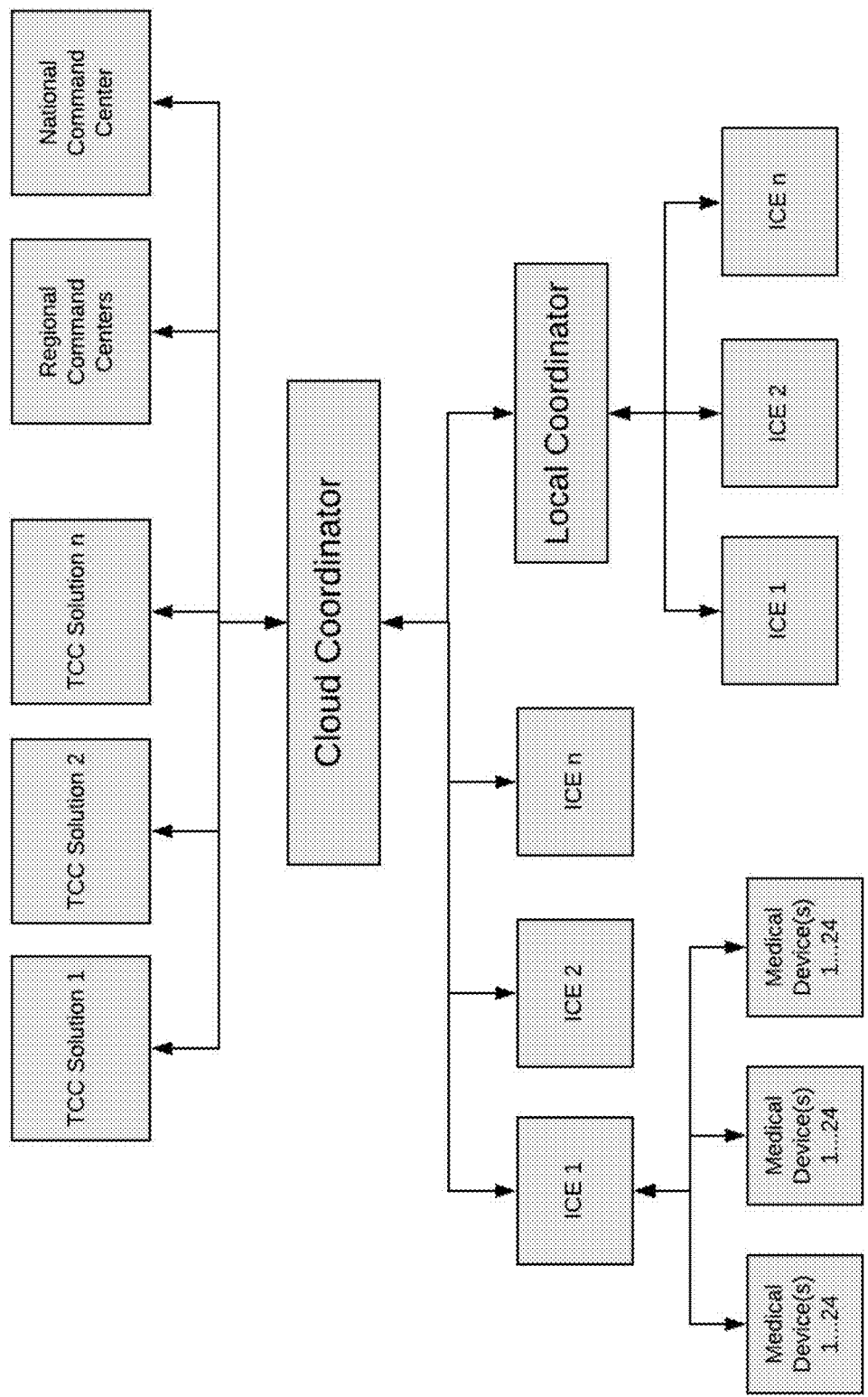
FIG. 17 shows a schematic drawing of a virtual data space connecting various components of the telemedicine system, according to one or more embodiments herein.

FIG. 17 shows a schematic drawing of a virtual data space connecting various components of the telemedicine system. The foundational data infrastructure may enable data from the bedside to be made available to multiple telemedicine (or "tele-critical care") solutions via data distribution through a user's application and a web portal simultaneously for multiple patients. In some embodiments, this infrastructure may enable medical devices from multiple vendors to be integrated simultaneously into the tele-critical care solutions and to situational awareness dashboards simultaneously in near real-time.

The cloud coordinator may enable scalable distribution of data which may enable more flexibility for modular lightweight easily scalable tele-critical care solutions. The cloud coordinator data containers may be categorized in two types. The information and data containers. Information containers may contain predefined and fixed information which may provide the initial starting point to identify data sessions. Data containers may contain streams of specific data sessions for the patient. These data containers may be orchestrated by the webserver to create virtual data sessions, where a virtual ward can be created by combining various data containers. This mechanism may also create a set of situational awareness data containers that would be free of personally identifiable information (PII) or transform the data if real time data is required for situational awareness applications. As the system scales, there more and more data containers for both information and data may be added. It could be imagined that each site has an information data container and the corresponding data containers. Therefore, scaling may come down to expanding the amount of servers in the cloud services, but the flexibility is still available.

As the tele-critical applications form virtual wards, one or more data containers may be dynamically spun up which will represent the patients in this ward. This may enable the tele-critical care applications to only receive the data that they need. Each virtual ward may also create a software defined network protecting the privacy of the patients. As patients move from ward to ward, they may be made available in the necessary data containers. This containerization of the data may also allow the system to transform the data for the situational awareness and operational dashboards without spending PII to these dashboards and make the transmission of data even in limited data settings easier.

Figure 18:
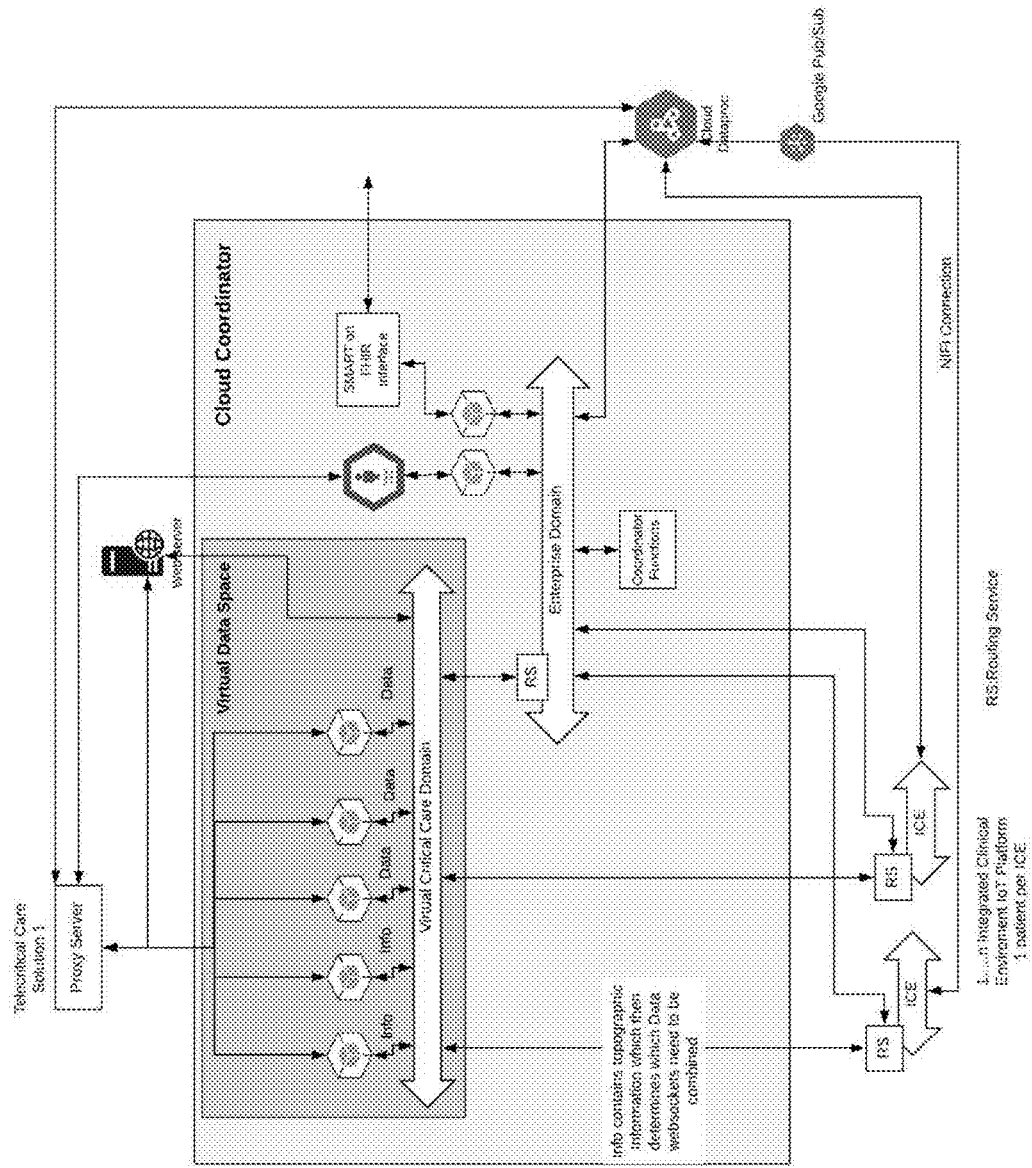
FIG. 18 shows a schematic drawing of a cloud coordinator's capabilities, according to one or more embodiments herein.

FIG. 18 shows a schematic drawing of a cloud coordinator's capabilities. The near patient environment can be as simple as a mobile app which enables video, audio, messaging, to the integration of sensors which communicate via the applications and finally the instantiation of an integrated clinical environment around the patient. The integrated clinical environment may enable the implementation of apps which can communicate with medical devices that are software or hardware which are necessary for the future tasks. In some embodiments, the Command Center Dashboard may be driven by data collected from the mobile applications. In some embodiments, data may be integrated from the integrated clinical environments to provide a robust set of situational awareness data as described herein.

Figure 19:
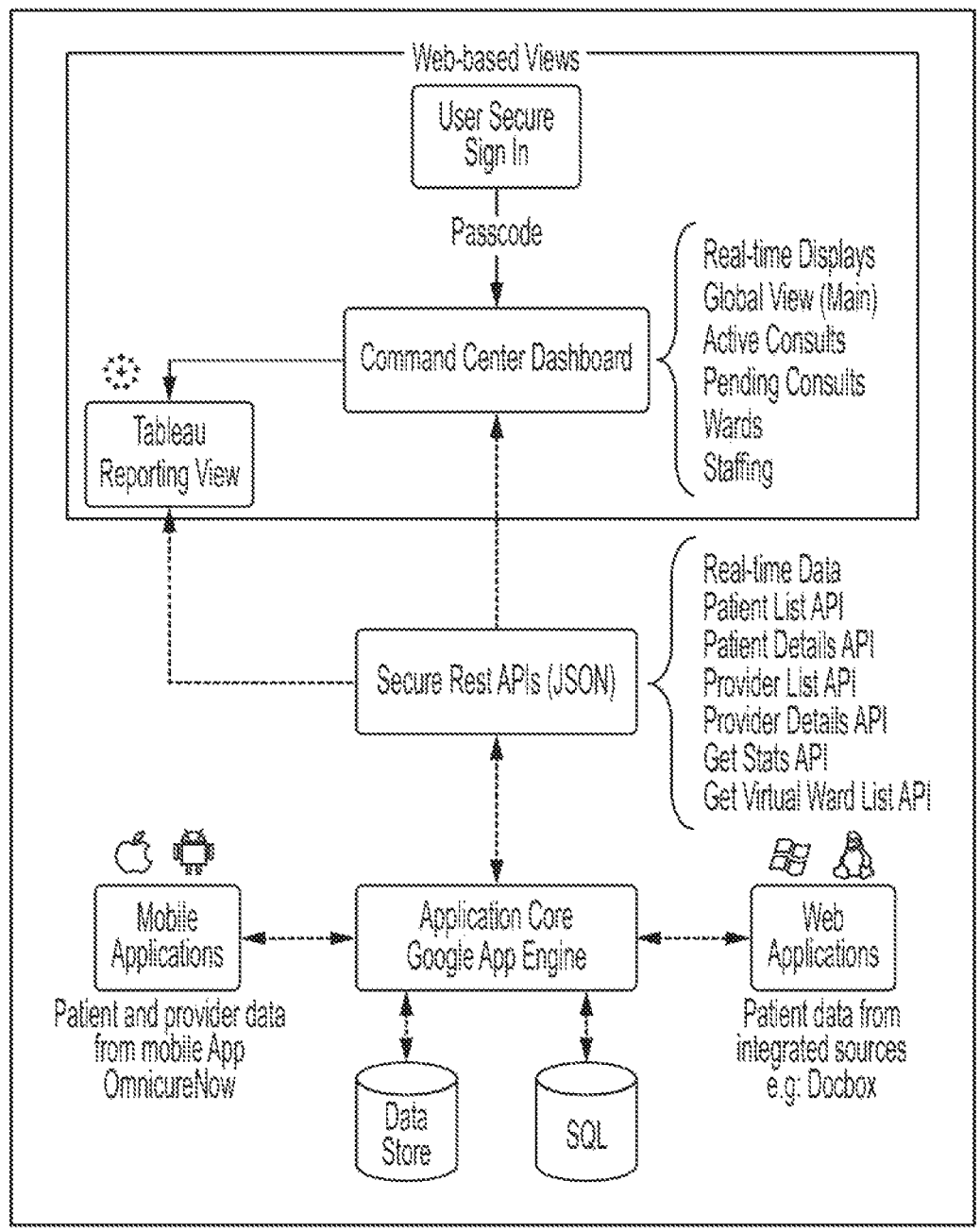
FIG. 19 shows a schematic drawing of a virtual command center, according to one or more embodiments herein.

Virtual Command Center for Monitoring System Clinical Performance and Efficiency FIG. 19 shows a schematic drawing of a virtual command center. The system may include a medical interne of things (mIoT) infrastructure that enables the ability for real-time data collection from each bedside. This infrastructure, which may optionally follow an Integrated Clinical Environment Architecture standard (AAMI 2700), may enable for both real-time data but also the capabilities to aggregate medical device data as well as clinical transactions. The platform also may allow for applications to be hosted in a distributed way while enabling data to be available in the cloud. This may enable a highly modular flexible system and enables an interoperable multi-vendor solution. This robust data infrastructure may enable a Virtual Command Center (VCC), which is a web-based command and control center facilitating the functions of triage, oversight, staffing, real time data collection and analysis.

Figure 20:
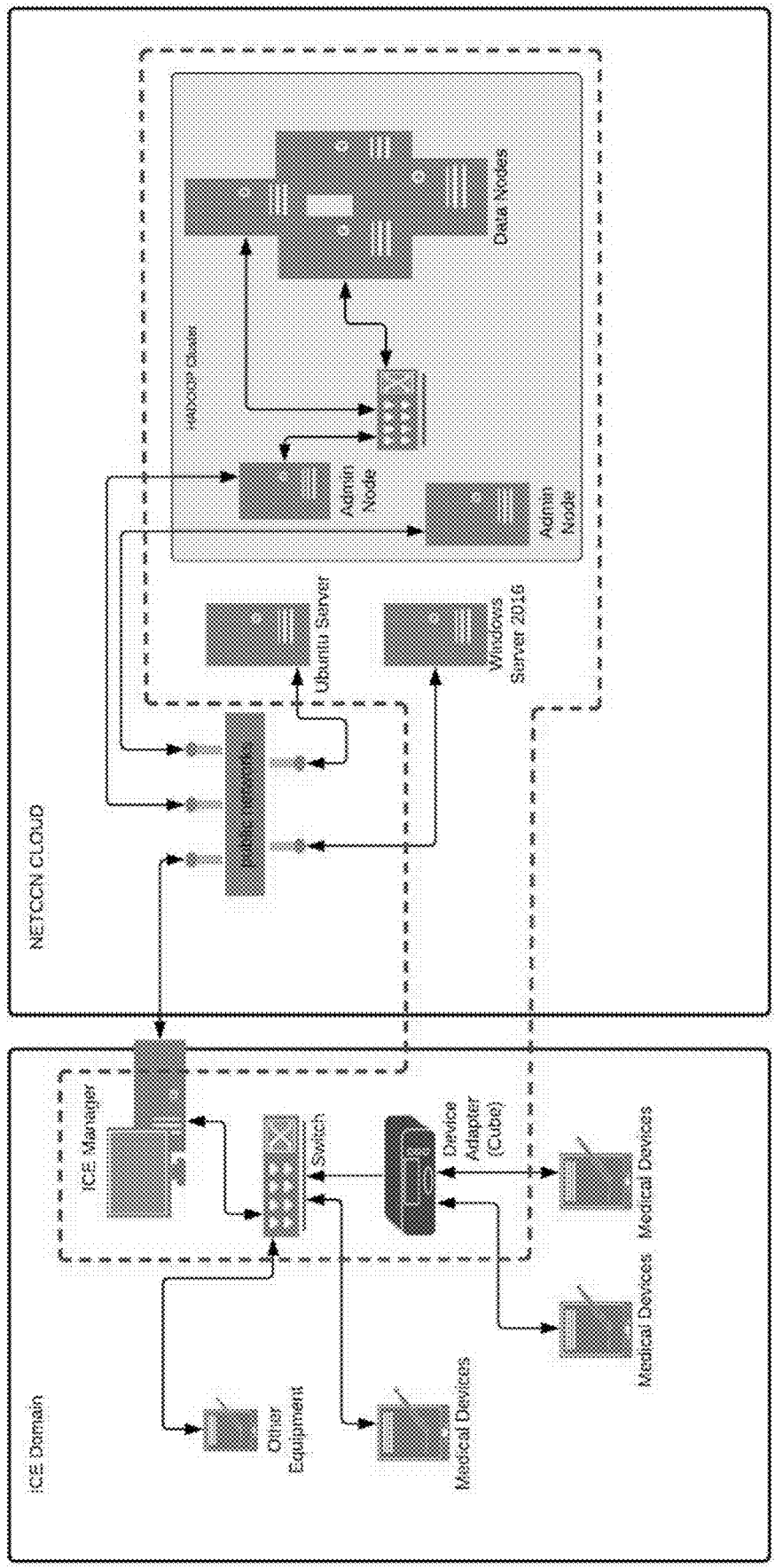
FIG. 20 shows a schematic drawing of physical components of a telemedicine system, according to one or more embodiments herein.

FIG. 20 shows a schematic drawing of physical components of a telemedicine system. FIG. 20 shows the physical layout of the cloud and distributed ICE architecture.

Figure 21:
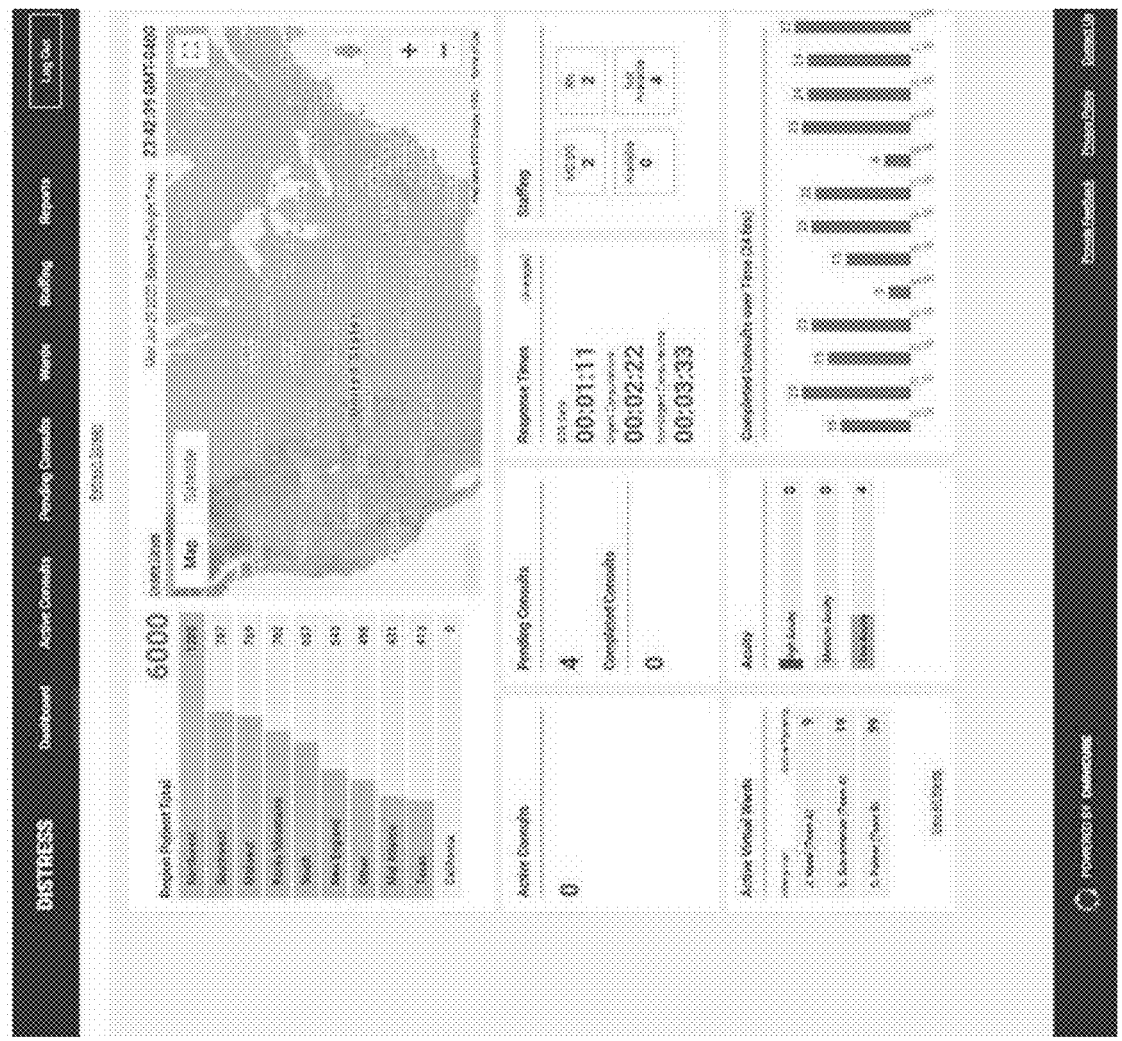
FIG. 21 shows a view of a user interface for a command center dashboard, according to one or more embodiments herein.

FIG. 21 shows a view of a user interface for a command center dashboard. The system may include hierarchical levels of administrative and data functionality. In some embodiments, there may be three levels—Local/Facility, Regional, and National. Level relevant data may be selected to populate dashboards facilitating level appropriate situational awareness. For instance, individual device data (e.g., model of ventilator) may be collected at the end user level and may be visible at a regional and national level to assist in the distribution of equipment and logistical support. Patient acuity may be visible at the local level down to the granularity of individual vital signs to facilitate individual patient care. At the regional level, this data may be summarized with acuity scores to identify hot spots and assist with recruiting critical care staff and ensuring the system is fully capable. This patient level data may be further summarized into incidence, prevalence, and mortality rate at the national level for situational awareness.

In some embodiments, an administrator at the regional level may look up an aggregated numbers (e.g., number of requested consults, number of in-hospital patients, number of medical devices in use, number of available healthcare providers, etc.) at individual sub region or hospital. In some embodiments, an administrator may request to view patient-level data, such as vital signs, lab results, etc. As described elsewhere herein, the telemedicine platform may store patient data at the patient level in the database, and aggregate patient data for display. In some embodiments, the aggregation is performed in real-time or near real-time, i.e., when there is available new data, the platform performs an aggregation in respond to receiving this new data. When the number of participating hospitals increases, aggregation of data becomes a time-consuming task for the platform, and may slow down the platform. To overcome this, in some embodiments, the aggregation may be set to happen periodically, e.g., every 30 minutes, 20 minutes, 10 minutes, 5 minutes, one hours, two hours, three hours, etc. The aggregated value may be displayed with a timestamp of the aggregation next to it. In some embodiments, the user may have an option to force the platform to perform a real-time data aggregation, e.g., by refreshing a webpage or mobile app page. This may allow a user to pull the latest aggregated data by perform a real-time or near-real time aggregation. This mechanism may ensure the users access to the latest data, but if there are no users requesting the latest data, then the system aggregates data in a periodically manner to save bandwidth.

FIG. 21 shows an exemplary dashboard for a Virtual Command Center. The virtual command center may be a web-based dashboard style portal, which may be configured to receive and display data in real-time from all patients, bedside providers, and/or remote providers. There may be several distinct types of users of the Virtual Command Center (VCC): clinical administrators (e.g., director(s) of clinical operations at local/regional/national levels), administrators responsible for resource and infrastructure management, and technology (IT) professionals. The VCC data display may be organized into 4 major domains: Patient Organization, Staffing, Clinical Operational Metrics, and Resource Utilization.

Patient Organization: The Patient organization domain may display real-time information about pending and active consults. This information may include geographical location (e.g., national, regional, state, hospital/ward), and/or patient census for those tiers of location. Patient data can be scaled and sorted by location (multiple tiers), acuity, urgency of the call, and elapsed time since posting of consult. Users may find this view particularly useful to quickly identify the magnitude and location of a disaster situation, with further fine-tuning of the information based on sorting functions.

Data may also be displayed according to a list of all Virtual Wards. For each Virtual Ward, individual patient information may be provided, including acuity and geographic distribution (e.g., a virtual ward may be one place, or may be a distributed set of locations). Virtual Wards can be grouped together based on teams or providers assigned to care for them.

Staffing: The Staffing section may display information on individual remote professionals, their availability, and workload measured by the number of active consults. The team section may show the teams. For each team, all members of this group (intensivists, advanced practitioners, nurses, pharmacists, respiratory therapist) may be listed. Also, their workload, as measured by the number of active consults, may be shown. Both Staffing and Teams views may allow the director to see in real-time the availability of remote professionals and provides insights on how much the system is stressed by comparing the workloads of individual remote professionals and the virtual teams.

Clinical Operational Metrics: The Clinical Operational Metrics domain may allow direct feedback on important parameters relevant to patient and provider interactions. Examples of operation metrics include information on average response times (e.g., to identify lags and potential areas of system stress), healthcare providers capacities, and time trends of patient volume moving through the system (e.g., to allow identification of past and emerging trends). In some embodiments, the patient and consultation volume may be provided and analyzed, i.e., by location.

Resource Utilization: Along with the data related to system resources that are captured in the Resource Utilization domain, this information may be vital to optimizing system performance. Additionally, near real-time analytics powered by tools such as Tableau may allow further in-depth analysis to be performed to gain insights and make decisions with regards to load balancing, team assignments, and resource allocation. In some embodiments, the system recognizes that the remote healthcare provider has an active consultation, but will not prevent them from accepting the additional consultation request. In some cases, the system comprises a load balancing feature that helps ensure no remote healthcare provider becomes overwhelmed with multiple consultations (for example, preventing acceptance of requests for consults that are estimated to exceed the response duration or timeline corresponding to the urgency of the consultations). When multiple remote healthcare providers are active ("on call") for a given hospital or set of hospitals, they may be given different roles such as primary and secondary or backup. In some embodiments, the system utilizes one or more rules to determine when to route a new inquiry to a given remote healthcare provider depending on their role, for example, between a primary and a backup provider. In some embodiments, the system uses a built-in load balancing strategy to ensure that no provider is overwhelmed with consults. Load balancing can establish a maximum number of routine or urgent consults that any one remote healthcare provider or team can accept, and then routes consults to a back-up provider or team. The provider can use clinical judgement to deviate from this assignment; however, it is intended to assist in creating a balanced workload. In some cases, the system defers to the autonomy of the primary if there is no backup or secondary provider available. Accordingly, using the urgency flags, aging times, and their own professional judgement, the remote provider can attend to each consult as they see fit based on need, urgency, and complexity. In some cases, much of the communication between the remote provider and the bedside clinician can be achieved through asynchronous messaging, allowing the intensivist to efficiently support multiple consults simultaneously.

Figure 23:
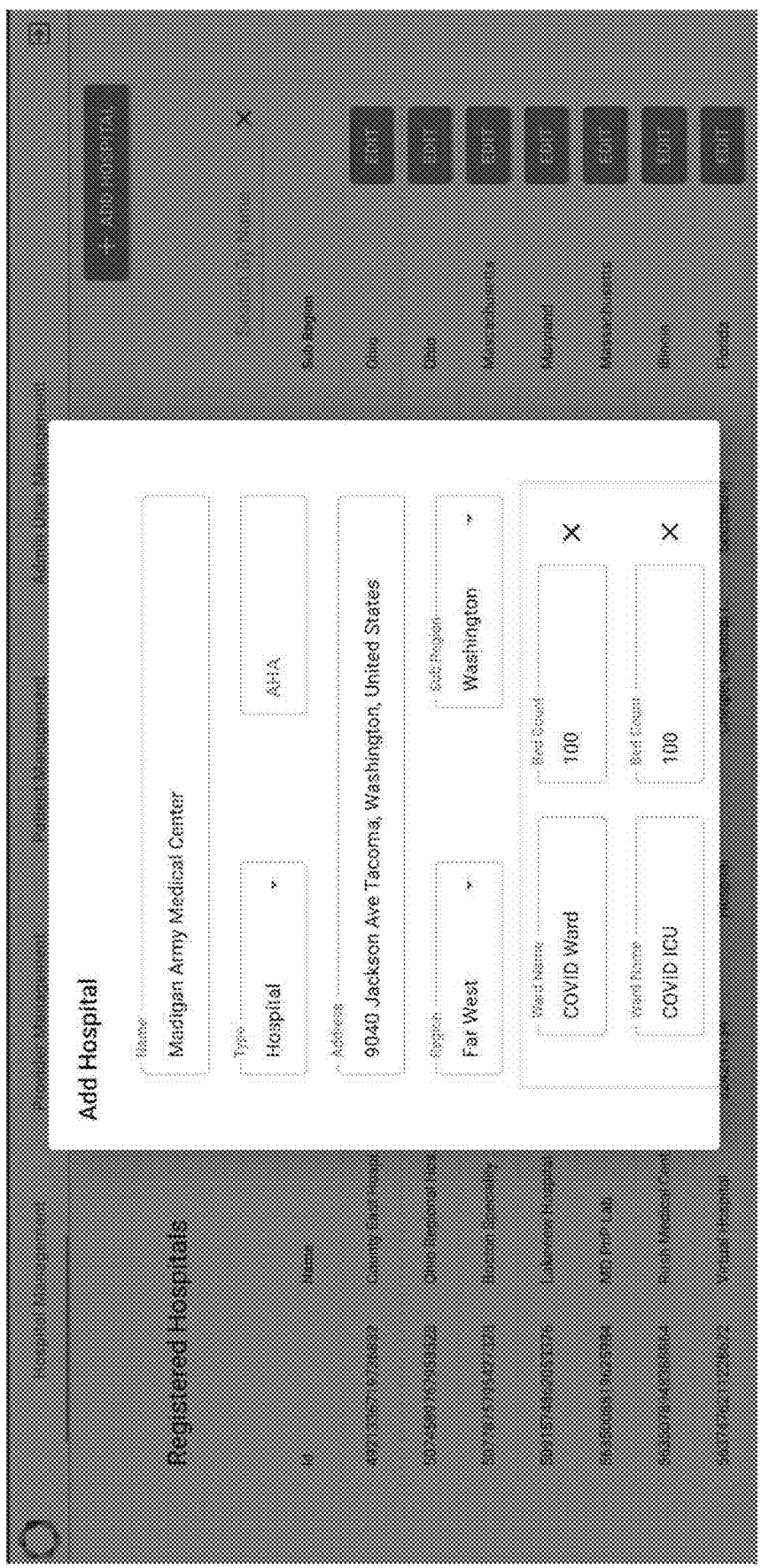
FIG. 23 shows a view of a user interface for an administrator portal hospital management tool with manual location entry pop-up window open, according to one or more embodiments herein.
Figure 24:
FIG. 24 shows a view of a user interface for an administrator portal provider management tool, according to one or more embodiments herein.

FIG. 22 shows a view of a user interface for an administrator portal hospital management tool. FIG. 23 shows a view of a user interface for an administrator portal hospital management tool with manual location entry pop-up window open. FIG. 24 shows a view of a user interface for an administrator portal provider management tool. The system may include an administrator portal. The administrator portal may be separate from or a part of the VCC. There are two main roles in the admin portal. One is a triage professional role who triages the self-registered patient from home location and assigns those patients to home providers (local care providers) who will then communicate with the self-registered patient through chat, audio and video calls using the app and also escalate to any virtual intensivist team. The second role is of an admin who can perform the following functions: a) onboarding a hospital or adding a new field hospital/site to the system; b) validating and approving the credentials of all providers (remote providers as well as local care providers) who signed up in the app; and c) broadcasting a system wide message (e.g., system alerts to all users of the app). A hospital, field hospital, or a virtual hospital can be added in real-time using the admin portal (e.g., as shown in FIG. 23) and may be available instantaneously for the users of the mobile app. In some embodiments, the admin portal may enable a user to manually add hospitals, providers, and/or patients. In some embodiments, hospitals, providers, and/or patients may be automatically reviewed and added to the system without administrator intervention. In some embodiments, the admin portal can be used to broadcast a system wide message/alerts to all users of the mobile app.

In some embodiments, the admin portal may facilitate one or more of a user groups function. The user groups function may ensure proper consult routing to the credentialed group of remote healthcare providers and/or maintain data access (e.g., patient medical information) within the credentialed group. The onboarding process for hospitals may use the same system and portals as shown in FIG. 23. The data is separated based on the credentials associated with the user group associated with individual hospitals. In some embodiments, the healthcare providers with the appropriate credentials in a hospital may have access to the patient's health record, whereas the healthcare providers who lack the credentials may not have access to the patient's health record. In some embodiments, a healthcare provider may not automatically have access to the patient's health record by virtual of affiliation with a credentialed hospital; the hospital may grant credentials to a particular healthcare provider by adding this provider to the user group of this hospital. After that, the remote healthcare provider may have access to view the patient's record. In an event of disaster when multiple hospitals may be quickly deployed and act, this user groups function can beneficially create an omnibus user group wherein all available hospitals may be onboard quickly. This allows all hospitals on the platform to have access to all the patients in need of healthcare without having to go through multiple layers of authentication process. In some embodiments, in a normal deployment of onboarding a hospital user group, this credential mechanism may aid safeguarding access to patient's health record and limit access to the credentialed user group. In this scenario, when a bedside provider requests, e.g., via the app associated with the telemedicine platform, a consult for patient A, the system may look up a list of hospital user groups and identify the user group (e.g., the group of remote clinicians) the bedside provider is associated with. Once the user group is identified, the system may pull out a list of all (or mostly all) currently-available remote healthcare providers and apply a filter on the list to generate a resulting set of providers. The filter may be pre-defined or customized as needed. Therefore, the generated-resulting set of providers are the group of healthcare providers who has access to that identified hospital user group alone, this may reduce the risk of patient health recording leaking and improve the performance of the system by reducing overhead.

The multiple roles (patient, bedside provider, remote provider, and VCC administrator), their self-registration workflows, and their initial views and functions, are described in greater detail below.

Self-Registering Patient

The system may include a patient self-registration portal which allows a person who is not in a healthcare facility and who doesn't have another person caring for them (e.g., layperson, or trained caregiver) to initiate contact with the system via the app. The patient may be asked to provide name, date of birth, gender, and/or a phone number. These items may be collected to have sufficient data to generate an enduring unique patient identifier. The phone number may allow for contact to be made asynchronously from the system as described herein. The patient may also enter a description of their situation, a question or issue, and/or some reason why they are accessing the telemedicine system. The information from the self-registration, including contact info and the situation/issue, may be populated real-time into a triage role view inside the admin portal. The patient may be presented with a chat window where the system may prompt them to upload their ID and insurance information and/or display a message that consultation is pending. In some embodiments, the patient may be asked to enter a zip code, or the mobile device GPS data may be accessed, in order to gather data on geographic distribution of patients. The triage role may then assign a home provider to that patient, who may then start discussing the situation with either patient or a family member who is supporting the patient. The home provider may be able to send a message, initiate a video or an audio call using the app or if the patient is not available on the app, they can use the phone number to asynchronously contact the patient. There may initially be no direct communication between a patient and the expert remote providers, without triage performed at the virtual command center, based on the nature of the chief complaint entered into the form. In some embodiments, triage may be performed by a user (e.g., physician or other Home Provider) accessing the virtual command center. Alternatively, or in combination, triage may be automatically performed by the system. The self-registration feature may offer the advantage of earlier access to care for patients who may otherwise not have access to specialists. Additionally, the self-registration functionality may serve as another valuable mechanism to alert the system and relevant partners (e.g., governmental agencies, hospitals, etc.) about emerging disasters as early as possible.

Home Bedside Provider

The "Home Provider" role may connect with patients by signing up to the App as Home Provider and can then communicate with patients and/or add these patients to the message board as required. That way, the care can be escalated by the "Home Provider" to any virtual intensivist team. This approach of "contact and triage" may mitigate the risk of the "worried well" overwhelming the system with non-urgent consults (a well-known phenomenon in triage, disaster response, and telemedicine).

Bedside Provider

In the event a provider engaging in patient care wishes to request a consult, they too may self-register for an account in the app following download. The self-registration process for a provider may request name, email, phone number, and, if "bedside provider" is selected, a hospital location, home location in the scenario of an in-house nurse, or a facility location in the scenario of a senior living facility or nursing house may be entered. The hospital location may be one of several pre-populated hospital choices or a "virtual ward" if the care is being provided outside of a hospital (e.g., at a clinic, gymnasium, patient home, etc.). A password may be chosen by the provider, and an end user license agreement may be presented with the option to select. Once in the system, the bedside provider may be presented with two action options: 1) Access the on-call directory, or 2) Register a patient to create a consult. Accessing the On-call directory may give the bedside provider the opportunity to call a provider directly for an urgent/emergent question, and or to pass information vertically up the system. If the provider chooses to register a patient/create a consult, they can input the patient's name, date of birth, and gender. They may then be given the option to manually input some patient information. Exemplary patient information may include supplemental oxygen and level of consciousness in a non-limiting example. The specific data fields may be programmable and able to be specified in order to adapt to different disasters. Supplemental oxygen and level of consciousness were chosen for an exemplary COVID19 telemedicine system embodiment because, along with vital signs (HR, BP, Sats, RR, temp), they allow the calculation of a National Early Warning Score (NEWS Score) for triage and acuity ranking as a demonstration of COVID19 data flow. To further facilitate triage, and mark acuity, the consult may be marked "urgent" at this point if needed. Next, if the provider has access to a physiology monitor that has been integrated into system's device ecosystem, it may be linked within the app to the patient at this time. Finally, the chief complaint/consult information may be free texted into the system and the consult request may be submitted. The consult request may then be displayed in the active consults section of the user interface. On the consult screen, patient vital signs data may be viewed, and based on the system's acuity algorithm, each patient may be intuitively color-coded to indicate urgency (e.g., red/yellow/green) based on their physiology data (which may be manually and/or automatically entered as described herein). Patients can be searched and filtered by "active" consults (i.e., those accepted by a remote provider) and "pending" consults (i.e., those awaiting acceptance by a remote provider). If the active consult is selected, the provider may enter the consult chat screen, in which asynchronous communications (text, photo, document) may be uploaded to the consult, or, once the consult is accepted by a remote provider, synchronous (voice and video) communications can be utilized. Once the consult is accepted by a remote provider, they may communicate synchronously or asynchronously as indicated. The system may also be configured to generate an SOS call to any available online provider if there is a delay in response by the designated provider. This SOS feature may alert every available provider online in the system and may continue until answered.

The telemedicine platform may provide qSOFA implementation in its system. A qSOFA score is calculated based on the patient intake form filled by the patient or by a bedside care provider. The parameters for the qSOFA score calculation may include the following: First, a Glasgow Coma Scale/Score (GCS), which is calculated by asking i) best eye response, if spontaneously, then GCS=4, if respond to verbal command, then GCS=3, if the patient responds to pain, the GCS=2, if there is no eye opening, then GCS=0 (not testable=NT; ii) Best verbal response: if oriented, then GCS=5, if confused, then GCS=4, if inappropriate words are spotted, then GCS=3, if patient responds with incomprehensible sounds, then GCS=2, is there is no verbal response, then GCS=1, if it is not testable/intubated, then GCS=0; iii) best motor response: if patient obeys commands, then GCS=6, if localizes pain, then GCS=5, if withdrawal from pain, then GCS=4, is flexion to pain, then GCS=3, if extension to pain, then GCS=2, if there is no motor response, then GCS=1, if not testable, then GCS=0. Combining all the GCS scores from the above three questions, the system may generate a total GCS score. If the total GCS score is greater than a predetermined threshold, e.g., 15, then add 1 to the qSOFA score, if not, then add 0 (not change) the qSOFA score.

Second, the bedside provider may evaluate respiratory rate, and if the respiratory rate is above 22, then add 1 to the qSOFA score, otherwise, add 0 to the qSOFA score. Third, if the systolic BP is lower than 100, then add 1 to the qSOFA score, otherwise, add 0 to the qSOFA score. If the resulting qSOFA score is lower than a pre-determined threshold, e.g., 2, then the patient is not in high risk for in-hospital mortality; if the resulting qSOFA score is equal to or greater than a pre-determined threshold, e.g., 2, then the patient is in high-risk for in-hospital mortality. The above specific criteria, questions, and scores are only presented as examples; one may implement other criteria to generate an acuity score. The qSOFA score may be displayed next to patient information to help the remote care provider to assess the acuity and/or risk of a patient.

Remote Provider

In support of the system, existing providers may log in (provided they already have an account) from the front screen. Additionally, new providers may register for an account. New providers may be prompted to enter their name, phone number, email address, and if selecting "remote provider" to provide consultative/expert care, they may be prompted to enter an NPI number. This may be an optional entry or a required entry. Once logged into the system, the remote provider may be able to see a list of pending (i.e., not accepted) and active consults (i.e., those accepted by a provider). This list may be color coded (e.g., red/yellow/green) by acuity as described herein, and marked urgent. These consults can be expanded to show the vital signs data, and/or selected to open up the chat screen for the consult. If the consult is active (meaning the provider has accepted the consult) the chat screen may display upon expanding the patient, and may allow asynchronous communications (text, photo, document), or synchronous communications (voice, video). The remote provider can interact with the bedside provider or a patient, and once the consultation is finished, can select "complete consultation". At that time an "assessment and plan" templated chat may appear, allowing a final documentation of the diagnosis and the plan communicated to address it.

Patient Transfers

A local care provider (e.g., a bedside provider or a home provider) can transfer a patient from one ward to another within the hospital (e.g., COVID Ward to COVID ICU) as well as from a site (home or any field hospital) to a hospital while maintaining using the app and telemedicine platform. Once the physical transfer is initiated and done, the details may be posted against the patient in the message board. Additionally, the current location of the patient may be clearly marked in the patient details in the app. The remote provider who is providing care may be able to view this information and be informed of the patient's physical movement. The remote healthcare provider may also be able to view the medical devices and/or lab capacities that are available in this hospital location, and provide orders or other patient care instructions accordingly. If a local IoT platform is available but there is no access to the internet, but local intranet access is available, then with the system platform data can be transferred from one bedside system to another. This may allow for a robust set of data to be made available instantaneously at the patient beside at the time of transfer, largely independent of internet access.

Provider Handoffs

In some embodiments, there may be at one or more kinds of provider handoffs available in the app. In some embodiments, a handoff may occur when a local care provider (e.g., a bedside provider and/or home provider) hands off all of their consults to another local care provider at the end of their shift. Once the handoff is completed, the message board for the patient may be updated with the current local provider so that the remote provider can continue providing care without any disruption. Alternatively, or in combination, a handoff may occur when a remote provider hands off the patient virtually to another remote provider. In this case, a first remote provider may initiate a virtual handoff using the app. The other remote providers who are available may receive a notification of the consult at which they can act on and accept the consult. Every handoff may be accompanied by a handoff summary note for the next provider to read on the procedures and actions performed by the previous remote provider.

Remote Provider Teams

When a Remote Provider accepts his first consult, a new team may be created automatically by the system. For example, Team Alpha. The system may generate teams based on built-in, user-generated, or automatically-generated (e.g., via machine learning) staffing ratios. Staffing ratios may vary depending on the different roles created in the system for remote providers These ratios can be altered based on the real use cases. In an exemplary embodiment, when a Team is created, the system may look at the other Remote Provider types and assign them to the Team Alpha by using the following rules:

Doctor of Medicine (MD)/Doctor of Osteopathic Medicine (DO)—can be part of only one team.

Advanced Practice Provider (APP)—can be auto assigned up to 3 teams.

Registered Nurse (RN)—can be auto assigned up to 5 teams.

Respiratory Therapist (RT)—can be auto assigned up to 6 teams

Registered Pharmacist (RPh)—can be auto assigned up to 6 teams

In some embodiments, when a consult is accepted by a MD/DO, a remote care team is automatically formed by the system based on the availability of other remote providers (APP, RN, RT and RPh). In some embodiments, the MD/DO may preselect a group of other remote providers (APP, RN, RT and RPh) based on some pre-defined criteria. For example, the MD/DO may designate a group of remote providers (APP, RN, RT and RPh) as the favorable group for a patient who has respiratory conditions, based on his past experience working with the team or based on the remote providers' specialties. Team Alpha can be associated with multiple patients. The system may give the flexibility of configuring the quota of consults a team can take at a given time.

Clinical Training Materials

In some embodiments, the clinical training materials may be hosted as a static website, which may be readily available and accessible inside the app by local care providers as well as remote providers. In some embodiments, the clinical training materials may be downloaded from a server onto a user's device and stored locally to allow for offline access.

In some embodiments, the system may comprise a comprehensive library of device specific proprietary data communications interfaces of all potential devices that might be deployed in disaster situations. To improve device interoperability, the system may also include a standard medical device information model and controlled vocabulary based on current international standards to assist with ensuring rapid integration during disaster scenarios.

Open Patient Data API

The system's Cloud Coordinator may implement an open API, which may allow for data to be organized so Virtual Wards can be created. The cloud coordinator may also have the ability for data containers to be created for situational awareness data modules as described herein. This robust API may contain multiple functions including the ability to organize real-time streaming patient data in a way the telemedicine app can consume data in an organized way around the virtual wards. This may include the physical location of the patient.

Master Patient Index

The system's cloud coordinator may implement an electronic master patient index. This master patient index may allow for a list of patients and their current and historical resources to be leveraged in the system. The master patient index may also generate unique patient identification for the system and may have the ability to implement patient matching rules in the system.

Data repository

The system's cloud may implement a big data storage capability in conjunction with the cloud coordinator. The data repository may aggregate and store data coming from both the connected devices and the telemedicine applications. Data may be integrated with the local, regional, and national dashboards. Historical data may be made available to the telemedicine applications via the cloud data repository. This data repository may be configured to copy database tables to other databases such as the commons data repository utilizing standard open tools available in the Hadoop Data File System (HDFS). HDFS views can also be setup for operational dashboards in order to leverage the power of large data sets for near- or real time analytics. The data analytics can be displayed via the virtual command center dashboard such as shown on FIG. 33.

Interoperability

The Open Patient Data API, Master Patient Index, and Data repository may be based on open standards, a robust data dictionary as described herein, and may be key elements which allow data to be not only aggregated for research but also allows for telemedicine systems to interoperate at least in the ability to share data. For example, when a patient is associated with multiple sites with multiple vendors as part of the system, the patient's previous data, may be available to both the local and remote care provider leveraging this least common denominator data set.

Time Tracking

In some embodiments, the system may include an automatic time tracking component for critical care billing. In some embodiments, rather than closing a consult when it has been deemed completed, the consults may be left open for a period of time (or indefinitely) to enable the care team to go back to the patient data as needed. For example, if consults could be left open, or at least for a period of time knowing that particular bedside provider and the consulting critical care clinician will both be available for a specified period of time, it may make the most sense for any additional issues with that patient to be addressed by the same critical care consultant. With that in mind and considering critical care is billed based on the initial encounter of 30-74 minutes (99291) followed by additional 30-minute blocks of time (99292), having the app automatically track actual time spent in the consult may be extremely helpful from a billing/administrative perspective.

Staffing and Workload Models

The systems and methods described herein may create a virtual network of multi-professional critical care experts through real-time, dynamic recruiting using the telemedicine App and available database(s) of critical care professionals. A Virtual Command Center (VCC) created on the system's web portal, and supported by authorized personnel, may ensure critical care provider credentialing and availability, as well as personnel and resource control, and oversight of the response to calls on the system's network. As demand for critical care support surges, the telemedicine App may geo-strategically and incrementally recruits critical care professionals into the available provider pool via the telemedicine App in real-time, thereby forming an elastic, cloud-based virtual care team. The system's network may simultaneously match providers and patients to needed critical care resources via the telemedicine app, with algorithms to estimate medical demands. The telemedicine app may further prioritize patient care needs to facilitate dynamic staffing and fluid movement of professionals among care teams to maintain appropriate staffing ratios and response times in a dynamic crisis environment. Critical care professionals can thereby be mobilized to address patient care needs in a flexible, scalable, and dynamic fashion when demand may rapidly outpace supply, and patients can also be transferred between virtual care teams in the network to ensure patients and bedside providers receive timely support from the remote telemedicine team. In some embodiments, machine learning algorithms may be utilized (e.g., developed from the implementation data) facilitate dynamic staffing to match demand.

In some embodiments, staffing may be achieved through a pyramidal starring model, with a trained or experienced critical care physician advising multiple ICU APPs and/or non-ICU physicians, who in turn may each interact with multiple team members under them, and so on down to the patients. This paradigm may ensure that the highest level of critical care expertise is provided to the most people. It can realistically be accomplished through an integrated critical care telemedicine platform. For example, in an area such as New York City where there was a projected 7000-ICU-bed shortage during COVID-19, non-intensivists may be required to provide complex critical care beyond their training and scope of practice. Additionally, they may do so in an environment that was not designed for critical care delivery (e.g., hospital floors, tents, operating rooms, hallways, etc.). Having on-demand access to nationwide board-certified intensivists with a plethora of experience will undoubtedly improve patient outcomes and improve bedside provider morale.

Recruitment and Vetting Process

In some embodiments, providers may be recruited through a call for volunteer request. Providers may be asked to provide their contact information, credentials, and expertise of the volunteers, which may be verified through the publicly available NPI system. The provider's credentials, including specialty and licensure requirements were verified and the NPI number may be verified and recorded by the system. In some embodiments, the process to recruit, vet and onboard volunteers may be optimized through automation.

Additionally, an automated alert system to communicate to providers registered with an account may be used to recruit providers when the need arises. For example, the automated alert system may be triggered (e.g., by an emergency) and may send alerts to providers via an external notification system (via telephone calls, etc.). A virtual command center may be set up and/or accessed by an authorized user, who may trigger the app to send out an in-app call for volunteers. In some embodiments, this may be done automatically. Virtual wards may be set up as described herein and responding providers may be onboarded, oriented, updated, and sorted into teams as described herein.

Staffing and Workload Estimates

In some embodiments, a critical care provider may be reasonably expected to manage 2-4 hours per day of consult time. For an exemplary network of about 300 willing, experienced, self-identified, vetted critical care providers on the staffing roster, approximately 35-50 consultants may be on at any given time. Simulation testing of telemedicine system in prolonged field care scenarios have shown that most tele-critical cares calls in the resource limited/disaster setting range from 5-10 minute for quick questions, dose/vent adjustments, while some are longer in the 25-35-minute range (including new complicated consults, procedure mentoring, etc.). If we estimate that each would provide for 3-4 consults per hour (i.e., a consult can be managed on average in 15-20 minutes), this would allow for 100-200 consults hourly or 2400-4800 per day. This pace may likely be sustainable for the initial 5-10 days of a pandemic, disaster or mass casualty event without further recruits, resulting in 12,000-48,000 consults handled in that initial period. If the event were similar in prevalence and severity to the current COVID-19 pandemic, approximately 10-20% of affected people would be severely ill; in COVID-19 approximately 15% of affected persons require inpatient care, and 5% of the affected require critical care. This means that the projected 12,000 to 48,000 consults in the first week (5-10 days) could represent the steady state System Load of a similar pandemic/mass casualty even affecting 50,000 to upwards of 960,000 people depending on disease severity in the first week. This initial system load could be expanded rapidly with additional onboarding as described herein, and may be triggered by data analytics (e.g., as shown in the virtual command center) of real-time consult load, length, type of providers engaged, and percentage of providers engaged. If the system is kept at 60-80% utilization, the additional capacity would allow flexibility in the response and time to recruit, vet and onboard new remote providers. The rapid and intuitive usability of the system may lend itself to this rapid scalability and expansion. If a successful recruiting call was able to increase the remote provider pool up to 10%, then 60,000-200,000 weekly consults could be handled at steady state. If 20% of providers were part of a pool able to be utilized part time, or periodically (e.g., 1 week every 3-4 weeks) a staffing requirement of 1000 providers, it could sustainably be managed for extended periods of many months to indefinitely. These 1000 providers could, according to the estimates above, provide 40,000 to 160,000 consults weekly at steady state, helping manage a disaster notionally affecting 1-3 million people at a time.

Workflow Summary

The system may be configured to provide a large scalable pool of willing, highly skilled, geographically diverse, pre-trained providers will be available on demand at a moment's notice. On-site providers may access the system's network using the telemedicine app when help is needed and may be routed to the virtual command center for a brief situational awareness update and credential verification. Bedside providers may then create accounts and register patients in real-time after a verification code is sent to them from the command center using a standard 2 Factor Authentication process. After registering a patient, the bedside provider may send out a message (e.g., standard, urgent, or SOS options for triage purposes) via the App including a brief patient description and situational details. This message may be visible to ALL remote Intensivists who are logged in to the App (e.g., providers recruited after a situational alert from bedside). Any intensivist can then accept the consultation request and may be then directly connected to the bedside provider. The providers may formulate a care plan together using Audio-Video and/or text communication in real-time. Providers may also be able to upload images to assist with treatment decisions.

Furthermore, additional clinical information in the form of vital signs and acuity scores may be visible to the Intensivist based on the initial information provided by the bedside provider. An exemplary acuity score proposed in at least some embodiments may be the NEWS score, which can be calculated in real-time by the Application, based on vital sign information for a given patient as described herein. The patients may then be color coded (e.g., Red=High Acuity, Yellow=Medium Acuity Green=Low Acuity) within the App and thereby enable a severity of illness based triaging mechanism for the remote providers, who can prioritize requests based on the acuity score. Given that automated acuity scores are not always reflective of true severity, the App may also enable a manual override of the system generated acuity.

In the most austere situations, the bedside provider could manually enter vital signs into the App OR connect a wearable device to the telemedicine App. The telemedicine App may be configured to communicate with wearable devices, such as Athena GTX or other devices from which real-time data can be retrieved. The ability to view vital signs may enable remote Intensivists to quickly make triage decisions and enable transfer of patients to a higher level of care if required, and prioritize the consults within the telemedicine system as well.

The telemedicine system and methods described herein may facilitate collaboration between multiple Critical Care providers. Multi-disciplinary teams can be created (the ideal composition of each team consists of a remote Intensivist, RN, RT and Pharmacist) using real-time knowledge of the number of available professionals using the system dashboard as described herein.

Team creation may be a dynamic function that takes into account the complexity of cases, provider to patient ratio, and provider efficiency. Using real-time user data from the App which is visible to system administrators in the system Virtual Command Center, decisions can be made using a combination of machine learning and manual processes to optimize functionality of the system. Team functionality may also enable patient handoffs to ensure appropriate continuity of care as described herein.

Provider efficiency and productivity may be tracked within the system based on the processing time for various consults. This metric may form the basis for dynamic reassignment of patients between providers and teams using a combination of automated SLA algorithms and manual processes as required.

Following the Tele Critical Care evaluation of the patient, the remote Intensivist may complete the consultation with a formal summary note, which can be exported to the EMR of the patient.

The system may be configured to integrate with both medical record systems and device data aggregators (such as DocBox, etc.). This capability may allow the remote intensivists to have a comprehensive aggregated view of real-time data from multiple bedside devices, which may facilitate complex care decisions as patients move into higher levels of care. During the transition from a non-hospital location to hospital location, patient data may be archived, stored, and remain retrievable to create a longitudinal integrated care record.

The systems and methods described herein can integrate with bedside and wearable monitoring and biosensor devices, which may continuously transmit key patient data, with real-time data optionally displayed on the App to immediately identify and transmit significant deviations from settable thresholds. Flow of information to providers may be supported by automated algorithms that provide information batching, provider response suggestions, flagging of overdue requests, identification of dangerous vital signs, and adverse events data. Data may be visually displayed to allow providers to easily process it. On-site beside providers can prioritize and communicate the urgency of their support needs via the software. The network of remote providers can then view the streamed data in real-time and use the software to prioritize and communicate (via secure messaging or audio-video) with on-site providers (or patients) to ensure timely responses to support needs. The telemedicine App and infrastructure on the backend may support multi-connectivity communications protocols. This may allow a device or wearable paired with the telemedicine App client/user (e.g., on-site provider or patient) to harness available communication links at a given location. These links can be aggregated to provide a thick pipe to the cloud infrastructure on which high-bandwidth, low-latency data streams can be transferred reliably and efficiently, analyzed, and displayed for use by on-site and remote providers and command center personnel. The result may be high availability across networks and geographies of high-definition and high-resolution data for decision support.

Data Collection and Management

Figure 25:
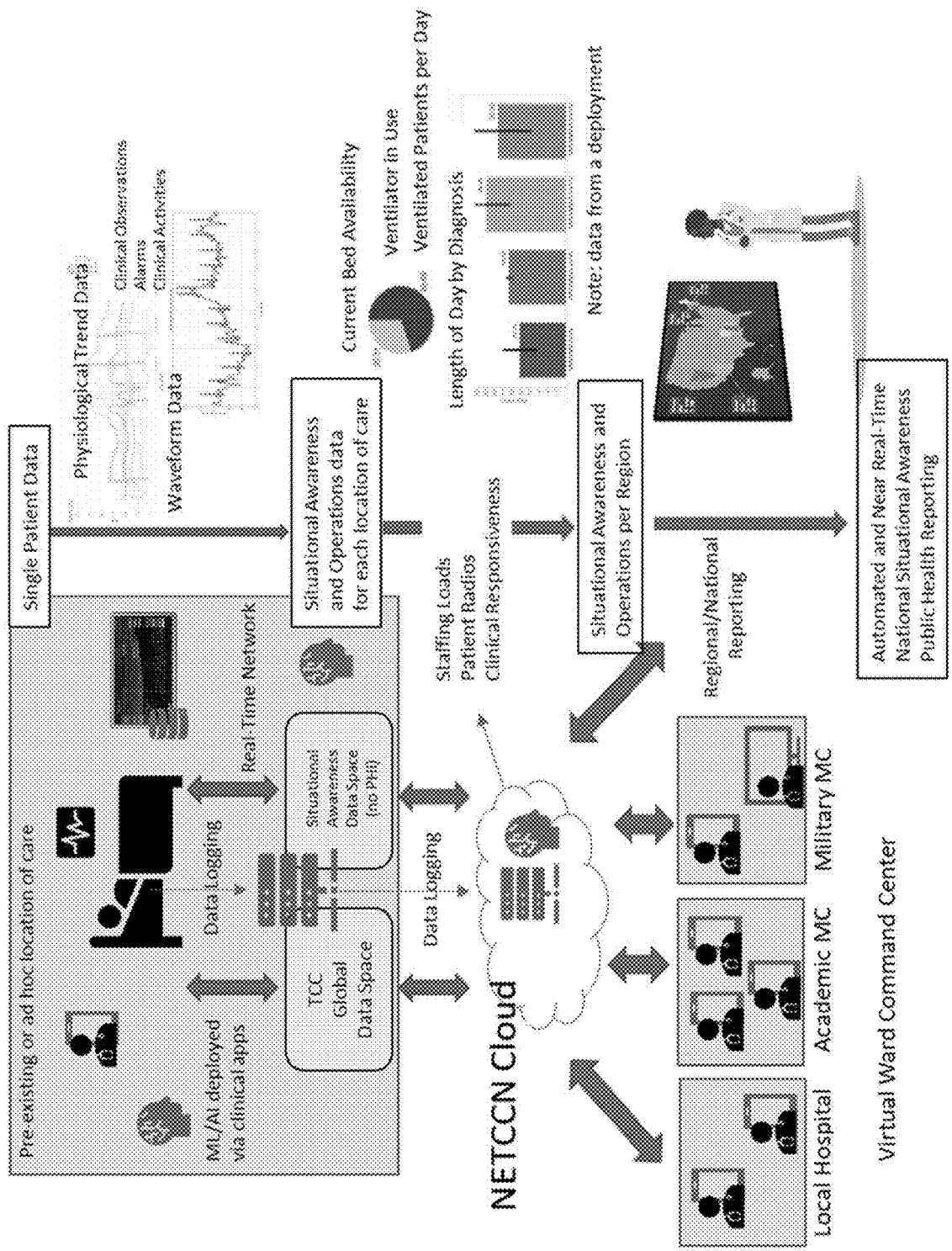
FIG. 25 shows a schematic drawing of a system for data collection and management using a telemedicine system, according to one or more embodiments herein.

FIG. 25 shows a schematic drawing of a system for data collection and management using a telemedicine system. The telemedicine system described herein may provide a platform for meaningful medical device interoperability that may enable advances that medicine needs to improve healthcare both clinically and operationally. The data model may be designed to facilitate and enable its use as shown in FIG. 16. The primary functions of the telemedicine system described herein are providing specific clinical and operational insights in real-time, providing the ability for tele-critical care, and provisioning of operational data for situational awareness. These operational insights may include: the number of patients are currently on ventilators and the number of ventilators remain available; the number of beds are available at an ad hoc site; the types of medications are being used; the relationship between use of a medication and discharge time. These insights may be created from the data collected during the patient stay. Retrospectively, this data from this common database can be used for research purposes, and also to implement automation into the system to assist in the response. In some embodiments, these operational insights may be studied, labelled, and fed into a machine learning algorithm to improve future operation.

The system may be configured to connect, via a distributed and scalable IoT platform, to any vendor medical devices including monitors, body sensors, ventilator, infusion pumps and to provide near real time monitoring to remote expert care teams, and/or cybersecurity to medical devices. The system may automatically collect, aggregate, normalize, and/or stores real-time data at the bedside and on a Data Cluster. Then, it may communicate this data in near real-time to the TCC Virtual Data Space (e.g., as shown in FIG. 15). The TCC Virtual Data space may enable data to flow to multiple applications simultaneously. The data can flow to both the application and simultaneously to regional and national reporting dashboards. This capability also means that multiple telemedicine sites with different vendors may consult on the same patient both simultaneously and asynchronously.

Figure 26:
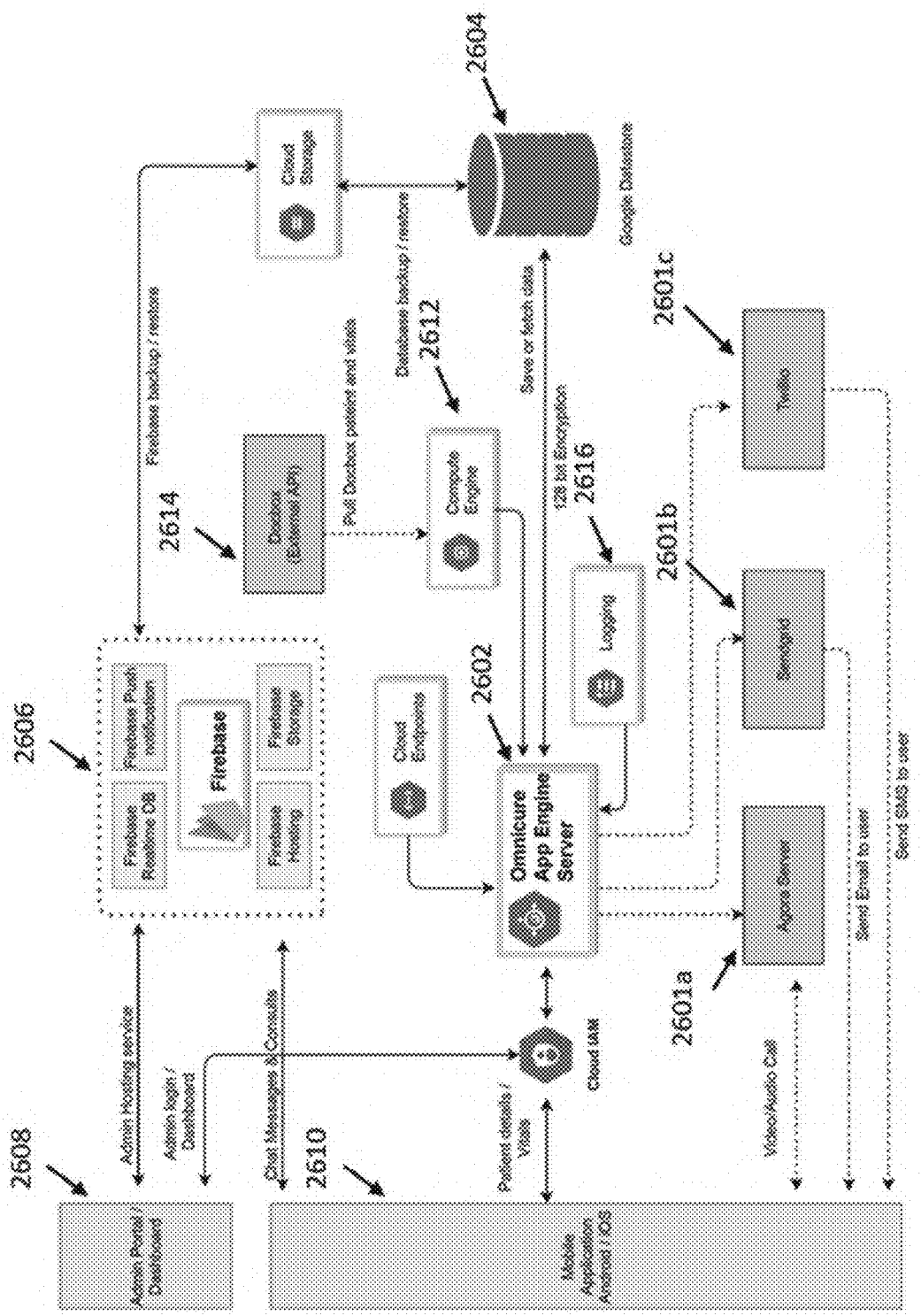
FIG. 26 shows an architecture for the telemedicine platform, according to one or more embodiments herein.

FIG. 26 shows an architecture for the telemedicine platform. As shown in FID. 26, the telemedicine platform may include a number of components collaborating with one another to provide seamless, efficient user experience and better care for patients. In some embodiments, the telemedicine platform may comprise an app engine server 2602. The app engine service 2602 may coordinate with other components of the telemedicine platform to provide various functions, as described elsewhere herein. For example, the app engine service 2602 may coordinate with a logging element 2616 to facilitate user log in process. In an example, the app engine server 2602 may coordinate with a real-time voice and video engagement server 2601a (e.g., Agora server) to facilitate an audio and/or video communication between users. In an example, the app engine server 2602 may coordinate with a sendgrid 2601b to send text-based (e.g., email) communication to a user. In an example, the app engine 2602 may coordinate with a cloud-based server 2601c (e.g., Twillio) to send SMS or other communications to a user. The above operations may facilitate a mobile application to provide the various interfaces (as described elsewhere herein) to different users via a mobile application element 2610 (e.g., android or iOS devices). These interfaces may be compatible with any web browser application, mobile application, or other applications used by a user of a client node. In some embodiments, the interface may provide patient details, vital signs, lab results, etc. to a cloud IAM, and the cloud IAM may relay this information to the app engine server 2602. In some embodiments, the cloud IAM may relay this information to an admin portal/dashboard 2608.

The app engine server 2602 may communicate, wired or wirelessly, with a database 2604 to store or fetch data. The database 2604 may communicate with cloud storage to backup data and restore data from the cloud storage. In some embodiments, the cloud storage is communicatively coupled to an administrative hosting module 2606. The administrative hosting module 2606 may comprise some sub-components, such as real-time DB, push notification, hosting, and storage. The administrative hosting module 2606 may provide an administrative portal and/or dashboard 2608 for a user. The functionalities of administrative portal and/or dashboard 2608 are described elsewhere herein. In some embodiments, the administrative portal and/or dashboard may communicate directly with the mobile application module to provide administrative level interfaces to a user, as described elsewhere herein. In some embodiments, the app engine 2602 may utilize a compute engine 2612 to pull docbox information for patients and the vital signs of a patient from a docbox 2614. In some embodiments, the docbox 2614 may comprise an external API to facilitate documents search and transfer.

Figure 27:
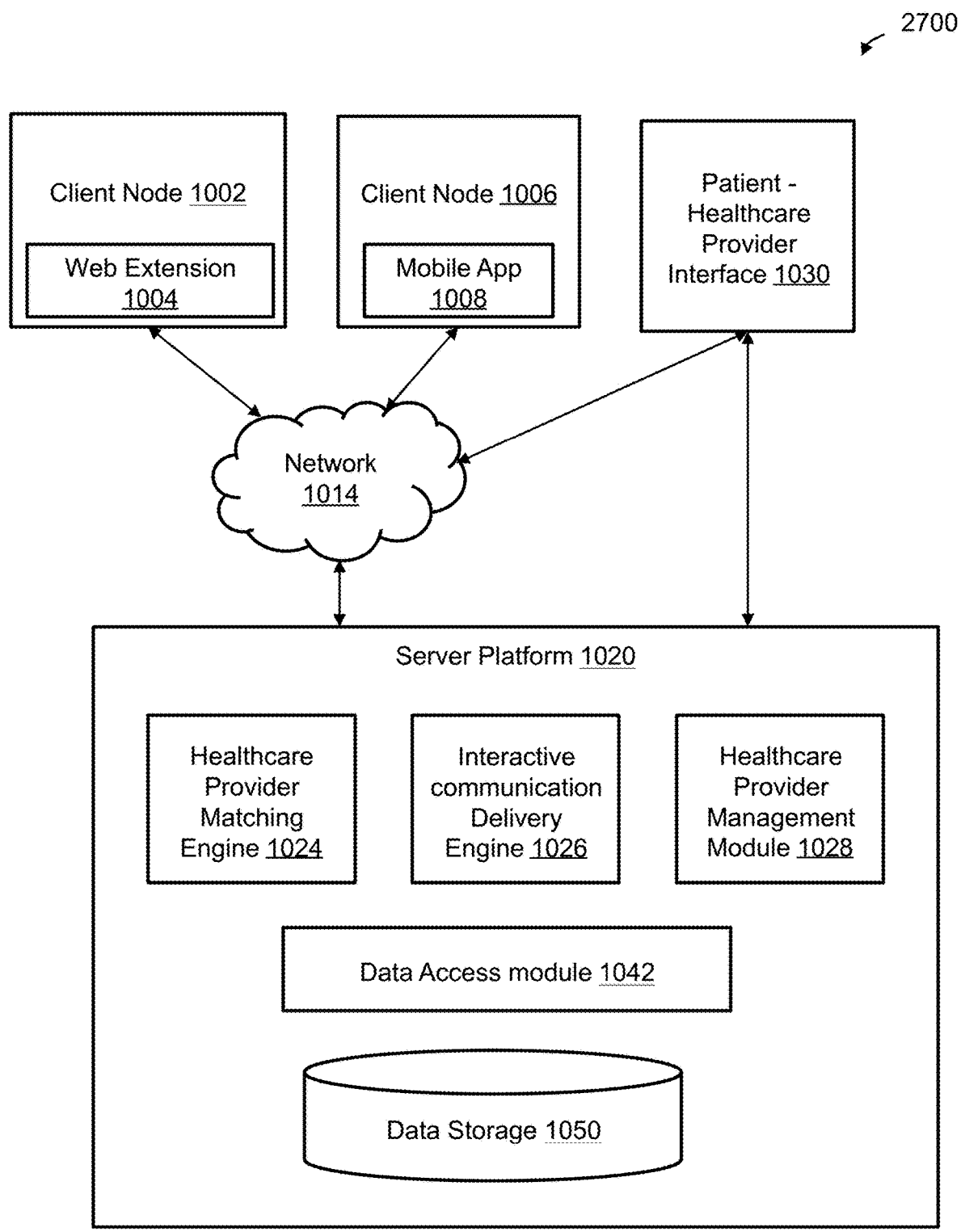
FIG. 27 is a block diagram depicting an example system, according to embodiments of the present disclosure, comprising a client-server architecture and network configuration to perform the various methods described herein.

FIG. 27 is a block diagram depicting an example system 2700, according to embodiments of the present disclosure, comprising a client-server architecture and network configuration to perform the various methods described herein. A platform (e.g., machines and software, possibly interoperating via a series of network connections, protocols, application-level interfaces, and so on), in the form of a server platform 1020, provides server-side functionality via a communication network 1014 (e.g., the Internet or other types of wide-area networks (WANs), such as wireless networks or private networks with additional security appropriate to tasks performed by a user) to one or more client nodes 1002, 1006, and/or one or more patient—healthcare provider interfaces (e.g., patient—healthcare provider interface 1030). FIG. 27 illustrates, for example, a client node 1002 hosting a web extension 1004, thus allowing a user to access functions provided by the server platform 1020, for example, requesting a consult from the server platform 1020, receiving patient data from the server platform 1020, receiving requests of consults relayed by the server platform 1020, sending/receiving communications facilitated by the server platform 1020, etc. The web extension 1004 may be compatible with any web browser application used by a user of the client node. Further, FIG. 27 illustrates, for example, another client node 1006 hosting a mobile application 1008, thus allowing a user to access functions provide by the server platform 1020, for example, requesting a consult from the server platform 1020, receiving patient data from the server platform 1020, receiving requests of consults relayed by the server platform 1020, sending/receiving communications facilitated by the server platform 1020, etc. Delivery may be through a wired or wireless mode of communication. Examples of communications may be in the form of messages (e.g., in-app messaging or via external text messaging systems), audio-video calls (e.g., in-app calls or to an external phone number), orders, notes, and the like.

A client node (e.g., client node 1002 and/or client node 1006) may be, for example, a user device (e.g., mobile electronic device, stationary electronic device, etc.). A client node may be associated with, and/or be accessible to, a user. In another example, a client node may be a computing device (e.g., server) accessible to, and/or associated with, an individual or entity. A node may comprise a network module (e.g., network adaptor) configured to transmit and/or receive data. Via the nodes in the computer network, multiple users and/or servers may communicate and exchange data, such as patient data, vital signs, lab results, patient—healthcare provider communications, etc. In some instances, the client nodes may receive and present to a user data item (e.g., an image of a patient, a virtual meeting session, a doctor's order, etc.). The client nodes may also gather data associated with a patient and transmit the data to the server platform 1020 (e.g., patient vital signs data, acuity level, etc.). In some embodiments, the client nodes may facilitate an onboarding process, as described elsewhere herein, for a patient, a bedside caregiver, and/or a healthcare providers. Alternatively or additionally, the client nodes may include virtual reality (VR) devices, via which a VR environment may be presented to a remote healthcare provider, wherein the VR environment may comprise images of a patient, video feeds of a patient, one or more controls that may enable the healthcare provider to control the VR environment. The video feeds may be obtained by one or more sensors located near the patient. Alternatively or additionally, the video feeds may be obtained by cameras. The video feeds may include audio feeds associated with the environment of the patient. Alternatively or additionally, the audio feeds may be interactive (e.g., bidirectional), which may enable an interaction (e.g., conversation) between a subject (e.g., bedside caregiver, a patient, etc.) and a user (e.g., a doctor or doctor's assistant).

In at least some examples, the server platform 1020 may be one or more computing devices or systems, storage devices, and other components that include, or facilitate the operation of, various execution modules depicted in FIG. 27. These modules may include, for example, healthcare provider matching engine 1024, interactive communication delivery engine 1026, healthcare provider management module 1028, data access modules 1042, and data storage 1050. Each of these modules is described in greater detail below.

The healthcare provider management module 1028 may receive and manage healthcare providers. The healthcare providers, in some embodiments, may comprise a list of healthcare providers and their affiliated hospitals. In some embodiments, the healthcare providers are grouped based on their affiliated hospitals. In some embodiments, the healthcare provider management module 1028 may receive profile and/or credential associated with the healthcare providers. In an example, such profile may include healthcare provider's specialties, current workload, diagnose accuracy history data, average time spent on a patient, patient's review score, etc. These information may be collected via self-filled forms, hospital record for the healthcare providers, registered information with American Medical Association, past completed consults, etc. This information may help the server platform 1020 to target the cluster of healthcare providers that may provide optimal results for a particular consult. Additionally, this information may also help the server platform 1020 to reduce traffic via the computer network 1014 when broadcasting a consult request from a bedside caregiver or a patient.

The healthcare provider matching engine 1024 may match the healthcare providers as set forth by the information on their profiles. In some embodiments, the healthcare provider matching engine 1024 of the server platform 1020 may receive information associated with a requested consult from the client node 1002 or 1004, as described elsewhere herein. For example, the client nodes may send a consult regarding a patient who is experiencing short of breath. The client nodes may then operate alone or in connection with the healthcare provider marching engine 1024 to retrieve health record data associated with the patient (if there is any stored in the data storage 1050). The health record data may include past interactions between this patient and other healthcare providers, historical test results, current medications the patient is intaking, diagnostics, etc. The health record data (historical data), combined with the requested consult (i.e., current cause for requesting a consult), may set up preliminary criteria for matching this consult with a healthcare provider.

Once the criteria are set (with or without patient's health record data), the healthcare provider matching engine 1024 may query the healthcare provider management module 1028 to identify and/or select one or more healthcare providers that matches the criteria for the consult. Notice that in a time when there are not enough available healthcare providers, the platform may skip this matching step and broadcast the consult to the entire network, and then contact all the available healthcare providers. The healthcare providers' profile, as described elsewhere herein, are taken into consideration by one or more matching algorithms to identify a number of healthcare providers that match the consult. In some embodiments, the one or more matching algorithms may calculate a marching score based on the healthcare providers profiles and the consult. The healthcare providers with a matching score above a pre-determined threshold may be considered as matched, and be notified with the consult. The notified healthcare providers may then view and choose whether or not to accept a consult. Multiple matching algorithms may be utilized by the healthcare provider matching engine 1024 to identify the optimal group of healthcare providers to present to the user, and it may be operated in real-time. For example, a healthcare provider (i.e., doctor) who specializes in respiratory conditions and is currently in low workload may score a high match score when determining whether to match with a consult for a short of breath. A healthcare provider who specializes in bone fracture conditions and is currently in a high workload may score a low match score when determining whether to match with a consult for a short of breath. This matching mechanism may beneficially reduce the overload of internet traffic when there are abundant healthcare providers are available because it may only send the notification of this consult to the healthcare providers with a match score above a predetermined threshold. In some embodiments, the platform may allow a consult initiator to set an urgency level for the consult, and if no healthcare provider responds to the consult in a predefined duration, the platform may broadcast the consult to a bigger group of healthcare providers (e.g., the ones with lower matching scores down the list).

The interactive communication delivery engine 1026 may operate to facilitate communications between healthcare providers and patient (or bedside caregiver). Once a healthcare provider who views and accepts a consult, either party may initiate an online communication. Examples of communications may be in the form of messages (e.g., in-app messaging or via external text messaging systems), audio and/or video calls (e.g., in-app calls or to an external phone number), orders, notes, and the like. The audio and/or video calls may be on-demand, i.e., only be initiated when there is need to. The interactive communication delivery engine 1026 may operate alone or in connection with patient-healthcare provider interface 1030 to provide the functionalities for the communications. Examples of the interfaces and communications are described elsewhere herein.

Data access modules 1042 may facilitate access to data storage 1050 of the server platform 120 by any of the remaining modules 1024, 1026, and 1028 of the server platform 120. In one example, one or more of the data access modules 1042 may be database access modules, or may be any kind of data access module capable of storing data to, and/or retrieving data from, the data storage 1050 according to the needs of the particular module 1024, 126, and 1028 employing the data access modules 1042 to access the data storage 1050. Examples of the data storage 1050 include, but are not limited to, one or more data storage components, such as magnetic disk drives, optical disk drives, solid state disk (SSD) drives, and other forms of nonvolatile and volatile memory components.

In some embodiments, when a patient is treated and recovered from the health condition, the data associated with the consult session may be achieved and saved to the data storage 1050. These data may be later studied, labelled and fed to a machine learning algorithm. The machine learning algorithm may train a prediction model which may: predict a national or regional outbreak of a disease; predict a timeline for treating a patient, provide suggestions (lab tests, medications) to a doctor when a certain consult is received and the patient's vital signs matches with a number of historical examples, provide suggestions to improve the one or more matching algorithms, etc. The machine learning algorithm may comprise one or more of neural networks, Bayesian networks (such as Hidden Markov models), etc. In some embodiments, the machine learning algorithm may collaborate with one or more decision trees, support vector machine, or other systems to assist one or more predictions with large numbers of variables, such as the ones described elsewhere herein.

The system described herein utilizes a patient-centric data model, focusing on a single patient. This provides the ability to easily add multiple patients that scale the system's data model by adding additional integrated clinical environment Data Models to the system, which each may equate to a single patient, or consist of a group of patients. In some embodiments, the data model may include multiple dimensions such as the patient, connected devices/components, time, location, etc. In some embodiments, one important dimensions for tele critical care may be the patient and component values at a specific time. For situational awareness and dashboard data, the most important dimensions may be component and location data (what resources are available at a location).

In some embodiments, the virtual command center and/or user interface dashboard may be configured to display patient data in (near) real-time and/or retrospectively. In some embodiments, the data may be standardized (e.g., via a standard data dictionary with controlled vocabulary), collected, and aggregated by the system as described herein. In some embodiments, the system may be configured to update data when it receives input from a user and/or connected devices. The system may be configured to overwrite the data or create a new, optionally linked, data entry to allow a user (or the system in the case of machine learning) to view patient data entries over time as the patient's situation evolves.

Augmented/Virtual Reality

In some embodiments, the systems and methods described herein utilize augmented reality and/or virtual reality for enhanced communications between the healthcare provider and the patient. A key component of Tele-ICU services (exchanging health information from a hospital critical care unit to another location using via electronic communications to provide real-time services to multiple care centers regardless of their locations.) involves mentoring of the bedside clinicians for clinical procedures and bedside patient data interpretation. Similar to what occurs on a day to day basis in hospitals with mentoring residents, interns and junior physicians, the platforms, systems, methods, and software disclosed herein provide a Tele-ICU service that can be utilized for training and mentoring clinicians who may not have the appropriate skill level as required for critical care. Using technology tools such as AR and VR facilitates such training and mentoring for the bedside clinicians by the remote clinicians.

The AR/VR feature can provide the basis of an augmented audio-visual call allowing remote guidance of the bedside provider by the remote provider, through the use of voice commands by the remote provider to zoom in on areas of interest in the remote provider's field of view without requiring the use of a free hand of the bedside provider, instruction in the use of bedside medical equipment by the remote provider, specific guidance for the performance of a clinical task, or any combination thereof. A wide range of clinical scenarios can be adapted for the use of the AR/VR feature. Such interactive real time tools provide tremendous value in the context of complex clinical scenarios allowing clinicians to function at higher skill levels, eventually translating into better patient outcomes.

Figure 28A:
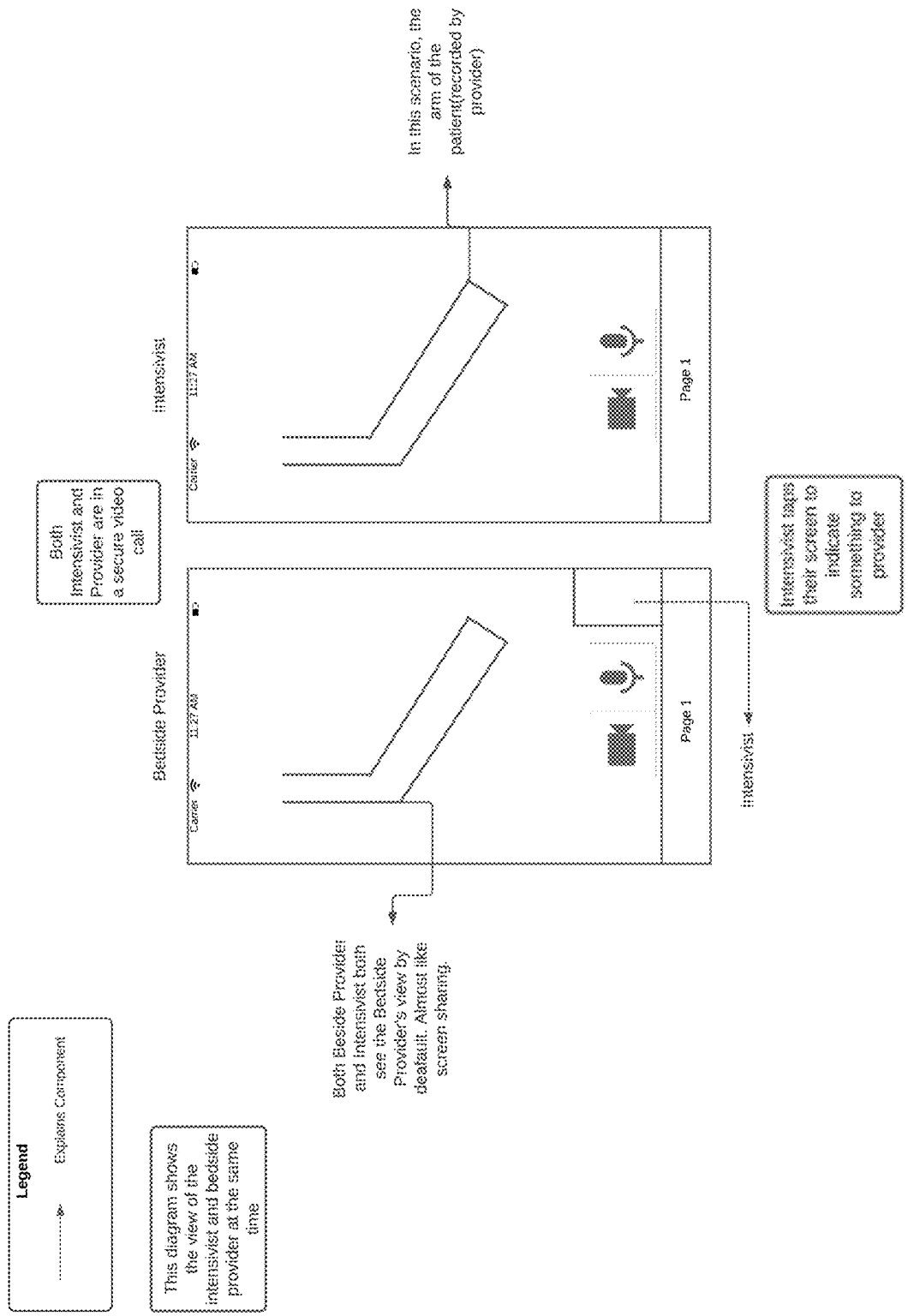
FIG. 28A and FIG. 28B provide illustrative diagrams showing the implementation of augmented reality for a virtual real-time consult between a healthcare provider and a patient, according to one or more embodiments herein.
Figure 28B:
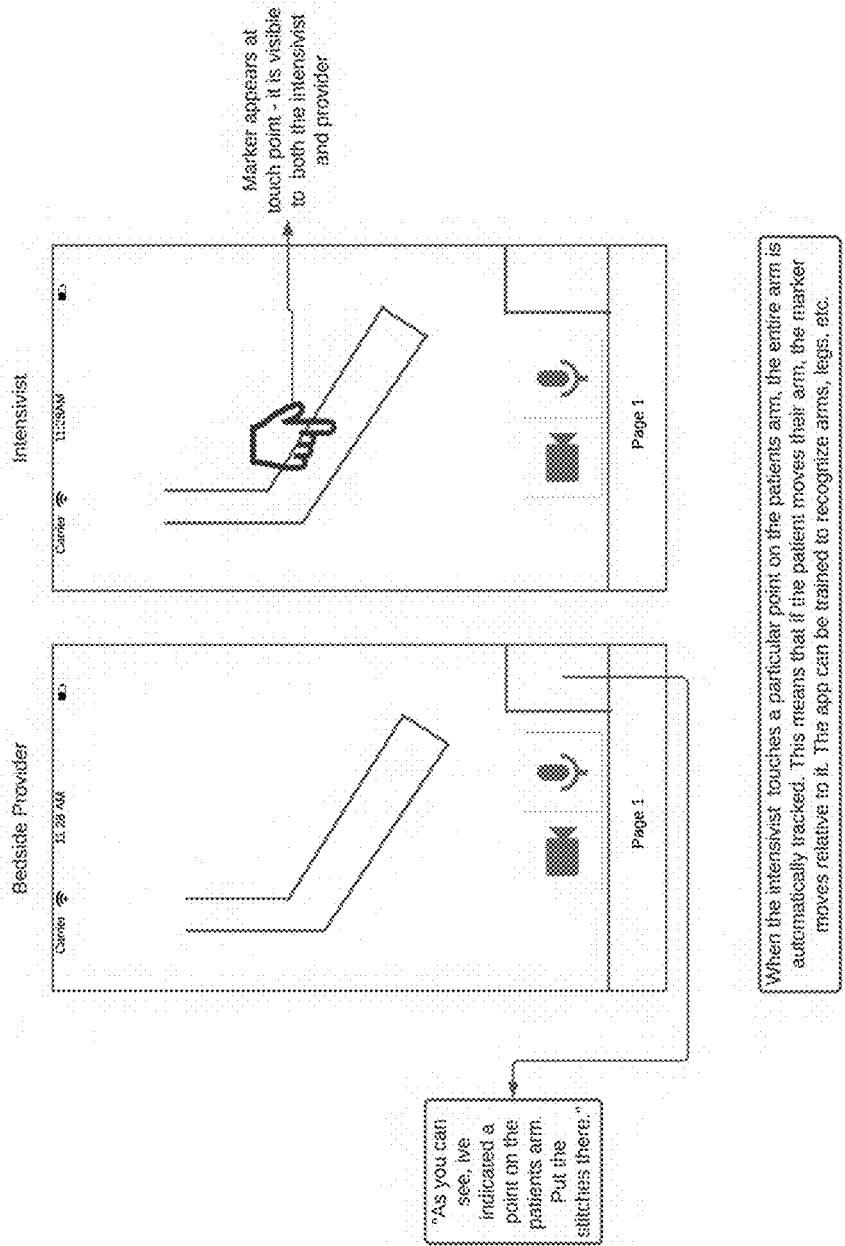
Figure 29A:
FIG. 29A, FIG. 29B, FIG. 29C, and FIG. 29D show a sequence of views illustrating the consultation initiation process, according to one or more embodiments herein.
Figure 29B:
Figure 29C:
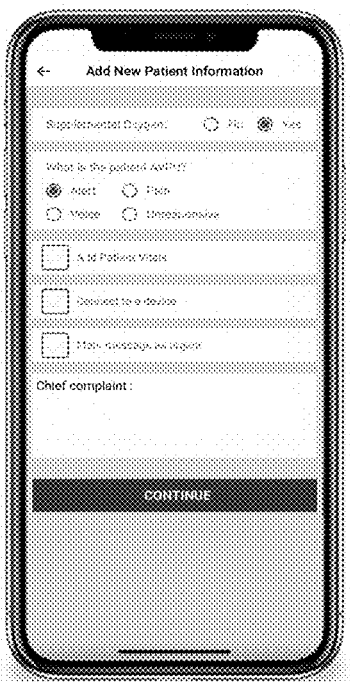
Figure 29D:
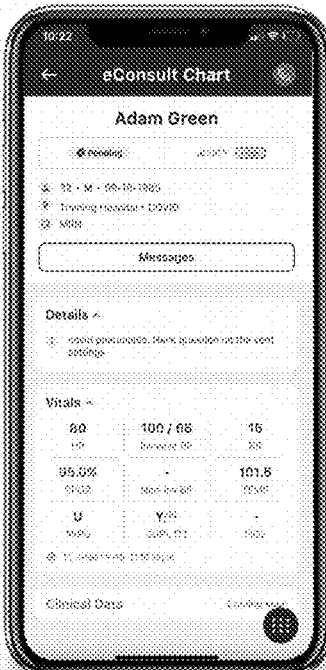
Figure 29E:
FIG. 29E shows a view of a dashboard with an eConsults feature for initiating an electronic consult by inputting relevant patient information for a consult request to be sent to a remote provider's queue, a patient census feature for the patient (which allows initiation of the consultation by selecting a particular patient), a provider directory allowing access to the list of remote healthcare providers available as on-call (e.g., indicated by a status indicator such as a green icon), and eRequests which allows routine requests such as PRN medications, labs, and other such requests to be sent from bedside clinicians in a different category to enhance the remote provider's workflow and streamline such requests for bedside clinicians. This designation can further help remote healthcare providers to prioritize workload.

FIG. 28A and FIG. 28B show a non-limiting illustrative example of the use of augmented reality during a consult. FIG. 28A shows that the remote healthcare provider ("intensivist") and the patient and their local provider ("bedside provider") are engaged in a secure video communication session in which each see the same default view of the patient, in this case, a live video feed of their arm as recorded by the electronic device at the local provider (e.g., a tablet or other suitable device capable of video and audio communications). In this scenario, the remote healthcare provider taps their screen to indicate something to the local provider and/or patient. The tap or any other interaction by the remote healthcare provider with their user interface can be displayed at the local provider/patient's device via a marker or other visual element. In this example shown on FIG. 28B, the marker is displayed on both the remote and local provider digital screens. The marker and the part of the patient's anatomy that was marked can be tracked so that the marker moves along with the anatomical area (e.g., the patient adjusts their arm). This tracking can be accomplished using machine learning and/or computer vision algorithms that are currently available for image segmentation and labeling. For example, deep convolutional neural networks are particularly suitable for image-based analysis and labeling. The remote healthcare provider can provide audio instructions in conjunction with the marker, for example, instructing the local provider to put stitches on the marked portion of the arm or to take a close-up high resolution photo of the region and transmit it to the remote healthcare provider to enable a more detailed view. Although FIG. 28A and FIG. 28B provide one particular illustration of the use of augmented reality within the telemedicine systems of the present disclosure, other uses of augmented reality are contemplated.

Local Edge Communication

In some embodiments, the systems and methods described herein may provide local edge communication. During many mass casualty events, hospitals often resort to paper records or use marking pens to write information directly on the patient because the hospital information systems are overwhelmed or too time consuming to use. Often it takes too long to immediately admit patients or there is no electronic admit system available. Therefore, in some embodiments, the systems and methods described herein may provide a mechanism for data to move with the patient as a patient is transferred from area to area, with or without an internet connection. This mechanism can utilize edge computing to improve respond times and/or reduce bandwidth usage, for example, by moving the storage of the patient's data to the servers, devices, or nodes in the network that are closest to the patient in location. As an illustrative example, a USB drive or the patient's smartphone may be registered within the system to store their medical information, which may be encrypted to only be accessible by an authorized system or device within the network. In the case of an electronic device having a graphic user interface such as a smartphone or tablet, the data may be stored and managed using a software application installed on the device, and can be easily accessible by a third party device by presenting a QR code that can be scanned to access the information (e.g., a nurse's QR code scanner application on a tablet for admitting patients). Similarly, relevant medical data may be transmitted to the healthcare provider such as a clinician who has claimed or accepted a consult request via edge computing.

Data Dictionary and Controlled Vocabularies

The system may be configured with a controlled vocabulary to ensure consistent description of concepts, resources, and their attributes across multiple providers in multiple locations. The controlled vocabulary may be used to normalize medical terms input by users or devices into a standardized format in order to facilitate data entry, storage, and use. In some embodiments, the system may be configured to collect data automatically with the integrated clinical environment and can be used to automatically calculate patient scores (e.g., SOFA and APACHE scores), record dates and times of machine used, etc. In some embodiments, medical data may be encoded in in SNOMED and LOINC where appropriate to facilitate patient intake and/or retrospective data analysis.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

What is claimed is:

1. A computer-implemented system for facilitating communications between healthcare providers, comprising:
   (a) a network element communicatively coupled to a plurality of user communication nodes corresponding to a plurality of bedside healthcare providers and a list of network entities corresponding to remote healthcare providers, wherein the remote healthcare providers are organized into healthcare teams individually assigned to the plurality of bedside healthcare providers;
   (b) one or more computer processors; and
   (c) non-transitory computer readable storage medium comprising executable instructions that, when executed by the one or more computer processors, cause the one or more computer processors to:
   i) receive, from a user communication node corresponding to a bedside healthcare provider of the plurality of bedside healthcare providers, an electronic signal comprising a communication request including a request description comprising a medical condition of a patient;
   ii) select, from the list of network entities corresponding to remote healthcare providers, one or more network entities based at least in part on (i) a parameter profile associated with each remote healthcare provider, and (ii) criteria extracted from the communication request including the description of the medical condition of the patient, wherein the selected one or more network entities correspond to a healthcare team assigned to the bedside healthcare provider of the plurality of bedside healthcare providers;
   iii) transmit an electronic signal, to the one or more network entities corresponding to the healthcare team assigned to the bedside healthcare provider, the communication request including the request description;
   iv) receive an action from one of the selected network entities corresponding to bedside healthcare providers in response to the communication request; and v) provide an interactive communication panel to the user communication node and the one of the selected network entities to facilitate the real-time communication session.

2. The system of claim 1, wherein the one or more computer processors is further caused to aggregate data related to the criteria from a plurality of data sources and processing the data according to a standard format.

3. The system of claim 2, further comprising performing data analytics on the data to generate a suggestion for one or more actions.

4. The system of claim 3, wherein performing data analytics comprises processing the data using a machine learning algorithm.

5. The system of claim 1, wherein the interactive communication panel provides a graphical user interface shown on an interactive touchscreen display.

6. The system of claim 5, wherein the interactive communication panel provides an augmented reality video feed between the user communication node and the one of the selected network entities.

7. The system of claim 6, wherein the one or more computer processors is further caused to provide tracking of an object shown in the augmented reality video feed.

8. The system of claim 7, wherein the object is tracked using a computer vision algorithm trained to detect and track the object.

9. The system of claim 8, wherein the computer vision algorithm comprises an image segmentation algorithm or a machine learning algorithm.

10. The system of claim 9, wherein the machine learning algorithm is a deep convolutional neural network.

11. A computer-implemented method for providing a real-time network communication session between healthcare providers, comprising:
  (a) receiving, by one or more computer processors, from a user communication node corresponding to a bedside healthcare provider, an electronic signal comprising a communication request including a request description comprising a medical condition of a patient;
  (b) selecting, by the one or more computer processors, from a list of network entities corresponding to remote healthcare providers, one or more network entities based at least in part on (i) a parameter profile associated with each remote healthcare provider, and (ii) criteria extracted from the communication request including the description of the medical condition of the patient, wherein the selected one or more network entities correspond to a healthcare team assigned to the bedside healthcare provider;
  (c) transmitting an electronic signal, by the one or more computer processors to the one or more network entities corresponding to the healthcare team assigned to the bedside healthcare provider, the communication request including the request description;
  (d) receiving, by the one or more computer processors, an action from one of the selected network entities corresponding to remote healthcare providers in response to the communication request; and
  (e) providing, by the one or more computer processors, an interactive communication panel to the user communication node and the one of the selected network entities to facilitate the real-time communication session.

12. The computer-implemented method of claim 11, further comprising aggregating data related to the criteria from a plurality of data sources and processing the data according to a standard format.

13. The computer-implemented method of claim 12, further comprising performing data analytics on the data to generate a suggestion for one or more actions.

14. The computer-implemented method of claim 13, wherein performing data analytics comprises processing the data using a machine learning algorithm.

15. The computer-implemented method of claim 11, wherein the interactive communication panel provides a graphical user interface shown on an interactive touchscreen display.

16. The computer-implemented method of claim 15, wherein the interactive communication panel provides an augmented reality video feed between the user communication node and the one of the selected network entities.

17. The computer-implemented method of claim 16, further comprising providing tracking of an object shown in the augmented reality video feed.

18. The computer-implemented method of claim 17, wherein the object is tracked using a computer vision algorithm trained to detect and track the object.

19. The computer-implemented method of claim 18, wherein the computer vision algorithm comprises an image segmentation algorithm or a machine learning algorithm.

20. The computer-implemented method of claim 19, wherein the machine learning algorithm is a deep convolutional neural network.

21. The computer-implemented method of claim 11, wherein the healthcare teams are generated based on staffing ratios that are built-in, user-generated, or automatically-generated.

22. The computer-implemented method of claim 11, wherein patient matching is performed in real-time using an algorithm based on estimated medical demand.

23. The computer-implemented method of claim 11, wherein the interactive communication panel is integrated with one or more bedside device, wearable monitoring device, or biosensor device to transmit patient data.

* * * * *